US005773701A

United States Patent [19]
Braun, III et al.

[11] Patent Number: 5,773,701
[45] Date of Patent: Jun. 30, 1998

[54] PLANTS RESISTANT TO INFECTION BY PVX

[75] Inventors: Carl Joseph Braun, III, Creve Coeur; Cynthia Lou Hemenway, St. Louis; Nilgun Ereken Tumer, Chesterfield, all of Mo.

[73] Assignee: Monsanto Company, St. Louis, Mo.

[21] Appl. No.: 803,973

[22] Filed: Feb. 21, 1997

Related U.S. Application Data

[63] Continuation of Ser. No. 804,862, Dec. 6, 1991, abandoned, which is a continuation-in-part of Ser. No. 771,912, Oct. 4, 1991, abandoned.

[51] Int. Cl.[6] .......... C12N 5/10; C12N 15/63; C12N 15/82; A01H 5/00

[52] U.S. Cl. .......... 800/205; 800/DIG. 40; 800/DIG. 42; 800/DIG. 44; 536/23.72; 435/172.1; 435/172.3; 435/320.1; 435/375

[58] Field of Search .......... 435/172.1, 172.3, 435/320.1, 375, 69.1, 70.1, 91.1, 235.1, 236, 237, 417; 800/205, DIG. 40, DIG. 42, DIG. 44; 536/23.72

[56] References Cited

U.S. PATENT DOCUMENTS 5,580,716 12/1996 Johnston et al. .......... 435/5
5,596,132 1/1997 Zaitlin et al. .......... 800/205
5,633,449 5/1997 Zaitlin et al. .......... 800/205

FOREIGN PATENT DOCUMENTS

WO 91/13542 9/1991 WIPO .......... A01H 5/00

OTHER PUBLICATIONS

Abel, et al. (1986) *Science* 232:738–743.
Bevan, (1984) *Nucl. Acids Res.* 12:8711–8721.
Braun, Carl J. and Hemenway, Cynthia L., (1992) *The Plant Cell* 4:735–744.
Carr, Peter and Zaitlin, Milton (1993) Seminars in Virology 4:339–347.
Coruzzi, et al. (1990) *EMBO J.* 3:6171.
Cuozzo, et al. (1988) *Bio Technol.* 6:549–557.
deBokx, (1972) Viruses of Potatoes and Seed–Potato Production, p. 233, Centre for Agric. Publ. and Documentation, Wegenigen, The Netherlands.
deBokx, (1986) Potato Virus Y. in: Compendium of Potato Diseases, pp. 7–71, W. Hooker ed., American Phytopathology Society.
Ditta, et al. (1980) *Proc. Natl. Acad. Sci. USA* 77:7347–7351.
Fling, et al. (1985) *Nucl. Acids Res.* 13:7095–7106.
Fraley, et al. (1985) *Proc. Natl. Acad. Sci. USA* 80:4803–4807.
Golemboski, et al. (1990) *Proc. Natl. Acad. Sci. USA* 87:6311–6315.
Hemenway, et al. (1988) *EMBO J.* 7:1273–1280.
Hemenway, et al. (1990) *Virology* 175:365–371.
Herrera–Estrella (1983) *Nature* 303:209.
Hodgman (1988) *Nature* 333:22–23.
Horsch, et al. (1985) *Science* 227:1229–1231.
Huisman, et al. (1988) *J. Gen. Virol.* 69:1789–1798.
Ishikawa, et al. (1986) *Nucleic Acids Res.* 14:8291–8305.
Kaniewski, et al., (1990) *BioTechnol.* 8:750–754.
Kay, et al., (1987) *Science* 236:1299–1302.
Klee, et al., (1985) *BioTechnol.* 3:637–642.
Koncz and Schell, (1986) *Mol. Gen. Genet.* 204:383–396.
Kunkel, (1985) *Proc. Natl. Acad. Sci, USA* 82:488–492.
Lawson, et al. (1990) *BioTechnol.* 8:127–134.
Odell, et al. (1985) *Nature* 313:810–812.
Purcifull and Eswardson (1981) in: Handbook of Plant Virus Infections and Comparative Diagnosis. E. Jurstak ed. Elsevier/North Holland Biomedical Press.
Skryabin, et al. (1988) *FEBS Lett.* 240:33–40.
Stalker, et al. (1981) *Mol. Gen. Genet.* 181:8–12.
Stark and Beachy, (1989) *BioTechnol.* 7:1257–1262.
Taschner, et al. (1991) *Virology* 181:445–450.
Todd, (1957) *Proc 3rd Conf. Potato Virus Diseases*, p. 132. Lisse–Wageninger, The Netherlands.
Thomas, (1980) *Proc. Natl. Acad. Sci. USA* 77:5201–5205.
Tumer, et al. (1987) *EMBO J.* 6:1181–1188.
van Dun, et al., (1988) *Virology* 163:572–578.
van Dun, et al., (1988) *Virology* 164:383–389.
Zuidema, et al. (1980) *J. Gen. Virol.* 70:267276.
M. Huisman et al. J. Gen. Virol. 69:1789–98, 1988.
D. Ow et al. PNAS 84: 4870–74, 1987.

*Primary Examiner*—Charles C.P. Rories
*Attorney, Agent, or Firm*—Grace L. Bonner; Arnold, White & Durkee

[57] ABSTRACT

A DNA sequence encoding a PVX replicase gene obtained from ORF1 of a PVX genome is provided. A plant gene containing the PVX replicase coding region is also provided as is a truncated derivative of the PVX replicase gene. A PVX replicase gene is inserted into a plant to confer resistance to the plant against PVX infection when the PVX replicase gene is sufficiently expressed.

10 Claims, 28 Drawing Sheets

```
       10              30              50
        .               .               .
GAAAACTAAACCATACACCACCAACACAACCAAACCCACCACGCCCAATTGTTACACACC
---------+---------+---------+---------+---------+---------+

70              90             110
        .               .               .
CGCTTGAAAAAGCAAGTCTGACAAATGGCCAAAGTGCGCGAGGTTTACCAATCCTTTACA
---------+---------+---------+---------+---------+---------+
                            MetAlaLysValArgGluValTyrGlnSerPheThr 130             150             170
        .               .               .
GACTCCACCACAAAAACTCTCATCCAAGATGAGGCTTATAGAAATATTCGTCCCATCATG
---------+---------+---------+---------+---------+---------+
AspSerThrThrLysThrLeuIleGlnAspGluAlaTyrArgAsnIleArgProIleMet 190             210             230
        .               .               .
GAAAAACATAAACTAGCTAACCCGTACGCTCAAACGGTTGAAGCGGCTAATGATCTAGAG
---------+---------+---------+---------+---------+---------+
GluLysHisLysLeuAlaAsnProTyrAlaGlnThrValGluAlaAlaAsnAspLeuGlu 250             270             290
        .               .               .
GGGTTCGGCATAGCCACCAATCCCTATAGCATTGAGTTGCATACACATGCAGCTGCTAAG
---------+---------+---------+---------+---------+---------+
GlyPheGlyIleAlaThrAsnProTyrSerIleGluLeuHisThrHisAlaAlaAlaLys 310             330             350
        .               .               .
ACCATAGAGAATAAACTTCTAGAGGTGCTTGGTTCCATCCTACCACAAGAACCTGTTACA
---------+---------+---------+---------+---------+---------+
ThrIleGluAsnLysLeuLeuGluValLeuGlySerIleLeuProGlnGluProValThr 370             390             410
        .               .               .
TTTATGTTCCTTAAACCCAGGAAGCTAAACTACATGAGAAGAAACCCGCGGATCAAGGAC
---------+---------+---------+---------+---------+---------+
PheMetPheLeuLysProArgLysLeuAsnTyrMetArgArgAsnProArgIleLysAsp 430             450             470
        .               .               .
ATTTTCCACAATGTTGCCATTGAACCGAGAGACGTAGCAAGGTACCCCAAGGAAACAATA
---------+---------+---------+---------+---------+---------+
IlePheHisAsnValAlaIleGluProArgAspValAlaArgTyrProLysGluThrIle 490             510             530
        .               .               .
ATTGACAAACTCACAGAGATCACAACAGACACAGCATACATTAGTGACACTCTGCACTTC
---------+---------+---------+---------+---------+---------+
IleAspLysLeuThrGluIleThrThrAspThrAlaTyrIleSerAspThrLeuHisPhe
```

FIG. 1A

```
              550                 570                 590
               .                   .                   .
    TTGGATCCGAGCTACATAGTGGAGACATTCCAAAACTGCCCAAAACTGCAAACATTGTAT
    ---------+---------+---------+---------+---------+---------+
    LeuAspProSerTyrIleValGluThrPheGlnAsnCysProLysLeuGlnThrLeuTyr 610                 630                 650
               .                   .                   .
    GCGACCTTAGTTCTCCCCGTTGAGGCAGCCTTCAAAATGGAAAGCACTCACCCGAACATA
    ---------+---------+---------+---------+---------+---------+
    AlaThrLeuValLeuProValGluAlaAlaPheLysMetGluSerThrHisProAsnIle 670                 690                 710
               .                   .                   .
    TACAGCCTCAAATACTTCGGAGATGGTTTCCAGTATATACCAGGCAACCATGGTGGTGGA
    ---------+---------+---------+---------+---------+---------+
    TyrSerLeuLysTyrPheGlyAspGlyPheGlnTyrIleProGlyAsnHisGlyGlyGly 730                 750                 770
               .                   .                   .
    GCGTACCATCATGAATTTGCTCATTTACAATGGCTCAAAGTGGGAAAGATCAAATGGAGG
    ---------+---------+---------+---------+---------+---------+
    AlaTyrHisHisGluPheAlaHisLeuGlnTrpLeuLysValGlyLysIleLysTrpArg 790                 810                 830
               .                   .                   .
    GACCCCAAGGATAGCTTTCTCGGACATCTCAATTACACGACTGAGCAGGTTGAGATGCAC
    ---------+---------+---------+---------+---------+---------+
    AspProLysAspSerPheLeuGlyHisLeuAsnTyrThrThrGluGlnValGluMetHis 850                 870                 890
               .                   .                   .
    ACAGTGACAGTGCAGTTGCAGGAATCGTTCGCGGCAAACCACTTGTACTGCATCAGGAGA
    ---------+---------+---------+---------+---------+---------+
    ThrValThrValGlnLeuGlnGluSerPheAlaAlaAsnHisLeuTyrCysIleArgArg 910                 930                 950
               .                   .                   .
    GGAGATTTGCTCACACCGGAGGTGCGCACTTTTGGCCAACCTGACAGGTATGTGATTCCA
    ---------+---------+---------+---------+---------+---------+
    GlyAspLeuLeuThrProGluValArgThrPheGlyGlnProAspArgTyrValIlePro 970                 990                1010
               .                   .                   .
    CCACAGATCTTCCTCCCGAAAGTCCATAACTGCAAGAAGCCGATTCTTAAAAAAACTATG
    ---------+---------+---------+---------+---------+---------+
    ProGlnIlePheLeuProLysValHisAsnCysLysLysProIleLeuLysLysThrMet 1030                1050                1070
               .                   .                   .
    ATGCAGCTCTTCTTGTATGTTAGGACAGTTAAGGTCGCAAAAAATTGTGACATTTTTGCC
    ---------+---------+---------+---------+---------+---------+
    MetGlnLeuPheLeuTyrValArgThrValLysValAlaLysAsnCysAspIlePheAla
```

FIG. 1B

```
                    1090                1110                1130
        AAAGTCAGACAATTAATTAAATCATCTGACCTGGACAAATATTCTGCTGTGGAACTGGTT
        ---------+---------+---------+---------+---------+---------+
        LysValArgGlnLeuIleLysSerSerAspLeuAspLysTyrSerAlaValGluLeuVal 1150                1170                1190
        TACTTAGTAAGCTATATGGAGTTCCTTGCCGATCTACAAGCTACCACCTGCTTCTCAGAC
        ---------+---------+---------+---------+---------+---------+
        TyrLeuValSerTyrMetGluPheLeuAlaAspLeuGlnAlaThrThrCysPheSerAsp 1210                1230                1250
        ACACTTTCTGGTGGCTTACTAACAAAGACCCTTGCACCGGTGAGGGCTTGGATACAAGAG
        ---------+---------+---------+---------+---------+---------+
        ThrLeuSerGlyGlyLeuLeuThrLysThrLeuAlaProValArgAlaTrpIleGlnGlu 1270                1290                1310
        AAAAAGATGCAGCTGTTTGGTCTTGAGGACTACGCGAAGTTAGTCAAAGCAGTTGATTTC
        ---------+---------+---------+---------+---------+---------+
        LysLysMetGlnLeuPheGlyLeuGluAspTyrAlaLysLeuValLysAlaValAspPhe 1330                1350                1370
        CACCCAGTGGATTTTTCTTTTAAAGTTGAAACTTGGGACTTCAGATTCCACCCCTTGCAA
        ---------+---------+---------+---------+---------+---------+
        HisProValAspPheSerPheLysValGluThrTrpAspPheArgPheHisProLeuGln 1390                1410                1430
        GCGTGGAAAGCCTTCCGACCAAGGGAAGTGTCGGATGTAGAGGAAATGGAAAGTTTGTTC
        ---------+---------+---------+---------+---------+---------+
        AlaTrpLysAlaPheArgProArgGluValSerAspValGluGluMetGluSerLeuPhe 1450                1470                1490
        TCAGATGGGGACCTGCTTGACTGCTTCACAAGAATGCCAGCTTATGCAGTAAACGCAGAG
        ---------+---------+---------+---------+---------+---------+
        SerAspGlyAspLeuLeuAspCysPheThrArgMetProAlaTyrAlaValAsnAlaGlu 1510                1530                1550
        GAAGATTTAGCTACAATCAGGAAAACGCCCGAGATGGATGTCGGTCAAGAAGCCAAAGAA
        ---------+---------+---------+---------+---------+---------+
        GluAspLeuAlaThrIleArgLysThrProGluMetAspValGlyGlnGluAlaLysGlu 1570                1590                1610
        CCTGCAGGAGACAGAAATCAATACTTAAACCCTGCAGAAACTTTCCTCAACAAGCTCCAC
        ---------+---------+---------+---------+---------+---------+
        ProAlaGlyAspArgAsnGlnTyrLeuAsnProAlaGluThrPheLeuAsnLysLeuHis
```

FIG. 1C

```
              1630                1650                1670
                .                  .                  .
    AGGAAACACAGTAGGGAGGTGAAACATCAGGCCGTAAAGAAAGCTAAACGCCTAGCTGAA
    ---------+---------+---------+---------+---------+---------+
    ArgLysHisSerArgGluValLysHisGlnAlaValLysLysAlaLysArgLeuAlaGlu 1690                1710                1730
                .                  .                  .
    ATCCAGGAGTCCATGAGAGCTGAGGGTGAGGCCGAACTAAATGAGATGAGCGGGGGCATG
    ---------+---------+---------+---------+---------+---------+
    IleGlnGluSerMetArgAlaGluGlyGluAlaGluLeuAsnGluMetSerGlyGlyMet 1750                1770                1790
                .                  .                  .
    AGGGCAATACCTAGCAACGCAGAACTTCCCAGCACGAACGATGCTAGACAAGAACTCACA
    ---------+---------+---------+---------+---------+---------+
    ArgAlaIleProSerAsnAlaGluLeuProSerThrAsnAspAlaArgGlnGluLeuThr 1810                1830                1850
                .                  .                  .
    CTCCCAACCACTAAACCTGTCCCTGCAAGGTGGGAAGATGCTTCATTCACAGATTCTAGT
    ---------+---------+---------+---------+---------+---------+
    LeuProThrThrLysProValProAlaArgTrpGluAspAlaSerPheThrAspSerSer 1870                1890                1910
                .                  .                  .
    GTGAAAGAGGAGCAAGTGAAACTCCCTGGAAAAGAAGCCGTTGAGACAGCGACGCAACAA
    ---------+---------+---------+---------+---------+---------+
    ValLysGluGluGlnValLysLeuProGlyLysGluAlaValGluThrAlaThrGlnGln 1930                1950                1970
                .                  .                  .
    GTCATAGAAGGACTCCCTTGGAAACACTGGATTCCTCAACTAAATGCTGTTGGATTCAAG
    ---------+---------+---------+---------+---------+---------+
    ValIleGluGlyLeuProTrpLysHisTrpIleProGlnLeuAsnAlaValGlyPheLys 1990                2010                2030
                .                  .                  .
    GCGCTGGAAATTCAGAGGGATAGGAGTGGGACAATGATCATGCCCATCACAGAAATGGTC
    ---------+---------+---------+---------+---------+---------+
    AlaLeuGluIleGlnArgAspArgSerGlyThrMetIleMetProIleThrGluMetVal 2050                2070                2090
                .                  .                  .
    TCCGGGTTGGAAAAGAGGACTTCCCGGAAGGAACTCCAAAAGAGTTGGCACGAGAATTG
    ---------+---------+---------+---------+---------+---------+
    SerGlyLeuGluLysGluAspPheProGluGlyThrProLysGluLeuAlaArgGluLeu 2110                2130                2150
                .                  .                  .
    CTCGCTATGAACAGAAGCCCTGCCACCATTCCTTTGGACCTGCTTAGAGCCAGAGACTAC
    ---------+---------+---------+---------+---------+---------+
    LeuAlaMetAsnArgSerProAlaThrIleProLeuAspLeuLeuArgAlaArgAspTyr
```

FIG. 1D

```
         2170                2190                 2210
GGCAGTGATGTGAAGAACAAGAGAATTGGTGCCATCACAAAGACACAAGCAACAAGTTGG
---------+---------+---------+---------+---------+---------+
GlySerAspValLysAsnLysArgIleGlyAlaIleThrLysThrGlnAlaThrSerTrp 2230                2250                 2270
GGCGAGTACCTAACAGGAAAGATAGAAAGTCTGACTGAGAGGAAAGTTGCGACTTGTGTC
---------+---------+---------+---------+---------+---------+
GlyGluTyrLeuThrGlyLysIleGluSerLeuThrGluArgLysValAlaThrCysVal 2290                2310                 2330
ATTCATGGAGCTGGAGGCTCTGGGAAAAGTCATGCCATCCAGAAGGCATTGAGAGAAATT
---------+---------+---------+---------+---------+---------+
IleHisGlyAlaGlyGlySerGlyLysSerHisAlaIleGlnLysAlaLeuArgGluIle 2350                2370                 2390
GGCAAGGGGTCAGACATCACTGTAGTCCTGCCGACCAATGAACTGCGACTAGATTGGAGC
---------+---------+---------+---------+---------+---------+
GlyLysGlySerAspIleThrValValLeuProThrAsnGluLeuArgLeuAspTrpSer 2410                2430                 2450
AAGAAAGTGCCTAACACTGAACCATATATGTTCAAGACCTATGAAAAGGCATTAATTGGG
---------+---------+---------+---------+---------+---------+
LysLysValProAsnThrGluProTyrMetPheLysThrTyrGluLysAlaLeuIleGly 2470                2490                 2510
GGAACAGGCAGTATAGTCATCTTTGACGATTACTCAAAACTTCCTCCCGGTTACATAGAA
---------+---------+---------+---------+---------+---------+
GlyThrGlySerIleValIlePheAspAspTyrSerLysLeuProProGlyTyrIleGlu 2530                2550                 2570
GCCTTAATCTGTTTCTACTCTAAAATCAAGCTAGTCATTCTAACAGGAGATAGCAGACAG
---------+---------+---------+---------+---------+---------+
AlaLeuIleCysPheTyrSerLysIleLysLeuValIleLeuThrGlyAspSerArgGln 2590                2610                 2630
AGCGTCTACCATGAAACTGCTGAGGACGCCTCCATCAGGCATTTGGGACCAGCGACAGAG
---------+---------+---------+---------+---------+---------+
SerValTyrHisGluThrAlaGluAspAlaSerIleArgHisLeuGlyProAlaThrGlu 2650                2670                 2690
TACTTCTCAAAATACTGCCGATACTATCTCAATGCTACACACCGCAACAAGAAAGACCTT
---------+---------+---------+---------+---------+---------+
TyrPheSerLysTyrCysArgTyrTyrLeuAsnAlaThrHisArgAsnLysLysAspLeu
```

FIG. 1E

```
         2710                    2730                    2750
          .                       .                       .
GCGAACATGCTCGGTGTCTACAGTGAGAGAACGGGGGTCACCGAAATCAGCATGAGCGCC
----------+---------+----------+----------+---------+---------+
AlaAsnMetLeuGlyValTyrSerGluArgThrGlyValThrGluIleSerMetSerAla 2770                    2790                    2810
          .                       .                       .
GAGTTCTTAGAAGGAATCCCAACTTTAGTACCCTCGGATGAGAAGAGAAAGCTGTACATG
----------+---------+----------+----------+---------+---------+
GluPheLeuGluGlyIleProThrLeuValProSerAspGluLysArgLysLeuTyrMet 2830                    2850                    2870
          .                       .                       .
GGCACCGGGAGGAACGACACGTTCACATACGCTGGATGCCAGGGGCTGACCAAGCCGAAA
----------+---------+----------+----------+---------+---------+
GlyThrGlyArgAsnAspThrPheThrTyrAlaGlyCysGlnGlyLeuThrLysProLys 2890                    2910                    2930
          .                       .                       .
GTACAAATAGTGTTGGACCACAACACCCAAGTGTGTAGCGCGAATGTGATGTACACGGCA
----------+---------+----------+----------+---------+---------+
ValGlnIleValLeuAspHisAsnThrGlnValCysSerAlaAsnValMetTyrThrAla 2950                    2970                    2990
          .                       .                       .
CTTTCTAGAGCCACCGACAGGATTCACTTCGTGAACACAAGTGCAAACTCTTCGGCCTTC
----------+---------+----------+----------+---------+---------+
LeuSerArgAlaThrAspArgIleHisPheValAsnThrSerAlaAsnSerSerAlaPhe 3010                    3030                    3050
          .                       .                       .
TGGGAAAAGTTAGACAGCACCCCTTATCTCAAGACTTTCCTATCAGTGGTGAGAGAACAA
----------+---------+----------+----------+---------+---------+
TrpGluLysLeuAspSerThrProTyrLeuLysThrPheLeuSerValValArgGluGln 3070                    3090                    3110
          .                       .                       .
GCACTCAGGGAGTACGAGCCGGCAGAGGCAGAGCCAATTCGAGAGCCTGAGCCCCAGACA
----------+---------+----------+----------+---------+---------+
AlaLeuArgGluTyrGluProAlaGluAlaGluProIleArgGluProGluProGlnThr 3130                    3150                    3170
          .                       .                       .
CACATGTGTGTCGAGAATGAGGAGTCCGTGCTAGAAGAGTACAAAGAGGAACTCTTGGAA
----------+---------+----------+----------+---------+---------+
HisMetCysValGluAsnGluGluSerValLeuGluGluTyrLysGluGluLeuLeuGlu 3190                    3210                    3230
          .                       .                       .
AAGTTTGACAGAGAGATCCACTCGGAATCCCATGGTCATTCAAACTGTGTCCAAACAGAA
----------+---------+----------+----------+---------+---------+
LysPheAspArgGluIleHisSerGluSerHisGlyHisSerAsnCysValGlnThrGlu
```

FIG. 1F

```
                  3790                 3810                3830
         AATTTCGGCAGACCTAGCTTGGCCAATGACTACACAGCTTTCGACCAGTCTCAGGATGGA
         ---------+---------+---------+---------+---------+---------+
          AsnPheGlyArgProSerLeuAlaAsnAspTyrThrAlaPheAspGlnSerGlnAspGly 3850                 3870                3890
         GCTATGCTGCAATTTGAGGTGCTCAAAGCCAAGCACCATTGCATACCAGAGGAAATCATC
         ---------+---------+---------+---------+---------+---------+
          AlaMetLeuGlnPheGluValLeuLysAlaLysHisHisCysIleProGluIleIle 3910                 3930                3950
         CAAGCATACATAGACATTAAGACCAATGCACAGATTTTCCTAGGCACATTGTCAATCATG
         ---------+---------+---------+---------+---------+---------+
          GlnAlaTyrIleAspIleLysThrAsnAlaGlnIlePheLeuGlyThrLeuSerIleMet 3970                 3990                4010
         CGCCTGACTGGTGAGGGTCCCACTTTTGATGCAAACACTGAGTGCAACATAGCTTACACC
         ---------+---------+---------+---------+---------+---------+
          ArgLeuThrGlyGluGlyProThrPheAspAlaAsnThrGluCysAsnIleAlaTyrThr 4030                 4050                4070
         CATACAAAGTTTGACATCCCAGCAGGAACTGCTCAAGTTTATGCAGGAGACGACTCAGCA
         ---------+---------+---------+---------+---------+---------+
          HisThrLysPheAspIleProAlaGlyThrAlaGlnValTyrAlaGlyAspAspSerAla 4090                 4110                4130
         CTGGATTGCGTTCCAGAAGTGAAGCATAGCTTCCACAGGCTTGAAGACAAACTACTCCTT
         ---------+---------+---------+---------+---------+---------+
          LeuAspCysValProGluValLysHisSerPheHisArgLeuGluAspLysLeuLeuLeu 4150                 4170                4190
         AAGTCAAAGCCCGTAATCACGCAGCAAAAGAAAGGCAGTTGGCCTGAGTTTTGTGGTTGG
         ---------+---------+---------+---------+---------+---------+
          LysSerLysProValIleThrGlnGlnLysLysGlySerTrpProGluPheCysGlyTrp 4210                 4230                4250
         CTGATTACACCAAAAGGGGTAATGAAAGACCCAATTAAGCTCCATGTTAGCTTAAAATTG
         ---------+---------+---------+---------+---------+---------+
          LeuIleThrProLysGlyValMetLysAspProIleLysLeuHisValSerLeuLysLeu 4270                 4290                4310
         GCCGAAGCTAAGGGCGAACTCAAGAAATGTCAAGACTCCTATGAAATTGATCTGAGTTAT
         ---------+---------+---------+---------+---------+---------+
          AlaGluAlaLysGlyGluLeuLysLysCysGlnAspSerTyrGluIleAspLeuSerTyr
```

FIG. 1G

```
         3790                3810                3830
            .                   .                   .
AATTTCGGCAGACCTAGCTTGGCCAATGACTACACAGCTTTCGACCAGTCTCAGGATGGA
----------+---------+---------+---------+---------+---------+
AsnPheGlyArgProSerLeuAlaAsnAspTyrThrAlaPheAspGlnSerGlnAspGly 3850                3870                3890
            .                   .                   .
GCTATGCTGCAATTTGAGGTGCTCAAAGCCAAGCACCATTGCATACCAGAGGAAATCATC
----------+---------+---------+---------+---------+---------+
AlaMetLeuGlnPheGluValLeuLysAlaLysHisHisCysIleProGluGluIleIle 3910                3930                3950
            .                   .                   .
CAAGCATACATAGACATTAAGACCAATGCACAGATTTTCCTAGGCACATTGTCAATCATG
----------+---------+---------+---------+---------+---------+
GlnAlaTyrIleAspIleLysThrAsnAlaGlnIlePheLeuGlyThrLeuSerIleMet 3970                3990                4010
            .                   .                   .
CGCCTGACTGGTGAGGGTCCCACTTTTGATGCAAACACTGAGTGCAACATAGCTTACACC
----------+---------+---------+---------+---------+---------+
ArgLeuThrGlyGluGlyProThrPheAspAlaAsnThrGluCysAsnIleAlaTyrThr 4030                4050                4070
            .                   .                   .
CATACAAAGTTTGACATCCCAGCAGGAACTGCTCAAGTTTATGCAGGAGACGACTCAGCA
----------+---------+---------+---------+---------+---------+
HisThrLysPheAspIleProAlaGlyThrAlaGlnValTyrAlaGlyAspAspSerAla 4090                4110                4130
            .                   .                   .
CTGGATTGCGTTCCAGAAGTGAAGCATAGCTTCCACAGGCTTGAAGACAAACTACTCCTT
----------+---------+---------+---------+---------+---------+
LeuAspCysValProGluValLysHisSerPheHisArgLeuGluAspLysLeuLeuLeu 4150                4170                4190
            .                   .                   .
AAGTCAAAGCCCGTAATCACGCAGCAAAAGAAAGGCAGTTGGCCTGAGTTTTGTGGTTGG
----------+---------+---------+---------+---------+---------+
LysSerLysProValIleThrGlnGlnLysLysGlySerTrpProGluPheCysGlyTrp 4210                4230                4250
            .                   .                   .
CTGATTACACCAAAAGGGGTAATGAAAGACCCAATTAAGCTCCATGTTAGCTTAAAATTG
----------+---------+---------+---------+---------+---------+
LeuIleThrProLysGlyValMetLysAspProIleLysLeuHisValSerLeuLysLeu 4270                4290                4310
            .                   .                   .
GCCGAAGCTAAGGGCGAACTCAAGAAATGTCAAGACTCCTATGAAATTGATCTGAGTTAT
----------+---------+---------+---------+---------+---------+
AlaGluAlaLysGlyGluLeuLysLysCysGlnAspSerTyrGluIleAspLeuSerTyr
```

FIG. 1H

```
                4330                   4350                   4370
GCCTACGACCACAAGGACTCTCTGCATGACTTGTTCGATGAGAAACAGTGTCAGGCACAT
---------+---------+---------+---------+---------+---------+
AlaTyrAspHisLysAspSerLeuHisAspLeuPheAspGluLysGlnCysGlnAlaHis 4390                   4410                   4430
ACACTCACTTGCAGAACACTGATCAAGTCAGGGAGAGGCACTGTCTCACTTCCCCGCCTC
---------+---------+---------+---------+---------+---------+
ThrLeuThrCysArgThrLeuIleLysSerGlyArgGlyThrValSerLeuProArgLeu

4450
AGAAACTTTCTTTAA
---------+-----
ArgAsnPheLeuEnd
```

FIG. 1I

```
          10                  30                  50
           .                   .                   .
GAAAACTAAACCATACACCACCAACACAACCAAACCCACCACGCCCAATTGTTACACACC
---------+---------+---------+---------+---------+---------+

70                  90                 110
           .                   .                   .
CGCTTGAAAAAGCAAGTCTGACAAATGGCCAAAGTGCGCGAGGTTTACCAATCCTTTACA
---------+---------+---------+---------+---------+---------+
                              MetAlaLysValArgGluValTyrGlnSerPheThr 130                 150                 170
           .                   .                   .
GACTCCACCACAAAAACTCTCATCCAAGATGAGGCTTATAGAAATATTCGTCCCATCATG
---------+---------+---------+---------+---------+---------+
AspSerThrThrLysThrLeuIleGlnAspGluAlaTyrArgAsnIleArgProIleMet 190                 210                 230
           .                   .                   .
GAAAAACATAAACTAGCTAACCCGTACGCTCAAACGGTTGAAGCGGCTAATGATCTAGAG
---------+---------+---------+---------+---------+---------+
GluLysHisLysLeuAlaAsnProTyrAlaGlnThrValGluAlaAlaAsnAspLeuGlu 250                 270                 290
           .                   .                   .
GGGTTCGGCATAGCCACCAATCCCTATAGCATTGAGTTGCATACACATGCAGCTGCTAAG
---------+---------+---------+---------+---------+---------+
GlyPheGlyIleAlaThrAsnProTyrSerIleGluLeuHisThrHisAlaAlaAlaLys 310                 330                 350
           .                   .                   .
ACCATAGAGAATAAACTTCTAGAGGTGCTTGGTTCCATCCTACCACAAGAACCTGTTACA
---------+---------+---------+---------+---------+---------+
ThrIleGluAsnLysLeuLeuGluValLeuGlySerIleLeuProGlnGluProValThr 370                 390                 410
           .                   .                   .
TTTATGTTCCTTAAACCCAGGAAGCTAAACTACATGAGAAGAAACCCGCGGATCAAGGAC
---------+---------+---------+---------+---------+---------+
PheMetPheLeuLysProArgLysLeuAsnTyrMetArgArgAsnProArgIleLysAsp 430                 450                 470
           .                   .                   .
ATTTTCCACAATGTTGCCATTGAACCGAGAGACGTAGCAAGGTACCCCAAGGAAACAATA
---------+---------+---------+---------+---------+---------+
IlePheHisAsnValAlaIleGluProArgAspValAlaArgTyrProLysGluThrIle 490                 510                 530
           .                   .                   .
ATTGACAAACTCACAGAGATCACAACAGACACAGCATACATTAGTGACACTCTGCACTTC
---------+---------+---------+---------+---------+---------+
IleAspLysLeuThrGluIleThrThrAspThrAlaTyrIleSerAspThrLeuHisPhe 550                 570                 590
           .                   .                   .
TTGGATCCGAGCTACATAGTGGAGACATTCCAAAACTGCCCAAAACTGCAAACATTGTAT
```

FIG. 2A

```
                ----------+---------+---------+---------+---------+---------+
                LeuAspProSerTyrIleValGluThrPheGlnAsnCysProLysLeuGlnThrLeuTyr 610              630              650
                     .                .                .
                GCGACCTTAGTTCTCCCCGTTGAGGCAGCCTTCAAAATGGAAAGCACTCACCCGAACATA
                ----------+---------+---------+---------+---------+---------+
                AlaThrLeuValLeuProValGluAlaAlaPheLysMetGluSerThrHisProAsnIle 670              690              710
                     .                .                .
                TACAGCCTCAAATACTTCGGAGATGGTTTCCAGTATATACCAGGCAACCATGGTGGTGGA
                ----------+---------+---------+---------+---------+---------+
                TyrSerLeuLysTyrPheGlyAspGlyPheGlnTyrIleProGlyAsnHisGlyGlyGly 730              750              770
                     .                .                .
                GCGTACCATCATGAATTTGCTCATTTACAATGGCTCAAAGTGGGAAAGATCAAATGGAGG
                ----------+---------+---------+---------+---------+---------+
                AlaTyrHisHisGluPheAlaHisLeuGlnTrpLeuLysValGlyLysIleLysTrpArg 790              810              830
                     .                .                .
                GACCCCAAGGATAGCTTTCTCGGACATCTCAATTACACGACTGAGCAGGTTGAGATGCAC
                ----------+---------+---------+---------+---------+---------+
                AspProLysAspSerPheLeuGlyHisLeuAsnTyrThrThrGluGlnValGluMetHis 850              870              890
                     .                .                .
                ACAGTGACAGTGCAGTTGCAGGAATCGTTCGCGGCAAACCACTTGTACTGCATCAGGAGA
                ----------+---------+---------+---------+---------+---------+
                ThrValThrValGlnLeuGlnGluSerPheAlaAlaAsnHisLeuTyrCysIleArgArg 910              930              950
                     .                .                .
                GGAGATTTGCTCACACCGGAGGTGCGCACTTTTGGCCAACCTGACAGGTATGTGATTCCA
                ----------+---------+---------+---------+---------+---------+
                GlyAspLeuLeuThrProGluValArgThrPheGlyGlnProAspArgTyrValIlePro 970              990              1010
                     .                .                .
                CCACAGATCTTCCTCCCGAAAGTCCATAACTGCAAGAAGCCGATTCTTAAAAAAACTATG
                ----------+---------+---------+---------+---------+---------+
                ProGlnIlePheLeuProLysValHisAsnCysLysLysProIleLeuLysLysThrMet 1030             1050             1070
                     .                .                .
                ATGCAGCTCTTCTTGTATGTTAGGACAGTTAAGGTCGCAAAAAATTGTGACATTTTTGCC
                ----------+---------+---------+---------+---------+---------+
                MetGlnLeuPheLeuTyrValArgThrValLysValAlaLysAsnCysAspIlePheAla 1090             1110             1130
                     .                .                .
                AAAGTCAGACAATTAATTAAATCATCTGACCTGGACAAATATTCTGCTGTGGAACTGGTT
                ----------+---------+---------+---------+---------+---------+
                LysValArgGlnLeuIleLysSerSerAspLeuAspLysTyrSerAlaValGluLeuVal 1150             1170             1190
```

FIG. 2B

```
TACTTAGTAAGCTATATGGAGTTCCTTGCCGATCTACAAGCTACCACCTGCTTCTCAGAC
---------+---------+---------+---------+---------+---------+
TyrLeuValSerTyrMetGluPheLeuAlaAspLeuGlnAlaThrThrCysPheSerAsp 1210              1230              1250

ACACTTTCTGGTGGCTTACTAACAAAGACCCTTGCACCGGTGAGGGCTTGGATACAAGAG
---------+---------+---------+---------+---------+---------+
ThrLeuSerGlyGlyLeuLeuThrLysThrLeuAlaProValArgAlaTrpIleGlnGlu 1270              1290              1310

AAAAAGATGCAGCTGTTTGGTCTTGAGGACTACGCGAAGTTAGTCAAAGCAGTTGATTTC
---------+---------+---------+---------+---------+---------+
LysLysMetGlnLeuPheGlyLeuGluAspTyrAlaLysLeuValLysAlaValAspPhe 1330              1350              1370

CACCCAGTGGATTTTTCTTTTAAAGTTGAAACTTGGGACTTCAGATTCCACCCCTTGCAA
---------+---------+---------+---------+---------+---------+
HisProValAspPheSerPheLysValGluThrTrpAspPheArgPheHisProLeuGln 1390              1410              1430

GCGTGGAAAGCCTTCCGACCAAGGGAAGTGTCGGATGTAGAGGAAATGGAAAGTTTGTTC
---------+---------+---------+---------+---------+---------+
AlaTrpLysAlaPheArgProArgGluValSerAspValGluGluMetGluSerLeuPhe 1450              1470              1490

TCAGATGGGGACCTGCTTGACTGCTTCACAAGAATGCCAGCTTATGCAGTAAACGCAGAG
---------+---------+---------+---------+---------+---------+
SerAspGlyAspLeuLeuAspCysPheThrArgMetProAlaTyrAlaValAsnAlaGlu 1510              1530              1550

GAAGATTTAGCTACAATCAGGAAAACGCCCGAGATGGATGTCGGTCAAGAAGCCAAAGAA
---------+---------+---------+---------+---------+---------+
GluAspLeuAlaThrIleArgLysThrProGluMetAspValGlyGlnGluAlaLysGlu 1570              1590              1610

CCTGCAGGAGACAGAAATCAATACTTAAACCCTGCAGAAACTTTCCTCAACAAGCTCCAC
---------+---------+---------+---------+---------+---------+
ProAlaGlyAspArgAsnGlnTyrLeuAsnProAlaGluThrPheLeuAsnLysLeuHis 1630              1650              1670

AGGAAACACAGTAGGGAGGTGAAACATCAGGCCGTAAAGAAAGCTAAACGCCTAGCTGAA
---------+---------+---------+---------+---------+---------+
ArgLysHisSerArgGluValLysHisGlnAlaValLysLysAlaLysArgLeuAlaGlu 1690              1710              1730

ATCCAGGAGTCCATGAGAGCTGAGGGTGAGGCCGAACTAAATGAGATGAGCGGGGGCATG
---------+---------+---------+---------+---------+---------+
IleGlnGluSerMetArgAlaGluGlyGluAlaGluLeuAsnGluMetSerGlyGlyMet
```

FIG. 2C

```
                  1750                    1770                    1790
AGGGCAATACCTAGCAACGCAGAACTTCCAGCACGAACGATGCTAGACAAGAACTCACA
---------+---------+---------+---------+---------+---------+
ArgAlaIleProSerAsnAlaGluLeuProSerThrAsnAspAlaArgGlnGluLeuThr 1810                    1830                    1850
CTCCCAACCACTAAACCTGTCCCTGCAAGGTGGGAAGATGCTTCATTCACAGATTCTAGT
---------+---------+---------+---------+---------+---------+
LeuProThrThrLysProValProAlaArgTrpGluAspAlaSerPheThrAspSerSer 1870                    1890                    1910
GTGAAAGAGGAGCAAGTGAAACTCCCTGGAAAAGAAGCCGTTGAGACAGCGACGCAACAA
---------+---------+---------+---------+---------+---------+
ValLysGluGluGlnValLysLeuProGlyLysGluAlaValGluThrAlaThrGlnGln 1930                    1950                    1970
GTCATAGAAGGACTCCCTTGGAAACACTGGATTCCTCAACTAAATGCTGTTGGATTCAAG
---------+---------+---------+---------+---------+---------+
ValIleGluGlyLeuProTrpLysHisTrpIleProGlnLeuAsnAlaValGlyPheLys 1990                    2010                    2030
GCGCTGGAAATTCAGAGGGATAGGAGTGGGACAATGATCATGCCCATCACAGAAATGGTC
---------+---------+---------+---------+---------+---------+
AlaLeuGluIleGlnArgAspArgSerGlyThrMetIleMetProIleThrGluMetVal 2050                    2070                    2090
TCCGGGTTGGAAAAGAGGACTTCCCGGAAGGAACTCCAAAAGAGTTGGCACGAGAATTG
---------+---------+---------+---------+---------+---------+
SerGlyLeuGluLysGluAspPheProGluGlyThrProLysGluLeuAlaArgGluLeu

CTCGCTAAGAGCTC
------
LeuAla
```

FIG. 2D

Systemic levels of PVX in plants challenged with a 0.5 ug/ml inoculum

Legend:
- □ samsun (control)
- ○ 30205
- ● 30199
- ▲ 30219
- ✧ 29436

Y-axis: PVX antigen levels (ng/mg of fresh weight tissue)
X-axis: days post inoculation

FIG. 6

Systemic levels of PVX in plants challenged with a 5.0 ug/ml inoculum

Legend
- □ samsun (control)
- ○ 30205
- ● 30199
- ▲ 30219
- ✪ 29436

FIG. 7

```
              SspI
              ------
       TCATCAAAATATTTAGCAGCATTCCAGATTGGGTTCAATCAACAAGGTACGAGCCATATC
 6358  --+---------+---------+---------+---------+---------+-------  6417
       AGTAGTTTTATAAATCGTCGTAAGGTCTAACCCAAGTTAGTTGTTCCATGCTCGGTATAG

ACTTTATTCAAATTGGTATCGCCAAAACCAAGAAGGAACTCCCATCCTCAAAGGTTTGTA
 6418  --+---------+---------+---------+---------+---------+-------  6477
       TGAAATAAGTTTAACCATAGCGGTTTTGGTTCTTCCTTGAGGGTAGGAGTTTCCAAACAT

AGGAAGAATTCTCAGTCCAAAGCCTCAACAAGGTCAGGGTACAGAGTCTCCAAACCATTA
 6478  --+---------+---------+---------+---------+---------+-------  6537
       TCCTTCTTAAGAGTCAGGTTTCGGAGTTGTTCCAGTCCCATGTCTCAGAGGTTTGGTAAT

GCCAAAAGCTACAGGAGATCAATGAAGAATCTTCAATCAAAGTAAACTACTGTTCCAGCA
 6538  --+---------+---------+---------+---------+---------+-------  6597
       CGGTTTTCGATGTCCTCTAGTTACTTCTTAGAAGTTAGTTTCATTTGATGACAAGGTCGT

CATGCATCATGGTCAGTAAGTTTCAGAAAAAGACATCCACCGAAGACTTAAAGTTAGTGG
 6598  --+---------+---------+---------+---------+---------+-------  6657
       GTACGTAGTACCAGTCATTCAAAGTCTTTTTCTGTAGGTGGCTTCTGAATTTCAATCACC

GCATCTTTGAAAGTAATCTTGTCAACATCGAGCAGCTGGCTTGTGGGGACCAGACAAAAA
       GCCAAAAGCTACAGGAGATCAATGAAGAATCTTCAATCAAAGTAAACTACTGTTCCAGCA
 6538  --+---------+---------+---------+---------+---------+-------  6597
       CGGTTTTCGATGTCCTCTAGTTACTTCTTAGAAGTTAGTTTCATTTGATGACAAGGTCGT

CATGCATCATGGTCAGTAAGTTTCAGAAAAAGACATCCACCGAAGACTTAAAGTTAGTGG
 6598  --+---------+---------+---------+---------+---------+-------  6657
       GTACGTAGTACCAGTCATTCAAAGTCTTTTTCTGTAGGTGGCTTCTGAATTTCAATCACC

GCATCTTTGAAAGTAATCTTGTCAACATCGAGCAGCTGGCTTGTGGGGACCAGACAAAAA
 6658  --+---------+---------+---------+---------+---------+-------  6717
       CGTAGAAACTTTCATTAGAACAGTTGTAGCTCGTCGACCGAACACCCCTGGTCTGTTTTT

AGGAATGGTGCAGAATTGTTAGGCGCACCTACCAAAAGCATCTTTGCCTTTATTGCAAAG
 6718  --+---------+---------+---------+---------+---------+-------  6777
       TCCTTACCACGTCTTAACAATCCGCGTGGATGGTTTTCGTAGAAACGGAAATAACGTTTC

ATAAAGCAGATTCCTCTAGTACAAGTGGGGAACAAAATAACGTGGAAAGAGCTGTCCTG
 6778  --+---------+---------+---------+---------+---------+-------  6837
       TATTTCGTCTAAGGAGATCATGTTCACCCCTTGTTTTATTGCACCTTTTCTCGACAGGAC

ACAGCCCACTCACTAATGCGTATGACGAACGCAGTGACGACCACAAAAGAATTCCCTCTA
 6838  --+---------+---------+---------+---------+---------+-------  6897
       TGTCGGGTGAGTGATTACGCATACTGCTTGCGTCACTGCTGGTGTTTTCTTAAGGGAGAT
                                                              SspI
                                                              -----
       TATAAGAAGGCATTCATTCCCATTTGAAGGATCATCAGATACTAACCAATATTTCTC
 6898  --+---------+---------+---------+---------+---------+-----  6954
       ATATTCTTCCGTAAGTAAGGGTAAACTTCCTAGTAGTCTATGATTGGTTATAAAGAG
```

FIG. 12

```
         10                  30                  50
         .                   .                   .
GAAAACTAAACCATACACCACCAACACAACCAAACCCACCACGCCCAATTGTTACACACC
---------+---------+---------+---------+---------+---------+

70                  90                 110
         .                   .                   .
CGCTTGAAAAAGCAAGTCTGACAAATGGCCAAAGTGCGCGAGGTTTACCAATCCTTTACA
---------+---------+---------+---------+---------+---------+
                        MetAlaLysValArgGluValTyrGlnSerPheThr 130                 150                 170
         .                   .                   .
GACTCCACCACAAAAACTCTCATCCAAGATGAGGCTTATAGAAATATTCGTCCCATCATG
---------+---------+---------+---------+---------+---------+
AspSerThrThrLysThrLeuIleGlnAspGluAlaTyrArgAsnIleArgProIleMet 190                 210                 230
         .                   .                   .
GAAAAACATAAACTAGCTAACCCGTACGCTCAAACGGTTGAAGCGGCTAATGATCTAGAG
---------+---------+---------+---------+---------+---------+
GluLysHisLysLeuAlaAsnProTyrAlaGlnThrValGluAlaAlaAsnAspLeuGlu 250                 270                 290
         .                   .                   .
GGGTTCGGCATAGCCACCAATCCCTATAGCATTGAGTTGCATACACATGCAGCTGCTAAG
---------+---------+---------+---------+---------+---------+
GlyPheGlyIleAlaThrAsnProTyrSerIleGluLeuHisThrHisAlaAlaAlaLys 310                 330                 350
         .                   .                   .
ACCATAGAGAATAAACTTCTAGAGGTGCTTGGTTCCATCCTACCACAAGAACCTGTTACA
---------+---------+---------+---------+---------+---------+
ThrIleGluAsnLysLeuLeuGluValLeuGlySerIleLeuProGlnGluProValThr 370                 390                 410
         .                   .                   .
TTTATGTTCCTTAAACCCAGGAAGCTAAACTACATGAGAAGAAACCCGCGGATCAAGGAC
---------+---------+---------+---------+---------+---------+
PheMetPheLeuLysProArgLysLeuAsnTyrMetArgArgAsnProArgIleLysAsp 430                 450                 470
         .                   .                   .
ATTTTCCACAATGTTGCCATTGAACCGAGAGACGTAGCAAGGTACCCCAAGGAAACAATA
---------+---------+---------+---------+---------+---------+
IlePheHisAsnValAlaIleGluProArgAspValAlaArgTyrProLysGluThrIle 490                 510                 530
         .                   .                   .
ATTGACAAACTCACAGAGATCACAACAGACACAGCATACATTAGTGACACTCTGCACTTC
---------+---------+---------+---------+---------+---------+
IleAspLysLeuThrGluIleThrThrAspThrAlaTyrIleSerAspThrLeuHisPhe
```

FIG. 13A

```
          550                  570                 590
TTGGATCCGAGCTACATAGTGGAGACATTCCAAAACTGCCCAAAACTGCAAACATTGTAT
---------+---------+---------+---------+---------+---------+
LeuAspProSerTyrIleValGluThrPheGlnAsnCysProLysLeuGlnThrLeuTyr 610                  630                 650
GCGACCTTAGTTCTCCCCGTTGAGGCAGCCTTCAAAATGGAAAGCACTCACCCGAACATA
---------+---------+---------+---------+---------+---------+
AlaThrLeuValLeuProValGluAlaAlaPheLysMetGluSerThrHisProAsnIle 670                  690                 710
TACAGCCTCAAATACTTCGGAGATGGTTTCCAGTATATACCAGGCAACCATGGTGGTGGA
---------+---------+---------+---------+---------+---------+
TyrSerLeuLysTyrPheGlyAspGlyPheGlnTyrIleProGlyAsnHisGlyGlyGly 730                  750                 770
GCGTACCATCATGAATTTGCTCATTTACAATGGCTCAAAGTGGGAAAGATCAAATGGAGG
---------+---------+---------+---------+---------+---------+
AlaTyrHisHisGluPheAlaHisLeuGlnTrpLeuLysValGlyLysIleLysTrpArg 790                  810                 830
GACCCCAAGGATAGCTTTCTCGGACATCTCAATTACACGACTGAGCAGGTTGAGATGCAC
---------+---------+---------+---------+---------+---------+
AspProLysAspSerPheLeuGlyHisLeuAsnTyrThrThrGluGlnValGluMetHis 850                  870                 890
ACAGTGACAGTGCAGTTGCAGGAATCGTTCGCGGCAAACCACTTGTACTGCATCAGGAGA
---------+---------+---------+---------+---------+---------+
ThrValThrValGlnLeuGlnGluSerPheAlaAlaAsnHisLeuTyrCysIleArgArg 910                  930                 950
GGAGATTTGCTCACACCGGAGGTGCGCACTTTTGGCCAACCTGACAGGTATGTGATTCCA
---------+---------+---------+---------+---------+---------+
GlyAspLeuLeuThrProGluValArgThrPheGlyGlnProAspArgTyrValIlePro 970                  990                1010
CCACAGATCTTCCTCCCGAAAGTCCATAACTGCAAGAAGCCGATTCTTAAAAAAACTATG
---------+---------+---------+---------+---------+---------+
ProGlnIlePheLeuProLysValHisAsnCysLysLysProIleLeuLysLysThrMet 1030                 1050                1070
ATGCAGCTCTTCTTGTATGTTAGGACAGTTAAGGTCGCAAAAAATTGTGACATTTTTGCC
---------+---------+---------+---------+---------+---------+
MetGlnLeuPheLeuTyrValArgThrValLysValAlaLysAsnCysAspIlePheAla
```

FIG. 13B

```
          1090                1110                1130
AAAGTCAGACAATTAATTAAATCATCTGACCTGGACAAATATTCTGCTGTGGAACTGGTT
----------+---------+---------+---------+---------+---------+
LysValArgGlnLeuIleLysSerSerAspLeuAspLysTyrSerAlaValGluLeuVal 1150                1170                1190
TACTTAGTAAGCTATATGGAGTTCCTTGCCGATCTACAAGCTACCACCTGCTTCTCAGAC
----------+---------+---------+---------+---------+---------+
TyrLeuValSerTyrMetGluPheLeuAlaAspLeuGlnAlaThrThrCysPheSerAsp 1210                1230                1250
ACACTTTCTGGTGGCTTACTAACAAAGACCCTTGCACCGGTGAGGGCTTGGATACAAGAG
----------+---------+---------+---------+---------+---------+
ThrLeuSerGlyGlyLeuLeuThrLysThrLeuAlaProValArgAlaTrpIleGlnGlu 1270                1290                1310
AAAAAGATGCAGCTGTTTGGTCTTGAGGACTACGCGAAGTTAGTCAAAGCAGTTGATTTC
----------+---------+---------+---------+---------+---------+
LysLysMetGlnLeuPheGlyLeuGluAspTyrAlaLysLeuValLysAlaValAspPhe 1330                1350                1370
CACCCAGTGGATTTTTCTTTTAAAGTTGAAACTTGGGACTTCAGATTCCACCCCTTGCAA
----------+---------+---------+---------+---------+---------+
HisProValAspPheSerPheLysValGluThrTrpAspPheArgPheHisProLeuGln 1390                1410                1430
GCGTGGAAAGCCTTCCGACCAAGGGAAGTGTCGGATGTAGAGGAAATGGAAAGTTTGTTC
----------+---------+---------+---------+---------+---------+
AlaTrpLysAlaPheArgProArgGluValSerAspValGluGluMetGluSerLeuPhe 1450                1470                1490
TCAGATGGGGACCTGCTTGACTGCTTCACAAGAATGCCAGCTTATGCAGTAAACGCAGAG
----------+---------+---------+---------+---------+---------+
SerAspGlyAspLeuLeuAspCysPheThrArgMetProAlaTyrAlaValAsnAlaGlu 1510                1530                1550
GAAGATTTAGCTACAATCAGGAAAACGCCCGAGATGGATGTCGGTCAAGAAGCCAAAGAA
----------+---------+---------+---------+---------+---------+
GluAspLeuAlaThrIleArgLysThrProGluMetAspValGlyGlnGluAlaLysGlu 1570                1590                1610
CCTGCAGGAGACAGAAATCAATACTTAAACCCTGCAGAAACTTTCCTCAACAAGCTCCAC
----------+---------+---------+---------+---------+---------+
ProAlaGlyAspArgAsnGlnTyrLeuAsnProAlaGluThrPheLeuAsnLysLeuHis
```

FIG. 13C

```
         1630                  1650                  1670
AGGAAACACAGTAGGGAGGTGAAACATCAGGCCGTAAAGAAAGCTAAACGCCTAGCTGAA
---------+---------+---------+---------+---------+---------+
ArgLysHisSerArgGluValLysHisGlnAlaValLysLysAlaLysArgLeuAlaGlu 1690                  1710                  1730
ATCCAGGAGTCCATGAGAGCTGAGGGTGAGGCCGAACTAAATGAGATGAGCGGGGCATG
---------+---------+---------+---------+---------+---------+
IleGlnGluSerMetArgAlaGluGlyGluAlaGluLeuAsnGluMetSerGlyGlyMet 1750                  1770                  1790
AGGGCAATACCTAGCAACGCAGAACTTCCCAGCACGAACGATGCTAGACAAGAACTCACA
---------+---------+---------+---------+---------+---------+
ArgAlaIleProSerAsnAlaGluLeuProSerThrAsnAspAlaArgGlnGluLeuThr 1810                  1830                  1850
CTCCCAACCACTAAACCTGTCCCTGCAAGGTGGGAAGATGCTTCATTCACAGATTCTAGT
---------+---------+---------+---------+---------+---------+
LeuProThrThrLysProValProAlaArgTrpGluAspAlaSerPheThrAspSerSer 1870                  1890                  1910
GTGAAAGAGGAGCAAGTGAAACTCCCTGGAAAAGAAGCCGTTGAGACAGCGACGCAACAA
---------+---------+---------+---------+---------+---------+
ValLysGluGluGlnValLysLeuProGlyLysGluAlaValGluThrAlaThrGlnGln 1930                  1950                  1970
GTCATAGAAGGACTCCCTTGGAAACACTGGATTCCTCAACTAAATGCTGTTGGATTCAAG
---------+---------+---------+---------+---------+---------+
ValIleGluGlyLeuProTrpLysHisTrpIleProGlnLeuAsnAlaValGlyPheLys 1990                  2010                  2030
GCGCTGGAAATTCAGAGGGATAGGAGTGGGACAATGATCATGCCCATCACAGAAATGGTC
---------+---------+---------+---------+---------+---------+
AlaLeuGluIleGlnArgAspArgSerGlyThrMetIleMetProIleThrGluMetVal 2050                  2070                  2090
TCCGGGTTGGAAAAAGAGGACTTCCCGGAAGGAACTCCAAAAGAGTTGGCACGAGAATTG
---------+---------+---------+---------+---------+---------+
SerGlyLeuGluLysGluAspPheProGluGlyThrProLysGluLeuAlaArgGluLeu 2110                  2130                  2150
CTCGCTAAGAGCTCGCCCGGGGATCCAGCTTTCGTTCGTATCGGTTTCGACAACGTTCGT
---------+---------+---------+---------+---------+---------+
LeuAlaLysSerSerProGlyAspProAlaPheValArgIleGlyPheAspAsnValArg
```

FIG. 13D

```
              2170                    2190
               .           .           .           .
    CAAGTTCAATGCATCAGTTTCATTGCGCACACACCAGAATCCTACTGA
    ---------+----------+----------+----------+--------
    GlnValGlnCysIleSerPheIleAlaHisThrProGluSerTyrEnd
```

FIG. 13E

PLANTS RESISTANT TO INFECTION BY PVX

FIELD OF THE INVENTION

This is a continuation of co-pending application Ser. No. 07/804,862 filed Dec. 6, 1991, now abandoned which is a continuation-in-part of application Ser. No. 07/771,912 filed Oct. 4, 1991 now abandoned. This invention is related, in general, to plant genetic engineering and, more specifically, to a means and method for imparting resistance to a plant from viral infection using a gene encoding a non-structural viral protein.

BACKGROUND OF THE INVENTION

Many agriculturally important crops are susceptible to infection by plant viruses. These viruses can seriously damage a crop and drastically reduce its economic value to the grower. This eventually leads to a higher cost for the consumer. Attempts to control or prevent infection of a crop by a plant virus have been made, yet viral pathogens continue to be a significant problem in agriculture.

Potato virus X (PVX) is the type member of the potexvirus plant virus group. PVX is a positive-sense, single-stranded RNA virus that is surrounded by a repeating proteinaceous monomer, which is termed the coat protein (CP). The encapsidated virus has a flexous rod morphology, which is characteristic of the potexvirus group. PVX RNA resembles eucaryotic mRNA in that the 5' terminus is capped and the 3' end contains a poly A tail.

The PVX genomic RNA replicates through RNA intermediates in a DNA-independent fashion. PVX RNA has five open readings frames (ORFs). ORFs 1–5 have the potential for encoding proteins of 165, 22.5, 12, 8 and 25 kilodaltons (kDa), respectively. Except for ORF5, which encodes for the 25 kDa coat protein, the functions of ORFs 1–4 are not completely understood. ORF1 is the largest of the open reading frames and encompasses more than two thirds of the viral genome. ORF1 is proposed to encode a replicase protein by virtue of its sequence similarity to other known replicase genes. In particular, ORF1 contains several conserved motifs that are found in other replicase genes, such as the NTP binding domain and the GDD motif (Hodgman 1988). The NTP domain is a conserved 7–8 amino acid sequence that is found in many proteins, including replicases, ATPases and helicases. The function of the NTP domain is to bind and subsequently cleave a nucleotide triphosphate. The GDD domain is larger than the NTP domain and contains a glycine amino acid residue (G) followed by two aspartate amino acid residues (D). GDD domains are often found in replicase proteins and are believed to be involved in catalytic function.

The host range of PVX is extremely large. PVX infects at least 240 species in 16 plant families, although more than half of the species belong to members of the Solanaceae family, including potato, tobacco and tomato (Purcifull and Edwardson, 1981). Potato plants are particularly susceptible to infection by PVX. Infection by PVX of a potato crop results in a substantially reduced yield. Moreover, simultaneous infection by PVX and the potyvirus Potato virus Y (PVY) cause a devastating synergistic effect. A combined PVX and PVY infection can reduce yields as much as 90% (deBokx, 1986). Because most of the commercial potato cultivars are propagated vegetatively, maintaining virus-free lines is of critical importance to the potato grower.

PVX is a mechanically-transmitted virus. Healthy plants commonly become infected if they come in contact with PVX infected plants (Loughnance and Murphy, 1938; deBokx, 1972). PVX can also be spread by walking through a field, or by handling the plants. Infectious PVX has been detected on the fabric of trousers a month after they were worn during a walk among infected potato plants. In addition, small animals can also spread PVX; infectious PVX has been recovered from dog and rabbit fur a day after the animals had run among infected plants (Todd 1957). Because of the ease of transmission of PVX, potato growers must adhere to strict cultural practices to control PVX infection. These methods include isolating plants from sources of infection, wide spacing to avoid plant contact, and sterilization of cultivating and harvesting tools. Fields must also be visually inspected for morphological signs of infection. Plants showing visual signs of PVX infection are destroyed by the grower. Farmers plant "potato seeds," which are actually not true seeds, but rather pieces of potato tubers. Before "potato seeds" can be sold to the farmer, they must pass a rigorous series of tests to be certified virus free. PVX infection of "potato seeds" is a cause of seed de-certification.

It has previously been shown that expression of a plant virus capsid protein, which is termed the coat protein, in a plant can confer resistance to the homologous virus and to related viruses (Abel et al. 1986; Tumer et al. 1987: Cuozzo et al. 1988; Hemenway et al. 1988; Stark and Beachy 1989; Lawson et al. 1990; Kaniewski et al. 1990). In these studies, resistance to virus disease is defined as either reduced incidence of infection, delayed symptom development, reduced virus replication or viral antigen levels, or slower to no systemic virus movement. Expression of the virus coat protein in these transgenic plants is responsible for the observed effects in the reduction of virus disease by an as yet undetermined mechanism (Abel et al. 1986; van Dun et al. 1988).

This type of protection to viral infection is termed coat protein mediated protection.

A portion of the proposed replicase gene from tobacco mosaic virus (TMV) recently has been found to provide resistance against TMV when expressed in tobacco plants (Golemboski et al. 1990). In TMV, two proteins, the 183 kDa and 126 kDa proteins, have been speculated to be replicase components (Ishikawa et al. 1986). The 183 kDa protein is a readthrough product of the 126 kDa sequence. The 126 kDa protein contains the NTP binding motif.

The 183 kd protein contains both the NTP and GDD motifs. More specifically, the 54 kDa readthrough portion of the 183 kDa protein is the portion that contains the GDD motif. Thus, the 183 kd protein of TMV most resembles the PVX 165 kd protein. Golemboski et al. (1990) found that transgenic tobacco plants expressing the 54 kDa readthrough portion were protected against infection by TMV. They did not, however, observe protection in transgenic plants expressing the 126 kDa protein. Moreover, they did not report any protection data on plants expressing the 183 kd protein.

Others have conducted protection experiments with transgenic plants expressing components of non-structural viral proteins. For example, van Dun et al. (1988) analyzed protection in tobacco plants expressing either of two genes encoding proteins involved in the replication of alfalfa mosaic virus (AMV). These plants were transformed with RNAs 1 or 2 of AlMV, which encode proteins P1 and P2, respectively. The polypeptides encoded by these RNAs have amino acid homologies to other viral replicases, and both RNAs are known to be essential for replication. In contrast to the PVX ORF1, the NTP and GDD binding motifs for AlMV reside on different RNAs and consequently different proteins. In particular, P1 on RNA1 has homology to the NTP binding motif and P2 on RNA2 has homology to the GDD motif Plants expressing either RNA1 or RNA2 were not protected against infection by AIMV. In addition, plants expressing both RNAs 1 and 2 were likewise not protected against infection by AlMV (Taschner et al. 1991).

SUMMARY OF THE INVENTION

A cDNA sequence encoding ORF1 of the PVX genome has been prepared that provides resistance to infection by PVX in plants expressing the DNA sequence at a sufficient level. It is believed that ORF1 of the PVX genome functions as a replicase gene in PVX. The DNA sequence of ORF1 is inserted into the desired plant species, preferably potato or tomato, and expressed therein to confer resistance to PVX. The DNA sequence encoding the PVX replicase gene is 4455 nucleotides in length, including 84 nucleotides at the 5' end that serve as an untranslated leader sequence. The gene encodes a protein of 1457 amino acids.

In one embodiment of the present invention, a plant gene is provided which comprises a promoter that functions in plant cells to cause the production of an RNA sequence, a DNA sequence encoding a PVX replicase gene, and a 3' non-translated DNA sequence that functions in plants to cause the addition of polyadenylated ribonucleotides to the 3' end of the RNA sequence. This plant gene may be inserted into a plant to express the PVX replicase gene. A plant expressing the PVX replicase gene at a sufficient level exhibits resistance to PVX.

In an alternate embodiment of the present invention, a DNA sequence including nucleotides 1-2106 of the PVX replicase gene is provided. This DNA sequence may be inserted into a desired plant, preferably potato or tomato, to provide resistance to infection by PVX in plants expressing the DNA sequence at a sufficient level. This DNA sequence is referred to as a truncated PVX replicase gene.

A method for providing resistance to infection by PVX in plants of the Solanaceae family is also provided. The method comprises transforming cells of the Solanaceae plant with a DNA sequence encoding a PVX replicase gene and selecting transformed plants that express the PVX replicase gene at a level sufficient to render the plants resistant to infection by PVX.

In a further embodiment of the present invention, a plant gene comprising a modified transcriptional promoter from cauliflower mosaic virus (eCaMV35S), a small synthetic fragment of DNA that facilitates linking the promoter to the replicase gene, an 84 nucleotide leader sequence derived from the PVX replicase coding region, an isolated DNA sequence encoding a PVX replicase gene, an additional small synthetic fragment of DNA that facilitates linking the gene to a 3' termination signal, and a 3' non-translated region that encodes a polyadenylation signal is also provided. This gene can be inserted into a plant to confer high levels of resistance to PVX The present invention provides a PVX replicase cDNA sequence that, when expressed in a transgenic plant, provides a reduced to no incidence of infection by PVX, and a reduced or no viral antigen level in both inoculated and systemic leaves.

BRIEF DESCRIPTION OF THE DRAWINGS

FIG. 1 illustrates the cDNA sequence and the predicted amino acid sequence of a PVX genomic clone that includes the replicase gene sequence. The PVX genomic leader sequence is also shown positioned upstream of the replicase gene coding region.

FIG. 2 illustrates the cDNA sequence of a truncated PVX replicase gene and its predicted amino acid sequence.

FIG. 6 is a graph illustrating the systemic viral antigen level of tobacco plant lines expressing the PVX replicase protein and control lines.

FIG. 7 is a graph illustrating the systemic viral antigen level of tobacco plant lines expressing the PVX replicase protein and control lines.

FIG. 12 illustrates the DNA sequence of the full-length transcript promoter from figwort mosaic virus.

FIG. 13 illustrates the DNA sequence of the truncated PVX gene extended by 33 codons.

DESCRIPTION OF THE PREFERRED EMBODIMENTS

Figure 3:
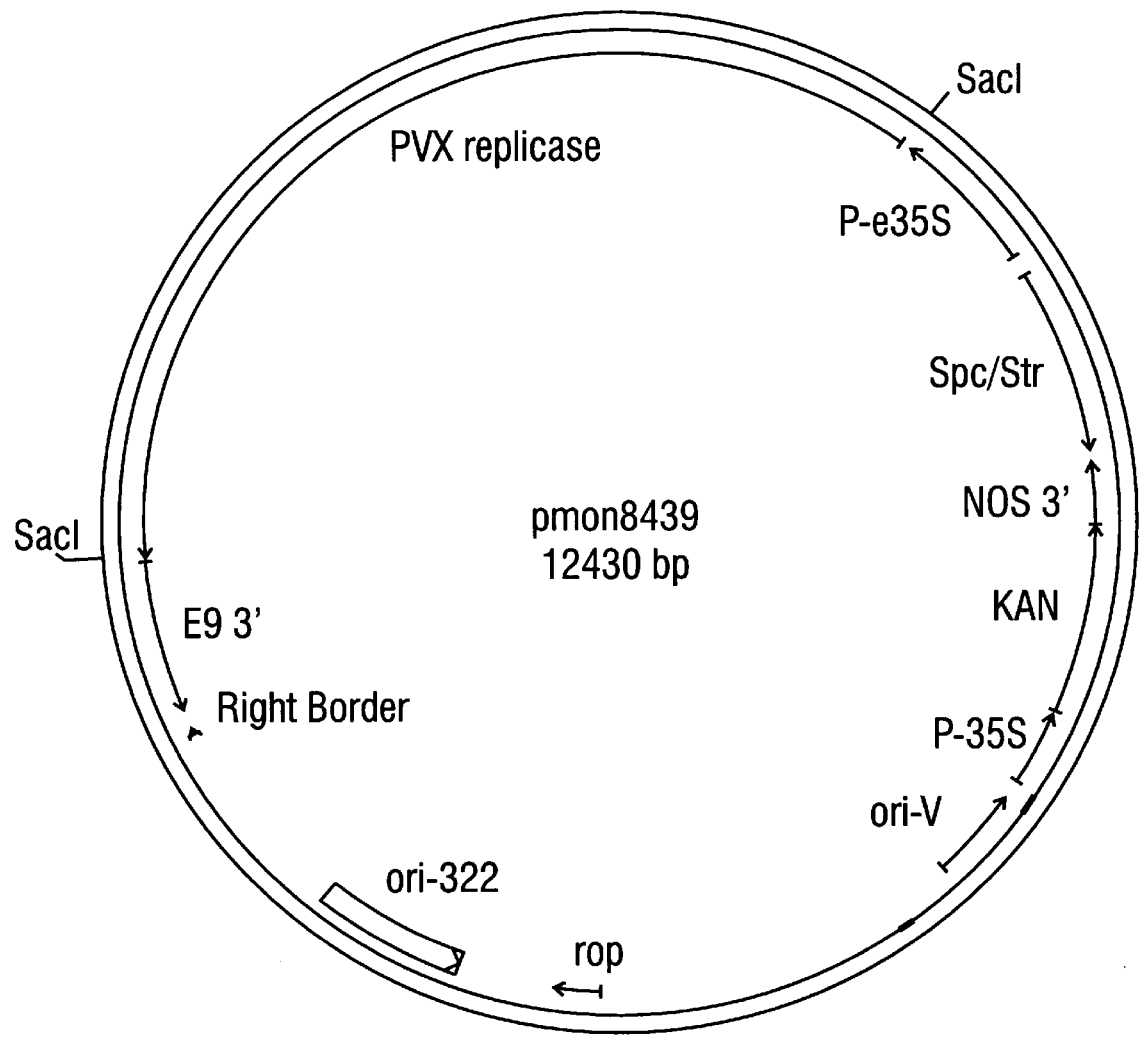
FIG. 3 illustrates a physical map of the plasmid pMON8439.
Figure 4:
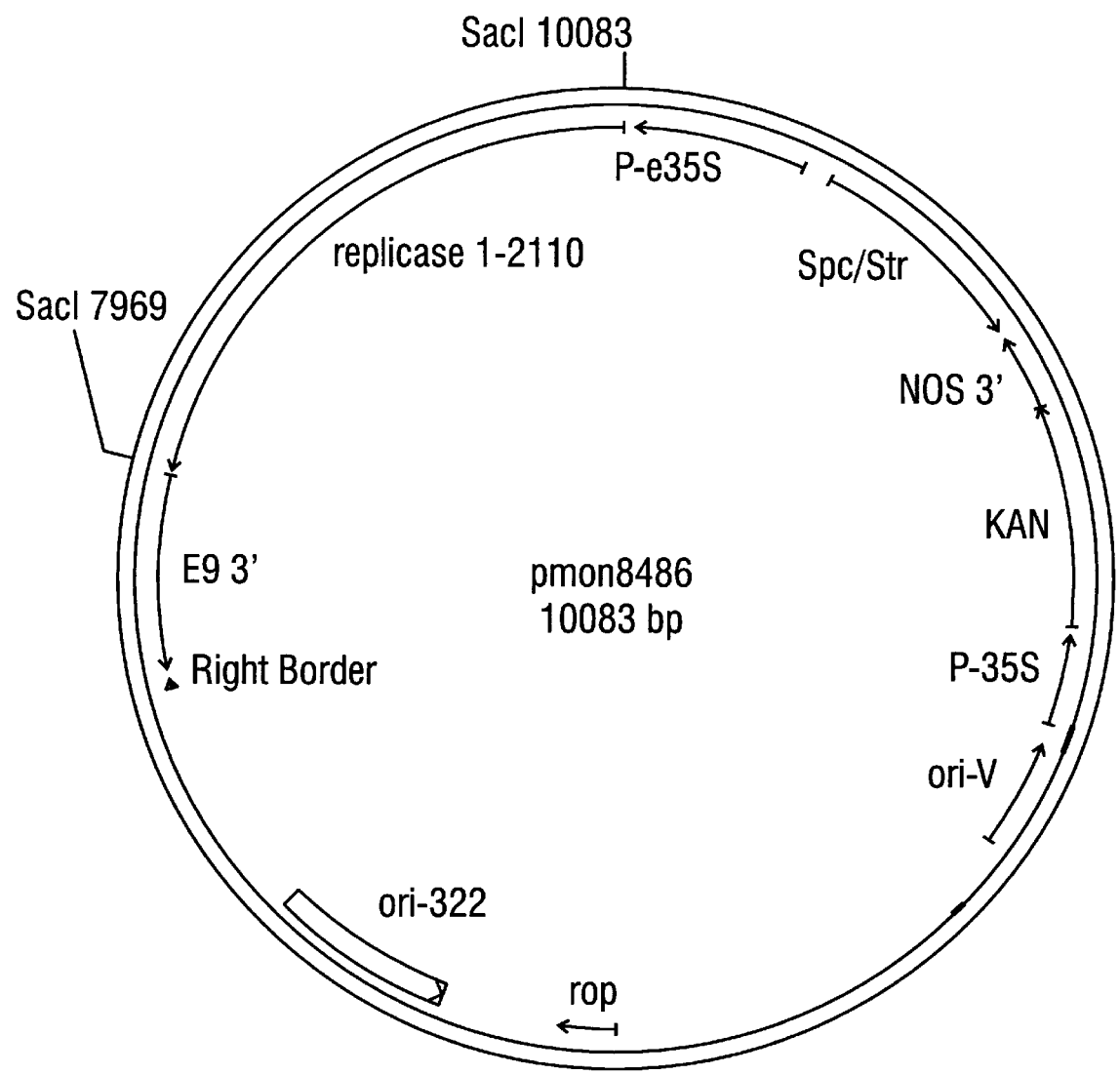
FIG. 4 illustrates a physical map of the plasmid of pMON8486.

The present invention provides a means and a method for conferring resistance in plants to infection from potato virus X (PVX). The resistance is provided by the expression in the plant of an isolated DNA sequence consisting essentially of nucleotides encoding a PVX replicase gene. A PVX replicase gene isolated from any of the various PVX strains or isolates can be used in the present invention. The corresponding replicase gene from different PVX strains is consistently the largest and most 5' ORF of the viral genome. The amino acid sequence of reported PVX replicase ORFs exhibit a high degree of similarity when compared to each other. The PVX replicase amino acid sequence disclosed herein (SEQ ID NO: 2) is 98% similar to the corresponding sequence of a Dutch strain of PVX replicase and the nucleotide sequences are 97% similar (Huisman et al. 1988). Replicase genes from two Russian PVX strains also are 98% identical at the amino acid level to the Dutch PVX strain (Skryahin et al. 1988). Thus, the similarity exhibited in the amino acid sequence of PVX replicases from PVX strains obtained from diverse geographic regions illustrates that any PVX strain or isolate could be used as the source of a PVX replicase gene for use in this invention.

For the purposes of illustrating the present invention, a field isolate of PVX obtained from Dr. Pete E. Thomas of the United States Department of Agriculture in Prosser, Wash. was used as the source of the replicase gene. The PVX genome was isolated from a cDNA library made from RNA recovered from purified PVX virions. The cDNA library was made from the PVX isolate obtained from Dr. Thomas.

A full-length PVX genomic clone was isolated and characterized from the cDNA library (Hemenway et al. 1990). When the full-length PVX clone is fused to the T7 bacteriophage transcriptional promoter, infectious PVX RNA can be synthesized in vitro, thus experimentally proving that the PVX cDNA retains the sequence in a formation necessary for biological activity. The CDNA sequence of the PVX replicase gene is 4455 nucleotides in length including a 5' non-translated leader sequence and is illustrated in FIG. 1. The replicase coding region begins at nucleotide position 85 and contains 4371 nucleotides or 1,457 codons. The PVX replicase coding region is designated as SEQ ID NO: 1. The deduced amino acid sequence is shown below the cDNA sequence in FIG. 1 and is identified as SEQ ID NO: 2. The first 84 nucleotides of the PVX genome are referred to as the genomic RNA leader sequence and are untranslated. The cDNA sequence of this untranslated leader sequence is also illustrated in FIG. 1 and is identified as SEQ ID NO: 3.

This PVX replicase cDNA sequence was the source used to produce the replicase DNA sequences of this invention. The nucleotide sequence of the replicase gene was modified at the 5' and 3' ends to facilitate cloning. DNA sequences were added by site-directed mutagenesis, using the method described by Kunkel (1985), to incorporate SacI sites into the DNA sequence. The oligonucleotide primers used to create the 5' and 3' SacI sites are, respectively, as follows:

5'-TATGGTTTAGTTTTCGAGCTCTATAGTGAGTCGTAT-3'
(SEQ ID NO: 4); and
5'-GGTAACTTAACGGGAGCTCTTAAAGAAAGTTTC-3'
(SEQ ID NO: 5).

The resulting sequence contained SacI restriction endonuclease recognition sites immediately upstream of position 1 and downstream of the stop codon at position 4455. The resulting SacI fragment that contained the PVX replicase gene was inserted into a plant transformation vector and used in experiments that tested its ability to confer resistance to infection by PVX in tobacco plants as further described in the examples to follow.

A truncated PVX replicase gene is prepared by inserting a stop codon and a SacI site between codons 674 and 675 of the full-length PVX replicase sequence to form a new 3' SacI site. The final 783 codons of the PVX replicase sequence are removed as a SacI—SacI fragment. The cDNA sequence and derived amino acid sequence of this truncated PVX replicase gene is illustrated in FIG. 2. The DNA sequence in FIG. 2 includes the 84 nucleotide PVX leader sequence and the 3' SacI site, but does not include a stop codon after codon 674. A truncated PVX replicase DNA sequence comprising nucleotides 85–2106 is designated as SEQ ID NO: 6 and the derived amino acid sequence of this truncated PVX replicase is designated SEQ ID NO: 7.

The replicase gene can be inserted into a suitable plant transformation vector for transformation into the desired plant species. Suitable plant transformation vectors include those derived from a Ti plasmid of *Agrobacterium tumefaciens*, in addition to those disclosed, for example, by Herrera-Estrella (1983), Bevan (1984), Klee (1985) and U. S. Pat. No. 4,940,838, issued to Schilperoort et al. A plant transformation vector preferably includes all of the necessary elements needed for transformation of plants or plant cells. Typical plant transformation vectors comprise selectable marker genes, one or both of the T-DNA borders, cloning sites, appropriate bacterial genes to facilitate identification of transconjugates, broad host-range replication and mobilization functions and other elements as desired.

The PVX replicase cDNA sequence is inserted into a plant transformation vector as a gene capable of being expressed in a plant. For the purposes of this invention, a "gene" is defined as an element or combination of elements that are capable of being expressed in a plant, either alone or in combination with other elements. Such a gene generally comprises, in the following order, a promoter that functions in plant cells, a 5' non-translated leader sequence, a DNA sequence coding for the desired protein, and a 3' non-translated region that functions in plants to cause the addition of polyadenylated ribonucleotides to the 3' end of the mRNA transcript. In this definition, each above described element is operationally coupled to the adjacent element. A plant gene comprising the above elements can be inserted by known, standard recombinant DNA methods into a plant transformation vector and other elements added to the vector when necessary. A plant transformation vector can be prepared that has all of the necessary elements for plant expression except the desired DNA coding region or portion thereof, which can readily be added to the vector by known methods.

Promoters that are known or found to cause transcription of DNA in plant cells can be used in the present invention. Such promoters can be obtained from a variety of sources such as plants or plant DNA viruses and include, but are not necessarily limited to, promoters isolated from the caulimovirus group, such as the cauliflower mosaic virus 19S and 35S (CaMV19S and CaMV35S) transcript promoters or the figwort mosaic virus full-length transcript promoter (FMV35S). The FMV35S promoter causes a high level of uniform expression of a coding region coupled thereto in most plant tissues. Other useful promoters include the enhanced CaMV35S promoter (eCaMV35S) as described by Kay et al. (1987) and the small subunit promoter of ribulose 1,5-bisphosphate carboxylase oxygenase (RUBISCO).

The promoter selected should be capable of causing sufficient expression of the PVX replicase gene to result in the production of an effective amount of the replicase RNA or replicase protein to render the plant cells and plants regenerated therefrom substantially resistant to infection by PVX. In particular, the enhanced CaMV35S promoter or the FMV35S promoter is useful in the present invention. The enhanced CaMV35S promoter causes sufficient levels of the replicase mRNA sequence to be produced in tobacco cells to yield tobacco plants that are highly resistant to infection by PVX.

The nucleotide sequence of an FMV35S promoter is provided in FIG. 12 and is designated SEQ ID NO: 9. Those skilled in the art will know that other promoters can be used with advantageous results in conjunction with the DNA sequences of the present invention and are within the scope of this invention.

The mRNA produced by the promoter contains both the coding region of the replicase gene and the 5' non-translated leader sequence. This non-translated leader sequence can be derived from any suitable source and can be specifically modified to increase translation of the mRNA. The 5' non-translated region can be obtained from the promoter selected to express the gene, the native 5' leader sequence of the gene or coding region to be expressed, viral RNAs, suitable eucaryotic genes, or a synthetic gene sequence. The present invention is not limited to the construct presented in the following examples, wherein the non-translated region is derived from 45 nucleotides from the eCaMV35S promoter, 6 nucleotides from the linker cassette, and 84 nucleotides of the native PVX leader sequence. The non-translated leader sequence can also be derived from an unrelated promoter or viral coding region as described.

The 3' non-translated region of the chimeric plant gene contains a polyadenylation signal that functions in plants to cause the addition of polyadenylated ribonucleotides to the 3' end of the mRNA. Examples of suitable 3' regions are the 3' transcribed, non-translated regions containing the polyadenylation signal of Agrobacterium tumor inducing (Ti) plasmid genes, such as the NOS gene, and plant genes such as the soybean storage protein genes and the small subunit promoter of the RUBISCO gene. An example of a preferred 3' region is that from the RUBISCO gene from pea (referred to as E9 3' in the figures) as described in the examples below.

The above described plant transformation vectors containing the PVX replicase gene may be used to transform plants of the Solanaceae family. In particular, infection by PVX is a persistent problem in potato and can infect tomato. An Agrobacterium-mediated transformation protocol is known to be effective in transforming members of the Solanaceae family. Other transformation techniques capable of inserting DNA into plant cells such as, but not limited to, electroporation, microprojectile or particle gun technology, and chemicals that increase free DNA uptake may also be used.

When an Agrobacterium mediated transformation is used, the desired transformation vector is mobilized into a suitable Agrobacterium strain. The ABI Agrobacterium strain is described for exemplary purposes. The desired transformation vector is mobilized into an ABI Agrobacterium strain by the triparental conjugation system using the helper plasmid pRK2013 (Ditta et al. 1980). The binary ABI strain is the chloramphenicol resistant derivative of *Agrobacterium tumefaciens* A208 which carries the disarmed Ti plasmid pTiC58 (Koncz and Schell 1986). The Ti plasmid does not carry the T-DNA phytohormone genes and the strain is therefore unable to cause crown gall disease. The disarmed Ti plasmid provides the trfA gene functions required for autonomous replication of the vector after conjugation into the ABI strain. When the plant tissue is incubated with the ABI::transformation vector conjugate, the vector is transferred to the plant cells by the vir functions encoded by the disarmed pTiC58 plasmid. The pTiC58 Ti plasmid does not transfer to the plant cells, but remains in the Agrobacterium. Either single- or double-border transformation vectors can be delivered to the plant by Agrobacterium. Single border vectors open at the right T-DNA border region, and the entire vector sequence is inserted into the host plant chromosome. The right border is lost during transfer and integration. In a double border vector, DNA between the right and left borders is inserted into the plant chromosome, thereby delivering only the chimeric genes of interest to the chromosome. The remainder of the vector, and the border sequences are lost during the transfer and integration.

Transformation and regeneration protocols for members of the Solanaceae family are known. In particular, various transformation and regeneration protocols for potato and tomato have been established. Exemplary protocols are described below.

For potato, two protocols are described below, but those skilled in the art know that modifications and optimization to the protocols can be made. Agrobacterium containing the desired plant transformation vector is grown overnight in 2 mls of LBSCK broth. LBSCK contains 10 g NaCl, 5 g yeast extract, 10 g Bacto-Tryptone, 50 mg spectinomycin, 25 mg chloramphenicol and 50 mg kanamycin in a 1 liter volume, pH 7.0. The following day, the bacteria are diluted 1:10 with MSO or until an OD (optical density) reading of 0.2–0.3 is established. MSO contains 4.4 g MX salts (Sigma Chemical Co., St. Louis, Mo.), 30 g sucrose and 2 ml $B_5$ vitamin (500×) in a 1 liter volume, pH 5.7. Leaves from the stem of potato plants that have been grown under sterile conditions for about three (3) weeks on PM media supplemented with 25 mg/l ascorbic acid are removed. PM media contains 4.4 g MS salts (Sigma Chemical Co., St. Louis, Mo.), 30 g sucrose, 0.17 g $NaH_2PO_4.H_2O$, 1 ml thiamine HCl and 0.1 g Inositol in a 1 liter volume, pH 6.0 and 0.2% Gelrite agar. The stems are placed on a vegetable slicer (~30–50 at a time) and cut into 3–5 mm segments. These stem explants are inoculated for 15 minutes with the diluted bacteria. Approximately 20 mls of bacterial solution is used per 1000 stem explants. The bacterial solution is removed by aspiration and the explants placed onto prepared co-culture plates. The co-culture plates contain 1/10 MSO with 1.5 mls of TxD cells overlayed with wetted filter paper. Approximately 50 explants are placed on each plate.

After a two (2) day co-culture period, explants are placed onto callus induction plates containing MSO plus 0.5 mg/l ZR (Zeatin riboside), 10 mg/l $AgNO_3$ and 0.1 mg/l NAA (naphthaleneacetic acid) for four (4) weeks. These plates also contain 100 mg/l kanamycin to select for transformed cells. After four (4) weeks, explants that exhibit growth in the presence of kanamycin are placed on shoot induction media which contains MSO plus 5.0 mg/l ZR, 10 mg/l $AgNO_3$ and 0.3 mg/l $GA_3$ (gibberellic acid) and 100 mg/l kanamycin for further selection. Shoots typically begin to appear at about six (6) weeks. The plants are then placed in sundae cups with PM media and allowed to grow for approximately 2 weeks. Plants are placed into soil, hardened off, and analyzed to verify transformation by assaying for the presence of a protein which confers resistance to the antibiotic kanamycin to the plant. If the plant is positive for expression of the protein, the plant is kept for further study and maintained in tissue culture.

Alternately, the explants may be placed on callus induction plates containing MSO plus 3.0 mg/l BA (6 benzylaminopurine) and 0.01 mg/l NAA for four (4) weeks with 100 mg/l kanamycin for selection. For shoot induction, the explants are placed on MSO plus 0.3 mg/l $GA_3$ only and 100 mg/ml kanamycin for selection. Shoots begin to appear at about 8 weeks. Shoots are recallused on MSP-5 with 200 mg/ml kanamycin and assayed in two weeks. MSP-5 contains 4.4 g MS salts (Sigma), 5 ml SLLX vitamins (200×), 30 g sucrose, 2.25 ml BAP, 0.186 ml NAA in 1 liter, pH 5.6 and 0.2% Gelrite agar.

After the potato plant has been transformed and after transformed callus has been identified, the transformed callus tissue is regenerated into whole plants. Any known method of regeneration of potato plants can be used in this invention.

For tomato, the transformation protocol described in McCormick et al. (1986) can generally be used. In particular, cotyledons are obtained from 7–8 day old seedlings. The seeds are surface sterilized for 20 minutes in 30% Clorox bleach and are germinated in Plantcons boxes on Davis germination media. Davis germination media is comprised of 4.3 g/l MS salts, 20 g/l sucrose and 10 mls/l Nitsch vitamins, pH5.8. The Nitsch vitamin solution is comprised of 100 mg/l myo-inositol, 5 mg/l nicotinic acid, 0.5 mg/l pyridoxine HCl, 0.5 mg/l thiamine HCl, 0.05 mg/l folic acid, 0.05 mg/l biotin, 2 mg/l glycine. The seeds are allowed to germinate for 7–8 days in the growth chamber at 25° C., 40% humidity under cool white lights with an intensity of 80 einsteins $m^{-2}s^{-1}$. The photoperiod is 16 hours of light and 8 hours of dark.

Once germination has occurred, the cotyledons are explanted using a #15 feather blade by cutting away the apical meristem and the hypocotyl to create a rectangular explant. These cuts at the short ends of the germinating cotyledon increase the surface area for infection. The explants are bathed in sterile Davis regeneration liquid to prevent desiccation. Davis regeneration media is composed of 1×MS salts, 3% sucrose, 1×Nitsch vitamins, 2.0 mg/l zeatin, pH 5.8. This solution is autoclaved with 0.8% Noble Agar.

The cotyledons are pre-cultured on "feeder plates" composed of media containing no antibiotics. The media is composed of 4.3 g/l MS salts, 30 g/l sucrose, 0.1 g/l myo-inositol, 0.2 g/l $KH_2PO_4$, 1.45 mls/l of a 0.9 mg/ml solution of thiamine HCl, 0.2 mls of a 0.5 mg/ml solution of kinetin and 0.1 ml of a 0.2 mg/ml solution of 2,4 D, this solution is adjusted to pH 6.0 with KOH. These plates are overlaid with 1.5–2.0 mls of tobacco suspension cells (TXD's) and a sterile Whatman filter which is soaked in 2COO5K media. 2COO5K media is composed of 4.3 g/l Gibco MS salt mixture, 1 ml B5 vitamins (1000×stock), 30 g/l sucrose, 2 ml/l PCPA from 2 mg/ml stock, and 10 μl/l kinetin from 0.5 mg/ml stock. The cotyledons are cultured for 1 day in a growth chamber at 25° C. under cool white lights with a light intensity of 40–50 einsteins $m^{-2}s^{-1}$ with a continuous light photoperiod.

Cotyledons are then inoculated with a log phase solution of Agrobacterium containing the desired transgenic gene. The concentration of the Agrobacterium is approximately $5 \times 10^8$ cells/ml. The cotyledons are allowed to soak in the bacterial solution for six minutes and are then blotted to remove excess solution on sterile Whatman filter disks and are subsequently replaced to the original feeder plate where they are allowed to co-culture for 2 days. After the two days, cotyledons are transferred to selection plates containing Davis regeneration media with 2 mg/l zeatin riboside, 500 μg/ml carbenicillin, and 100 μg/ml kanamycin. After 2–3 weeks, cotyledons with callus and/or shoot formation are transferred to fresh Davis regeneration plates containing carbenicillin and kanamycin at the same levels. The experiment is scored for transformants at this time. The callus tissue is subcultured at regular 3 week intervals and any abnormal structures are trimmed so that the developing shoot buds will continue to regenerate. Shoots develop within 3–4 months.

Once shoots develop, they are excised cleanly from callus tissue and are planted on rooting selection plates. These plates contain 0.5×MSO containing 50 μ/ml kanamycin and 500 μg/ml carbenicillin. These shoots form roots on the selection media within two weeks. If no shoots appear after 2 weeks, shoots are trimmed and replanted on the selection media. Shoot cultures are incubated in percivals at a temperature of 22° C. Shoots with roots are then potted when roots are about 2 cm in length. The plants are hardened off in a growth chamber at 21° C. with a photoperiod of 18 hours light and 6 hours dark for 2–3 weeks prior to transfer to a greenhouse. In the greenhouse, the plants are grown at a temperature of 26° C. during the day and 21° C. during the night. The photoperiod is 13 hours light and 11 hours dark and allowed to mature.

The following examples are provided to elucidate better the practice of the present invention and should not be interpreted in any way to limit the scope of the present invention. Those skilled in the art will recognize that various modifications can be made to the methods and genes described herein while not departing from the spirit and scope of the present invention.

EXAMPLE 1

Figure 5:
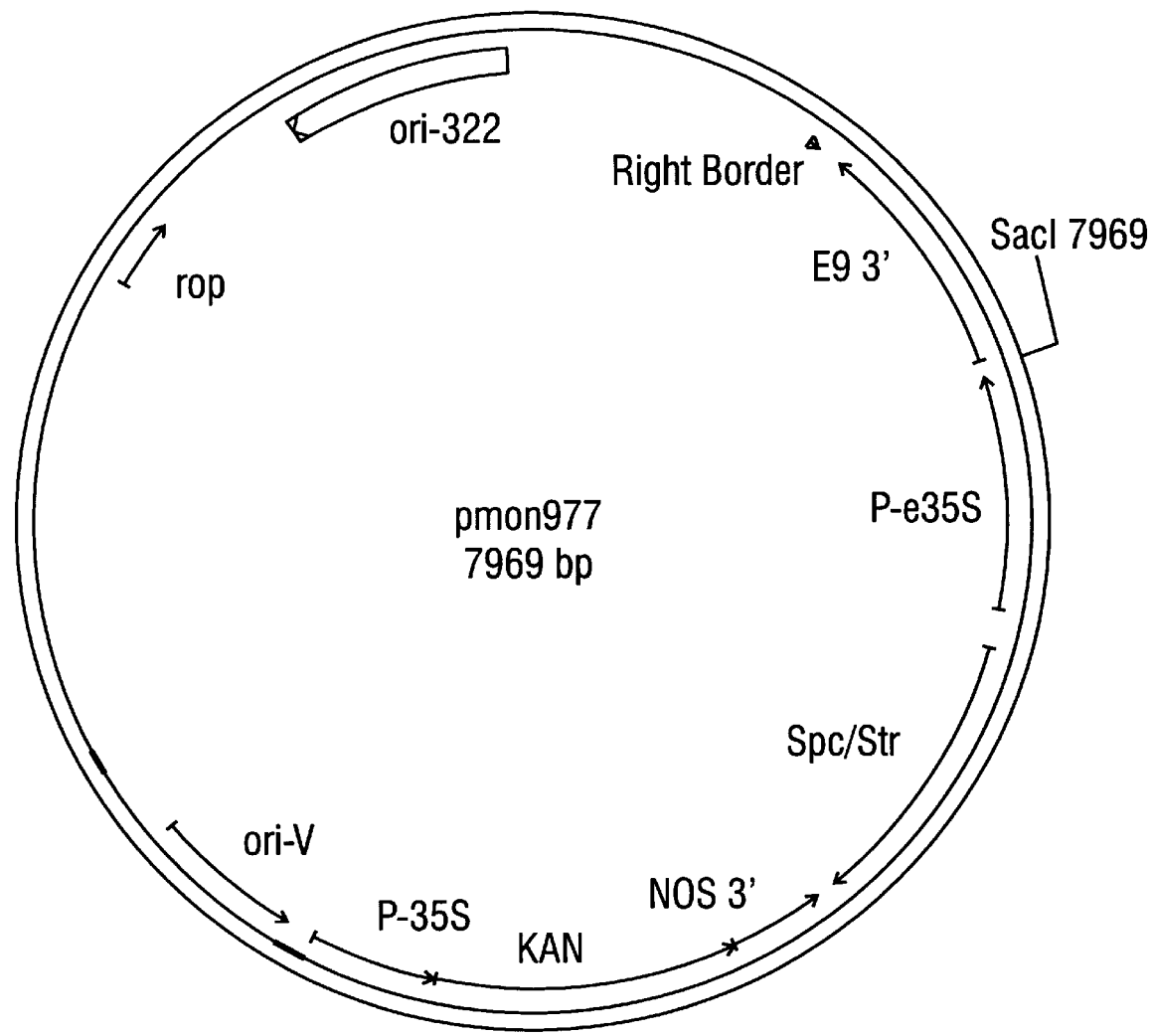
FIG. 5 illustrates a physical map of the plasmid pMON977.
Figure 8:
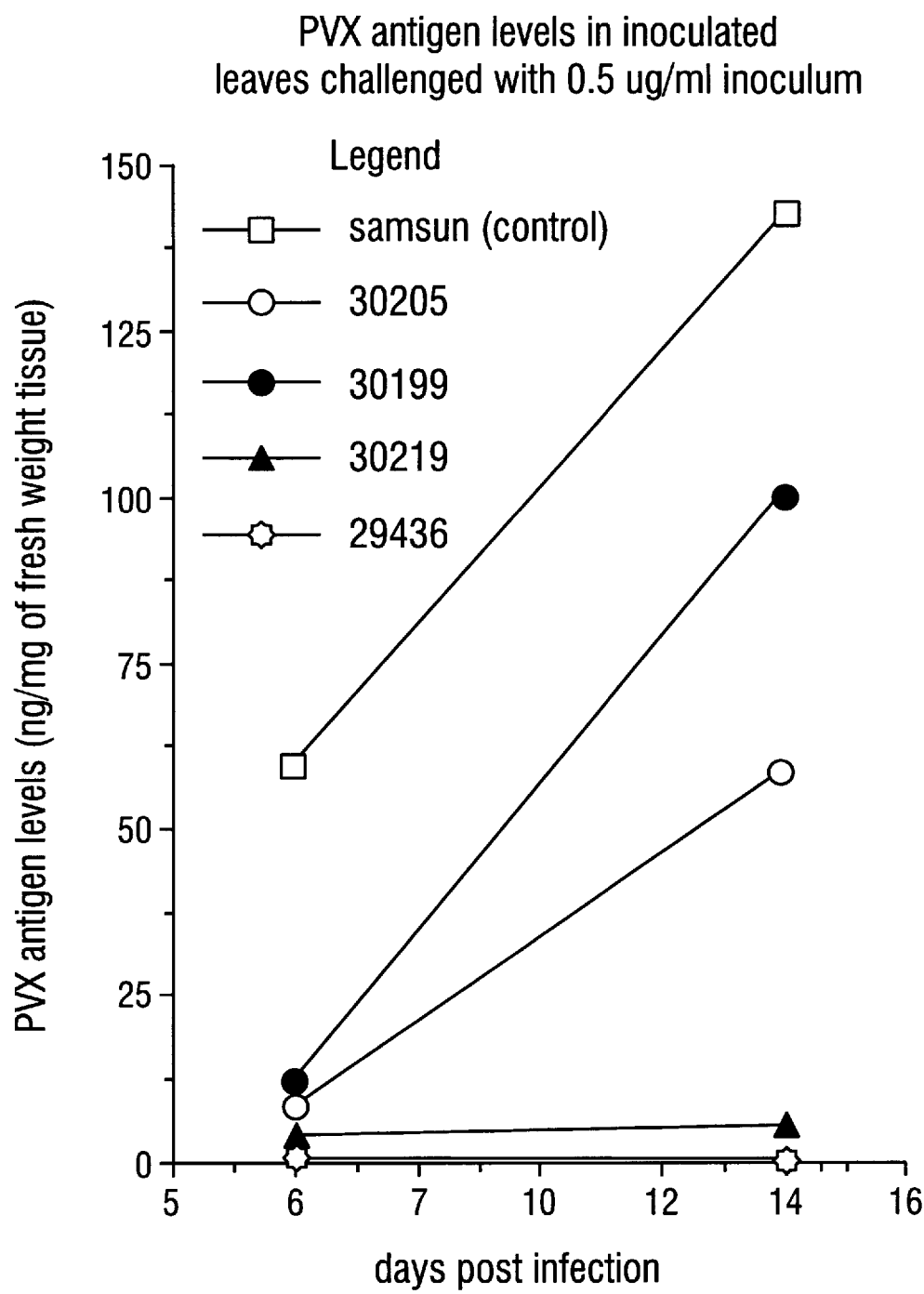
FIG. 8 is a graph illustrating the viral antigen level in inoculated leaves from tobacco plant lines expressing the PVX replicase protein and control lines.
Figure 9:
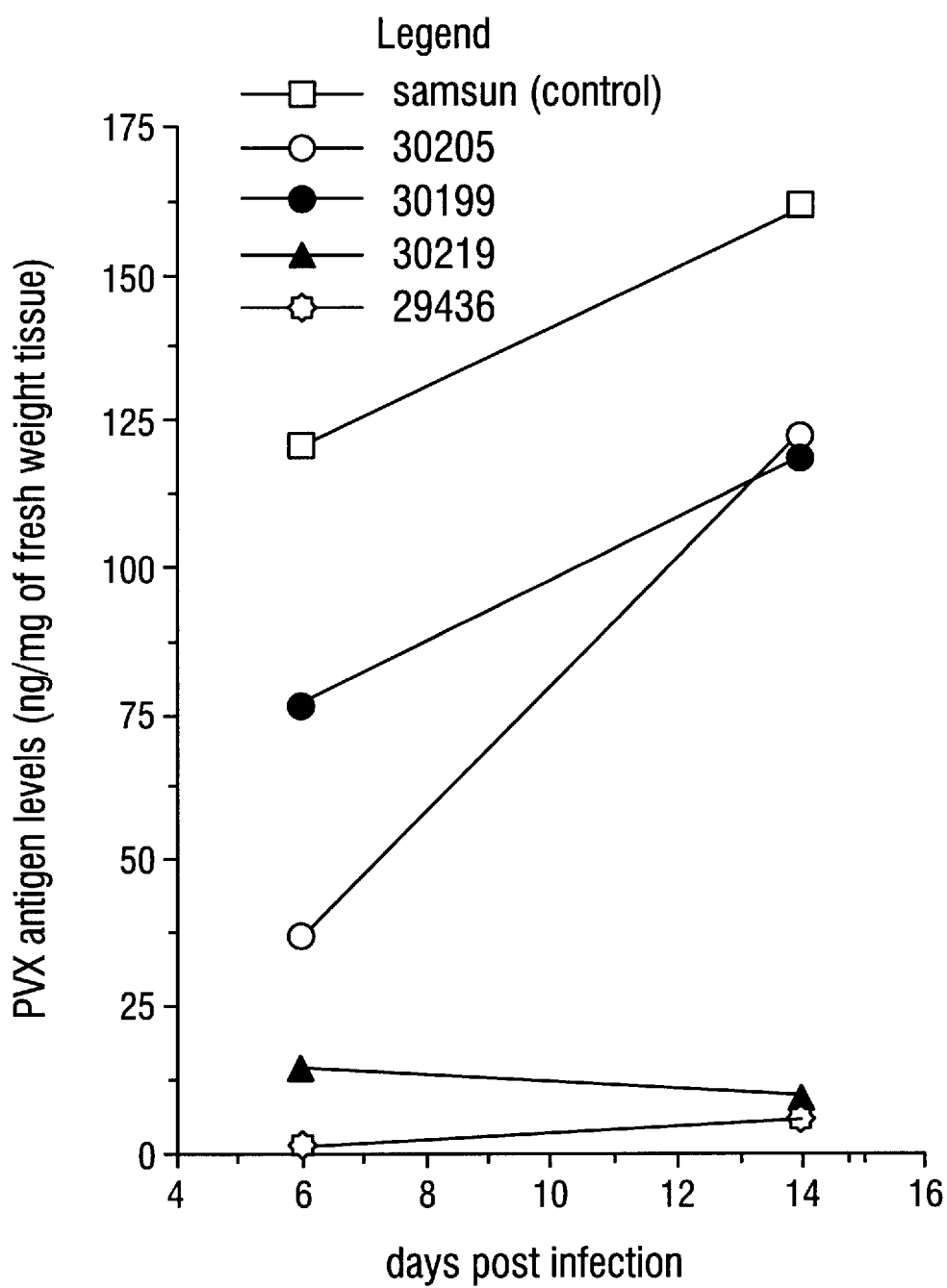
FIG. 9 is a graph illustrating the viral antigen level in inoculated leaves from tobacco plant lines expressing the PVX replicase protein and control lines.

The DNA coding sequence for the PVX replicase gene (SEQ ID NO: 1) was engineered into pMON977, which is a single border plant transformation vector, to study its ability to confer resistance to PVX in plants expressing the replicase gene. A physical map of pMON977 is shown in FIG. 5. The resulting vector containing the PVX replicase gene is pMON8439, and is illustrated in FIG. 3.

Plasmid pMON8439 contains the following DNA segments. Starting near the bottom of FIG. 3 is the origin of bacterial replication for maintenance in *E. coli* (ori-322) and includes the bom site for conjugational transfer into *Agrobacterium tumefaciens* cells. Moving in a counter-clockwise direction, next is the ori-V, which is the vegetative origin of replication (Stalker et al. 1981). Next is the chimeric gene used as the selectable marker. The chimera includes 0.35 kilobase (kb) of cauliflower mosaic virus 35S promoter (P-35S) (Odell et al. 1985), a 0.83 kb neomycin phosphotransferase type II gene (KAN), and a 0.25 kb 3' non-translated region of the nopaline synthase gene (NOS 3') (Fraley et al. 1983). Next is the 0.93 kb fragment isolated from transposon Tn7 that encodes the bacterial spectinomycin/streptomycin resistance (Spc/Str), which is a determinant for selection in *E. coli* and *Agrobacterium tumefaciens* (Fling et al. 1985). The next sequence contains a second chimeric gene, including PVX replicase. A 0.64 kb DNA sequence containing the enhanced CaMV35S promoter functions as the transcriptional promoter for the PVX replicase coding region (SEQ ID NO: 1). The chimeric gene ends with the 0.65 kb of the E9 3' region from the pea small subunit RUBISCO gene (Coruzzi et al. 1984).

Prior to transformation, *E. coli* containing pMON8439 were mated into Agrobacterium ABI by a triparental mating with the helper plasmid pRK2013 (Ditta et al. 1980). ABI is the A208 *Agrobacterium tumefaciens* strain carrying the disarmed pTiC58 plasmid pMP90RK (Koncz and Schell, 1986). The disarmed Ti plasmid provides the trfA gene functions that are required for autonomous replication of the pMON vector after the conjugation into the ABI strain. When plant tissue is incubated with the ABI::pMON conjugate, the vector is transferred to the plant cells by the vir functions encoded by the disarmed pMP90RK Ti plasmid. Agrobacterium were grown 30 hours in LB media (10 g tryptone, 5 g yeast extract and 5 g NaCl per liter) with 25 μg/ml chloramphenicol and 50 mg kanamycin at 30° C. *E. coli* containing pRK2013 were grown overnight in kanamycin (50 μg/ml). This culture was started with several colonies. *E. coli* with pMON8439 were grown in LB with 75 μg/ml spectinomycin. After all of the cultures were grown, 4 ml of LB was added to a tube with 100 μl each of Agrobacterium ABI, pRK2013, and pMON8439. This mixture was centrifuged in a microfuge for 5 minutes and the supernatant fraction decanted. The pellet fraction was resuspended in the remaining liquid, and an aliquot was pipetted into the center of an LB plate. After overnight growth at 30° C., an aliquot of cells from this plate was streaked onto an LB plate supplemented with 75 μg/ml spectinomycin, 50 μg/ml kanamycin and 25 μ/ml chloramphenicol.

After 24–48 hours at 300° C., the plate from the triparental mating of pMON8439, pRK2013 and Agrobacterium ABI contained colonies, while the control plate from the mating of pMON8439 and ABI (without pRK2013, which is required for mobilization) did not contain colonies. After the triparental mating, 4 colonies were selected from the former plate, inoculated into a liquid culture of LB supplemented with 75 μg/ml spectinomycin, 50 μg/ml kanamycin and 25 μg/ml chloramphenicol and grown at 300° C. The presence of the PVX replicase gene was shown by DNA blot analysis. One of the cultures verified to contain PVX replicase was used for transformation of tobacco by the leaf disk transformation protocol.

The tobacco leaf disk transformation protocol uses healthy leaf tissue approximately one month old (Horsch et al. 1985). After a 15- to 20-minute surface sterilization of the leaves with a 10% v/v Clorox plus a surfactant, the leaves were rinsed 3 times in sterile water. Using a sterile paper punch, leaf discs were punched and placed upside down on MS104 media (4.3 g/l MS salts, 30 g/l sucrose, B5 vitamins, 0.1 mg/l NAA and 1.0 mg/l BA) for a 1 day preculture. Discs were then inoculated with an overnight culture of Agrobacterium ABI: pMON8439 that was diluted 1:5. The inoculation was done by placing the discs in centrifuge tubes with the culture. After 30 to 60 seconds, the liquid was drained off and the discs were blotted between sterile filter paper. Discs were then placed upside down on MS104 feeder plates with a filter disc to co-culture.

After 2–3 days of co-culture, discs were transferred, still upside down, to selection plates with MS104 media. After 2- to 3-weeks, calli formed, and individual clumps were separated from the leaf discs. Shoots were cleanly cut from the callus when they were large enough to distinguish from stems. The shoots were placed on hormone-free rooting media (MSO: MS salts, 30 g/l sucrose, and B5 vitamins) with selection. Roots formed in 1–2 weeks. Rooted shoots were placed in soil and were kept in a high humidity environment (e.g. plastic containers or bags). Shoots were hardened off by gradually exposing them to ambient humidity conditions.

Transgenic lines derived from transformation with pMON8439 were assayed by RNA blot analysis (Thomas, 1980) to determine the presence of PVX replicase mRNA corresponding to the predicted mRNA transcript expected from pMON8439. Transgenic plants with detectable PVX replicase RNA were allowed to self-fertilize and set seed. F1 progeny germinated from this seed were tested for resistance to infection by PVX. Prior to infection, the plants were screened by ELISA for the presence of neomycin phosphotransferase (NPTII). This test was essential because DNA inserted by *Agrobacterium mediated* transformation will segregate in the next generation in a Mendelian fashion. Thus, if one copy of the transferable region of plasmid pMON8439 is incorporated into plant genome, the F1 progeny of such an event will display a 3:1 phenotypic segregation for the transgenic trait (PVX replicase) and the selectable marker (NPNII).

Twenty plants that contained NPTII were selected from each plant line for PVX infection experiments. Non-transformed tobacco (Nicotiana tabacum var. samsun) was used as the control line. Plants were grown and tested in an environmentally controlled growth chamber with the following parameters: a 15 hour photoperiod (250 μEinsteins) at 250° C., followed by 9 hours of darkness at 22° C. Throughout the experiment, the chamber was held at 50% relative humidity. Ten of the twenty plants were inoculated with a low concentration of PVX (0.5 μg/ml), and the remaining ten plants were inoculated with a high concentration of PVX (5.0 μg/ml). Only young plants, containing 5–6 small leaves, were inoculated. 50 μl of inoculum, in a 0.1M, pH 7.0 phosphate buffer, was lightly rubbed onto 2 leaves per plant that were pretreated with carborundum, which is a fine abrasive. This abrasive application slightly wounds the young leaves, and provides an enhanced opportunity for viral infection. Data from four replicase lines are shown in Table 1 (lines 29436, 30199, 30205 and 30219). Plants were monitored daily for visual signs of infection. At six days post infection (dpi), lesions of the inoculated leaves were counted (Table 1).

TABLE 1

| line | 0.5 μg/ml inoculum | 5.0 μg/ml inoculum |
|---|---|---|
| samsun | 13.3 (19.7) | 35.7 (24.4) |
| 29436 | 0.05† (0.22) | 0.15§ (0.37) |
| 30219 | 0.61† (1.0) | 6.3§ (7.2) |
| 30199 | 2.1† (2.8) | 17.2† (16) |
| 30205 | 1.5† (3.4) | 8.5§ (8) |

The mean number of lesions observed are shown for each of two inoculums per line. Sample standard deviations are shown parenthetically following the mean. The mean lesion counts from the transgenic lines were statistically compared to the control samsun line using the Student's t test, using a pooled estimate of variation. The † symbol indicates a statistically significant difference from the control at p=0.05; § indicates a statistically significant difference from the control at p=0.01.

To estimate virus levels in the inoculated and systemic leaves, a #8 sized cork borer, which yields circular samples weighing approximately 50 mg, was used to sample the plants. Inoculated leaves were sampled twice, at 6 and 14 dpi, and the second upper leaf was sampled three times, at 6, 11 and 14 dpi. Two #8 sized discs were taken at each sampling. Sampling the upper leaves estimates the extent of systemic infection. These leaf discs were analyzed for the presence of PVX coat protein (CP) antigen by ELISA. This assay is a quantitative estimation of virus titer. The results of this test are shown in FIGS. 6–9.

FIG. 6 illustrates graphically the systemic levels of PVX in plants challenged with 0.5 μg/ml of PVX viral inoculum. FIG. 7 illustrates graphically the systemic levels of PVX in plants challenged with a 5.0 μg/ml PVX viral inoculum. FIG. 8 illustrates graphically the PVX antigen levels in inoculated leaves challenged with 0.5 μg/ml PVX viral inoculum. FIG. 9 illustrates graphically PVX antigen levels in inoculated leaves challenged with 5.0 μg/ml PVX viral inoculum. In FIGS. 6 and 7, the number of days post inoculation is plotted vs. PVX CP antigen levels measured in ng/mg fresh weight of tissue. In FIGS. 8 and 9, the number of days post infection is plotted vs. PVX CP antigen levels measured in ng/mg of fresh weight of tissue. As can be seen in FIGS. 6–9, the samsun control line became highly infected at each inoculum concentration, both in the inoculated and systemic leaves. This is a typical PVX infection, where the virus can accumulate to extremely high levels. At 14 dpi (days post infection), approximately 15% of the extractable protein in the systemic samsun leaves is PVX CP. In contrast, the best tobacco line expressing the PVX replicase gene, 29436, has been shown in a separate protection test to contain a 23,000-fold reduction in PVX levels compared to the samsun control. The tobacco lines expressing PVX replicase as shown in FIGS. 6–9 display two types of responses to PVX infection. For example, lines 29436 and 30219 consistently show a very low level of PVX antigen at both inoculum concentrations in both the inoculated and upper leaves assayed. Lines 30205 and 30199 show a different type of resistance. While the PVX antigen level in these lines is consistently lower than the samsun control, this type of resistance is best described as a delay in virus infection.

EXAMPLE 2

A truncated PVX replicase gene, containing the native 84 nucleotide leader sequence (SEQ ID NO: 3) and the first 674 codons (SEQ ID NO: 6) is created by site-directed mutagenesis (Kunkel, 1985). The oligonucleotide primer necessary to create this truncated version of the PVX replicase allows for the insertion of a TAA stop codon and a SacI restriction endonuclease site between codons 674 and 675 (between an alanine and methionine). The oligonucleotide primer is: 5'-GAATTGCTCGCTTAAGAGCTCATGAACAGAAGCC-3' (SEQ ID NO: 8).

Plasmid pMON8486 was created to test whether a portion of the PVX replicase gene could impart resistance to PVX infection when expressed in a plant. The oligonucleotide primer used to create this truncated version of the PVX replicase gene contains a SacI restriction endonuclease site, which facilitates cloning into a plant transformation vector. The oligonucleotide primer used was: 5'-GAATTGCTCGCTAAGAGCTCATGAACAGAAGCC-3' (SEQ ID NO: 10)

Figure 10:
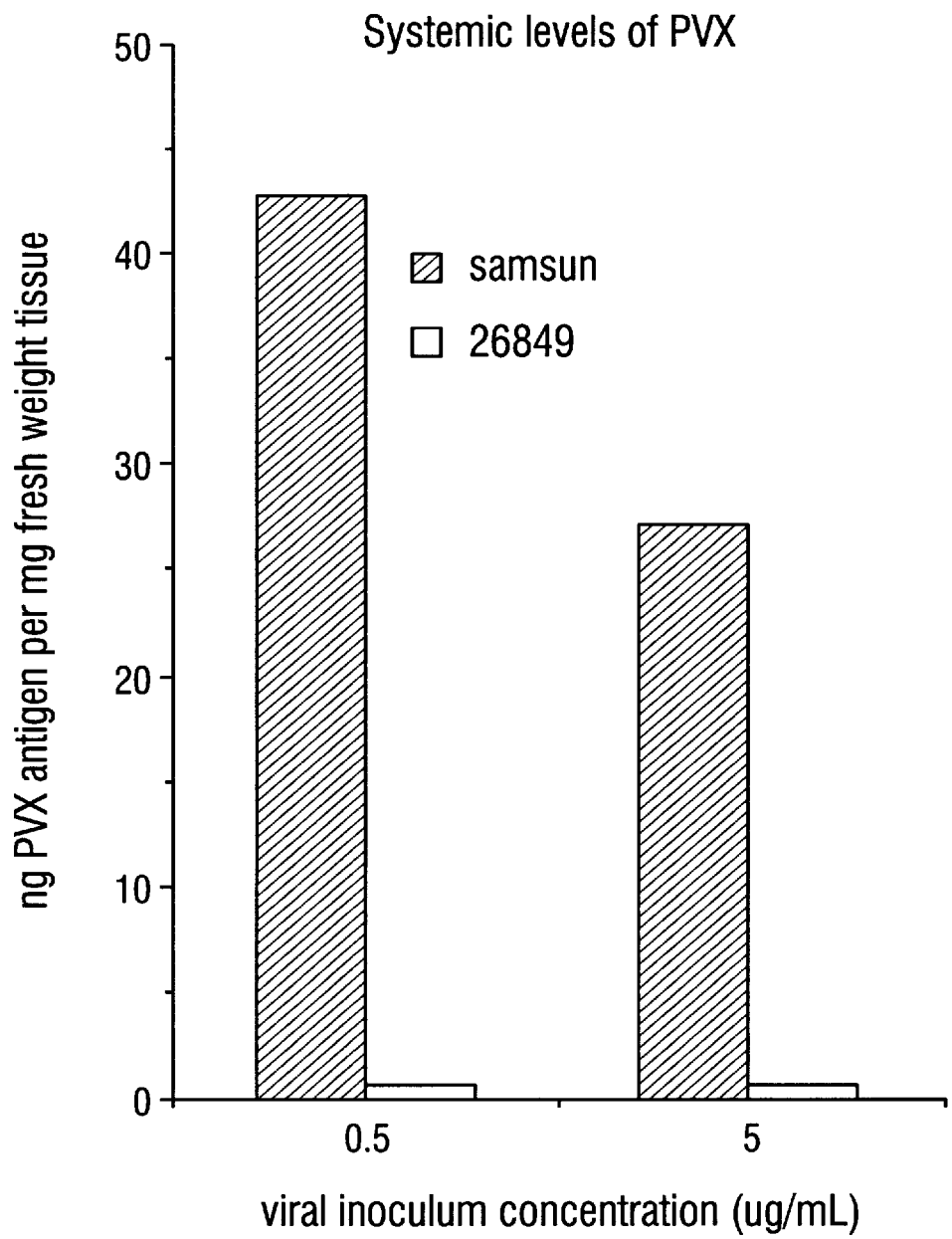
FIG. 10 is a graph illustrating the viral antigen level in a systemic leaf from tobacco plant lines expressing a truncated replicase protein and a control line.
Figure 11:
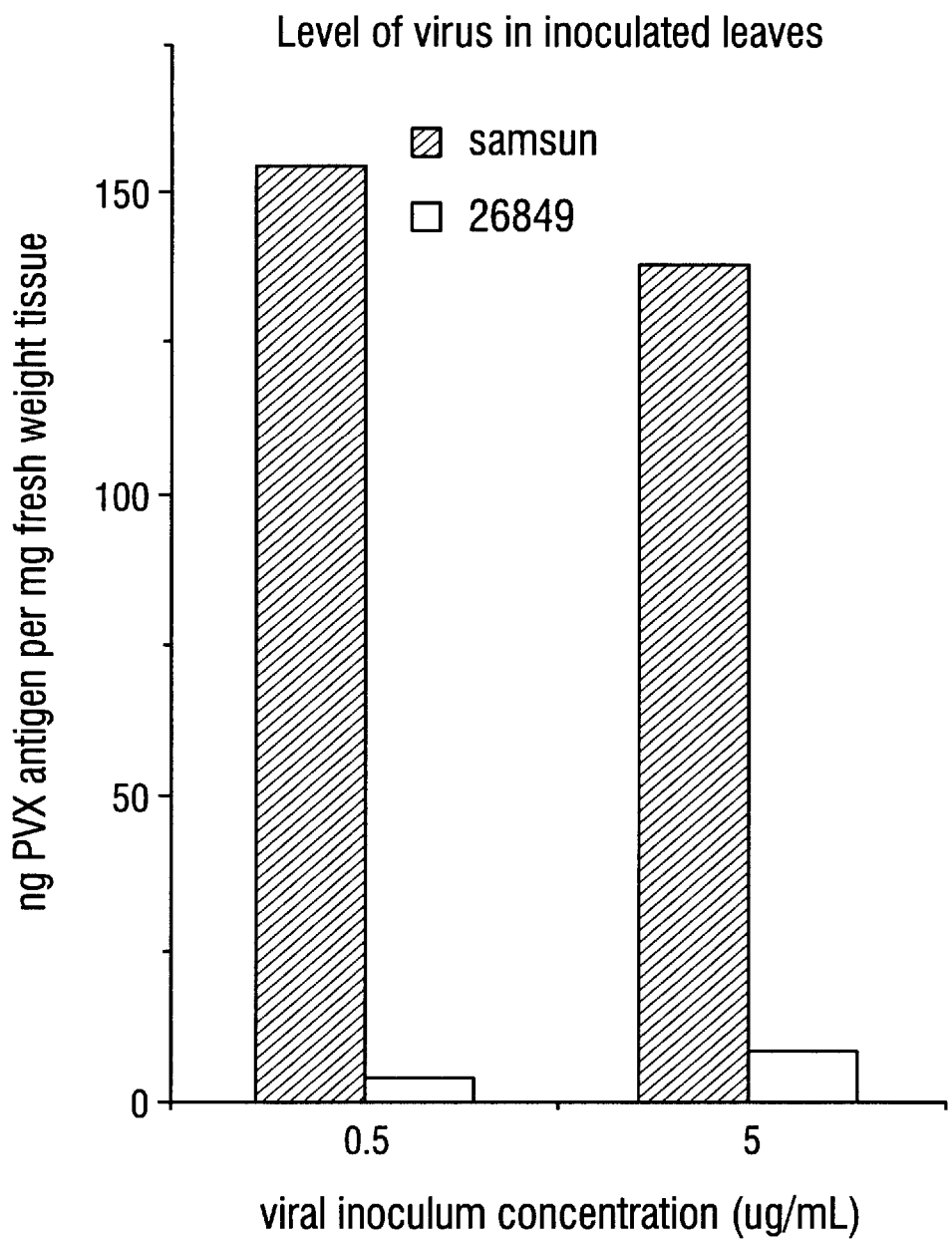
FIG. 11 is a graph illustrating the viral antigen level in inoculated leaves from tobacco plant lines expressing a truncated replicase protein and a control line.

This mutagenesis does not affect the first 674 amino acids of the PVX replicase protein from being translated. The 2215 bp Sac1 fragment of FIG. 2, containing approximately the first half of the replicase gene was cloned by standard methods into the pMON977 transformation vector. Because the replicase open reading frame was not terminated, the coding region extends into the E9 3' region of pMON977 by an additional 33 codons before a TGA stop codon terminates the open reading frame. The truncated PVX gene, which is extended by 33 codons is designated SEQ ID NO: 11, as shown in FIG. 13. The derived amino acid sequence of this extended gene is designated as SEQ ID NO: 12. Plasmid pMON8486 was mated with Agrobacterium and transformed into tobacco by the methods as described in Example 1. Expression analysis of primary transformants and protection tests were designed as described in Example 1. FIGS. 10 and 11 show that line 26849, which contains a truncated portion of the PVX replicase gene, is resistant to PVX infection when compared to the samsun control. In FIGS. 10 and 11, CP antigen levels, which are a measure of virus infection, are clearly reduced at two inoculum concentrations in both systemic and inoculated leaves. FIG. 10 represents the systemic level of PVX in plants challenged with 0.5 µl g/ml PVX inoculum concentrations and 5 µg/ml PVX viral inoculum concentrations vs. ng PVX antigen per mg fresh weight of tissue. FIG. 11 represents the levels of PVX virus in inoculated leaves under the same conditions as described for FIG. 10. Ten NPTII positive F1 plants were used per inoculum concentration in the transgenic line.

EXAMPLE 3

The plant transformation vector pMON8439 containing a PVX replicase gene can be transformed into potato using the protocol described below.

Agrobacterium containing the desired plant transformation vector are grown overnight in 2 mls of LBSCK broth. LBSCK contains 10 g NaCl, 5 g yeast extract, 10 g Bacto-Tryptone, 50 mg spectinomycin, 25 mg chloramphenicol and 50 mg kanamycin in a 1 liter volume, pH 7.0. The following day, the bacteria are diluted 1:10 with MSO or until an OD (optical density) reading of 0.2–0.3 is established. MSO contains 4.4 g MX salts (Sigma), 30 g sucrose and 2 ml $B_5$ vitamin (500×) in a 1 liter volume, pH 5.7. Leaves from the stem of potato plants that have been grown under sterile conditions for about three (3) weeks on PM media supplemented with 25 mg/l ascorbic acid are removed. PM media contains 4.4 g MS salts (Sigma), 30 g sucrose, 0.17 g $NaH_2PO_4 \cdot H_2O$, 1 ml thiamine HCl and 0.1 g Inositol in a 1 liter volume, pH 6.0 and 0.2% Gelrite agar. The stems are placed on a vegetable slicer (~30–50 at a time) and cut into 3–5 mm segments. These stem explants are inoculated for 15 minutes with the diluted bacteria. Approximately 20 mls of bacterial solution is used per 1000 stem explants. The bacterial solution is removed by aspiration and the explants placed onto prepared co-culture plates. The co-culture plates contain 1/10 MSO with 1.5 mls of TxD cells overlayed with wetted filter paper. Approximately 50 explants are placed on each plate.

After a two (2) day co-culture period, explants are placed onto callus induction plates containing MSO plus 0.5 mg/l ZR (Zeatin riboside), 10 mg/l $AgNO_3$ and 0.1 mg/l NAA (naphthaleneacetic acid) for four (4) weeks. These plates also contain 100 mg/l kanamycin to select for transformed cells. After four (4) weeks, explants that exhibit growth in the presence of kanamycin are placed on shoot induction media which contains MSO plus 5.0 mg/l ZR, 10 mg/l $AgNO_3$ and 0.3 mg/l $GA_3$ (gibberellic acid) and 100 mg/l kanamycin for further selection. Shoots typically begin to appear at about six (6) weeks. The plants are then placed in sundae cups with PM media and allowed to grow for approximately 2 weeks. Plants are placed into soil, hardened off, and analyzed to verify transformation by assaying for the presence of a protein (NPTII) which confers resistance to the antibiotic kanamycin to the plant. If the plant is positive for expression of the protein, the plant is kept for further study and maintained in tissue culture.

After the plant has been transformed and after transformed callus has been identified, the transformed callus tissue is regenerated into whole plants.

Potato plants derived from transformation with pMON8439 are screened by ELISA for the presence of neomycin phosphotransferase (NPTII) to identify transgenic potato plants. These plants are then assayed by RNA blot analysis (Thomas, 1980) to determine the presence of PVX replicase mRNA corresponding to the predicted mRNA transcript expected from pMON8439. Transgenic plants with detectable PVX RNA levels are then propagated by cuttings.

Twenty plants from each line are used in PVX protection experiments. Non-transformed Russet Burbank potato plants are used as control. Each plant is inoculated with 5 µg/ml PVX by applying 50 µl of inoculum in 0.1M phosphate buffer pH7.0, on two leaves per plant. Prior to inoculation, leaves are dusted with carborundum. Virus levels are quantitated by ELISA at 2, 3 and 4 weeks post inoculation as described in Example 1. Potato plants are selected that express the PVX replicase gene and exhibit resistance to infection by PVX.

From the foregoing, it will be seen that this invention is one well adapted to attain all the ends and objects hereinabove set forth together with advantages that are obvious and that are inherent to the invention. It will be understood that certain features and sub-combinations are of utility and can be employed without reference to other features and sub-combinations. This is contemplated by and is within the scope of the claims. Because many possible embodiments can be made of the invention without departing from the scope thereof, it is to be understood that all matter herein set forth or shown in the accompanying drawing is to be interpreted as illustrative and not a limiting sense.

BIBLIOGRAPHY

Abel et al. (1986) *Science* 232: 738–743.
Bevan (1984) *Nucl. Acids Res.* 12: 8711–8721.
Coruzzi et al. (1990) *EMBO J.* 3:1671.
Cuozzo et al. (1988) *BioTechnol.* 6: 549–557.

deBokx (1972) Viruses of Potatoes and Seed-Potato Production. p. 233. Centre for Agric. Publ. and Documentation, Wageningen, The Netherlands.

deBokx (1986) Potato Virus Y. in: Compendium of Potato Diseases p. 7–71. W. Hooker ed. American Phytopathology Society. Ditta et al. (1980) *Proc. Natl. Acad. Sci. USA* 77: 7347–7351.

Fling et al. (1985) *Nucl. Acids Res.* 13: 7095–7106.

Fraley et al. (1983) *Proc. Natl. Acad. Sci. USA* 80: 4803–4807.

Golemboski et al. (1990) *Proc. Natl. Acad. Sci. USA* 87: 6311–6315. Hemenway et al. (1988) *EMBO J.* 7: 1273–1280.

Hemenway et al. (1990) *Virology* 175: 365–371.

Herrera-Estrell (1983) *Nature* 303: 209.

Hodgman (1988) *Nature* 333: 22–23.

Horsch et al. (1985) *Science* 227: 1229–1231.

Huisman et al. (1988) *J. Gen. Virol.* 69: 1789–1798.

Ishikawa et al. (1986) *Nucleic Acids Res.* 14: 8291–8305.

Kaniewski et al. (1990) *Biotechnol.* 8:750–754.

Kay et al. (1987) *Science* 236: 1299–1302.

Klee et al. (1985) *BioTechnol.* 3: 637–642.

Koncz and Schell (1986) *Mol. Gen. Genet.* 204: 383–396.

Kunkel (1985) *Proc. Natl. Acad. Sci. USA* 82:488–492.

Lawson et al. (1990) *BioTechnol.* 8: 127–134.

Odell et al. (1985) *Nature* 313:810–812.

Purcifull and Edwardson (1981) in: Handbook of Plant Virus Infections and Comparative Diagnosis. E. Kurstak (ed). Elsevier/North Holland Biomedical Press.

Skryabin et al. (1988) *FEBS Lett.* 240: 33–40.

Stalker et al. (1981) *Mol. Gen. Genet.* 181: 8–12.

Stark and Beachy (1989) *BioTechnol.* 7: 1257–1262.

Taschner et al. (1991) *Virology* 181: 445–450.

Todd, (1957) *Proc* 3rd Conf. Potato Virus Diseases p. 132. Lisse-Wageninger, The Netherlands.

Thomas (1980) *Proc. Natl. Acad. Sci. USA* 77: 5201–5205.

Tumer et al. (1987) *EMBO J.* 6:1181–1188.

van Dun et al. (1988) *Virology* 163: 572–578.

van Dun et al. (1988) *Virology* 164: 383–389.

Zuidema et al. (1980) *J. Gen. Virol.* 70: 267–276.

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 4371 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..4371

( x i ) SEQUENCE DESCRIPTION: SEQ ID NO:1:

```
ATG  GCC  AAA  GTG  CGC  GAG  GTT  TAC  CAA  TCC  TTT  ACA  GAC  TCC  ACC  ACA       48
Met  Ala  Lys  Val  Arg  Glu  Val  Tyr  Gln  Ser  Phe  Thr  Asp  Ser  Thr  Thr
 1                    5                        10                      15

AAA  ACT  CTC  ATC  CAA  GAT  GAG  GCT  TAT  AGA  AAT  ATT  CGT  CCC  ATC  ATG       96
Lys  Thr  Leu  Ile  Gln  Asp  Glu  Ala  Tyr  Arg  Asn  Ile  Arg  Pro  Ile  Met
                      20                      25                      30

GAA  AAA  CAT  AAA  CTA  GCT  AAC  CCG  TAC  GCT  CAA  ACG  GTT  GAA  GCG  GCT      144
Glu  Lys  His  Lys  Leu  Ala  Asn  Pro  Tyr  Ala  Gln  Thr  Val  Glu  Ala  Ala
           35                        40                       45

AAT  GAT  CTA  GAG  GGG  TTC  GGC  ATA  GCC  ACC  AAT  CCC  TAT  AGC  ATT  GAG      192
Asn  Asp  Leu  Glu  Gly  Phe  Gly  Ile  Ala  Thr  Asn  Pro  Tyr  Ser  Ile  Glu
      50                        55                       60

TTG  CAT  ACA  CAT  GCA  GCT  GCT  AAG  ACC  ATA  GAG  AAT  AAA  CTT  CTA  GAG      240
Leu  His  Thr  His  Ala  Ala  Ala  Lys  Thr  Ile  Glu  Asn  Lys  Leu  Leu  Glu
 65                        70                       75                       80

GTG  CTT  GGT  TCC  ATC  CTA  CCA  CAA  GAA  CCT  GTT  ACA  TTT  ATG  TTC  CTT      288
Val  Leu  Gly  Ser  Ile  Leu  Pro  Gln  Glu  Pro  Val  Thr  Phe  Met  Phe  Leu
                      85                       90                       95

AAA  CCC  AGG  AAG  CTA  AAC  TAC  ATG  AGA  AGA  AAC  CCG  CGG  ATC  AAG  GAC      336
Lys  Pro  Arg  Lys  Leu  Asn  Tyr  Met  Arg  Arg  Asn  Pro  Arg  Ile  Lys  Asp
               100                      105                     110

ATT  TTC  CAC  AAT  GTT  GCC  ATT  GAA  CCG  AGA  GAC  GTA  GCA  AGG  TAC  CCC      384
Ile  Phe  His  Asn  Val  Ala  Ile  Glu  Pro  Arg  Asp  Val  Ala  Arg  Tyr  Pro
```

```
                    115                         120                         125
AAG  GAA  ACA  ATA  ATT  GAC  AAA  CTC  ACA  GAG  ATC  ACA  ACA  GAC  ACA  GCA        432
Lys  Glu  Thr  Ile  Ile  Asp  Lys  Leu  Thr  Glu  Ile  Thr  Thr  Asp  Thr  Ala
130                      135                           140

TAC  ATT  AGT  GAC  ACT  CTG  CAC  TTC  TTG  GAT  CCG  AGC  TAC  ATA  GTG  GAG        480
Tyr  Ile  Ser  Asp  Thr  Leu  His  Phe  Leu  Asp  Pro  Ser  Tyr  Ile  Val  Glu
145                      150                           155                     160

ACA  TTC  CAA  AAC  TGC  CCA  AAA  CTG  CAA  ACA  TTG  TAT  GCG  ACC  TTA  GTT        528
Thr  Phe  Gln  Asn  Cys  Pro  Lys  Leu  Gln  Thr  Leu  Tyr  Ala  Thr  Leu  Val
                    165                           170                     175

CTC  CCC  GTT  GAG  GCA  GCC  TTC  AAA  ATG  GAA  AGC  ACT  CAC  CCG  AAC  ATA        576
Leu  Pro  Val  Glu  Ala  Ala  Phe  Lys  Met  Glu  Ser  Thr  His  Pro  Asn  Ile
               180                           185                     190

TAC  AGC  CTC  AAA  TAC  TTC  GGA  GAT  GGT  TTC  CAG  TAT  ATA  CCA  GGC  AAC        624
Tyr  Ser  Leu  Lys  Tyr  Phe  Gly  Asp  Gly  Phe  Gln  Tyr  Ile  Pro  Gly  Asn
          195                           200                     205

CAT  GGT  GGT  GGA  GCG  TAC  CAT  CAT  GAA  TTT  GCT  CAT  TTA  CAA  TGG  CTC        672
His  Gly  Gly  Gly  Ala  Tyr  His  His  Glu  Phe  Ala  His  Leu  Gln  Trp  Leu
210                           215                     220

AAA  GTG  GGA  AAG  ATC  AAA  TGG  AGG  GAC  CCC  AAG  GAT  AGC  TTT  CTC  GGA        720
Lys  Val  Gly  Lys  Ile  Lys  Trp  Arg  Asp  Pro  Lys  Asp  Ser  Phe  Leu  Gly
225                      230                           235                     240

CAT  CTC  AAT  TAC  ACG  ACT  GAG  CAG  GTT  GAG  ATG  CAC  ACA  GTG  ACA  GTG        768
His  Leu  Asn  Tyr  Thr  Thr  Glu  Gln  Val  Glu  Met  His  Thr  Val  Thr  Val
                    245                           250                     255

CAG  TTG  CAG  GAA  TCG  TTC  GCG  GCA  AAC  CAC  TTG  TAC  TGC  ATC  AGG  AGA        816
Gln  Leu  Gln  Glu  Ser  Phe  Ala  Ala  Asn  His  Leu  Tyr  Cys  Ile  Arg  Arg
               260                           265                     270

GGA  GAT  TTG  CTC  ACA  CCG  GAG  GTG  CGC  ACT  TTT  GGC  CAA  CCT  GAC  AGG        864
Gly  Asp  Leu  Leu  Thr  Pro  Glu  Val  Arg  Thr  Phe  Gly  Gln  Pro  Asp  Arg
          275                           280                     285

TAT  GTG  ATT  CCA  CCA  CAG  ATC  TTC  CTC  CCG  AAA  GTC  CAT  AAC  TGC  AAG        912
Tyr  Val  Ile  Pro  Pro  Gln  Ile  Phe  Leu  Pro  Lys  Val  His  Asn  Cys  Lys
290                           295                     300

AAG  CCG  ATT  CTT  AAA  AAA  ACT  ATG  ATG  CAG  CTC  TTC  TTG  TAT  GTT  AGG        960
Lys  Pro  Ile  Leu  Lys  Lys  Thr  Met  Met  Gln  Leu  Phe  Leu  Tyr  Val  Arg
305                      310                           315                     320

ACA  GTT  AAG  GTC  GCA  AAA  AAT  TGT  GAC  ATT  TTT  GCC  AAA  GTC  AGA  CAA        1008
Thr  Val  Lys  Val  Ala  Lys  Asn  Cys  Asp  Ile  Phe  Ala  Lys  Val  Arg  Gln
                    325                           330                     335

TTA  ATT  AAA  TCA  TCT  GAC  CTG  GAC  AAA  TAT  TCT  GCT  GTG  GAA  CTG  GTT        1056
Leu  Ile  Lys  Ser  Ser  Asp  Leu  Asp  Lys  Tyr  Ser  Ala  Val  Glu  Leu  Val
               340                           345                     350

TAC  TTA  GTA  AGC  TAT  ATG  GAG  TTC  CTT  GCC  GAT  CTA  CAA  GCT  ACC  ACC        1104
Tyr  Leu  Val  Ser  Tyr  Met  Glu  Phe  Leu  Ala  Asp  Leu  Gln  Ala  Thr  Thr
          355                           360                     365

TGC  TTC  TCA  GAC  ACA  CTT  TCT  GGT  GGC  TTA  CTA  ACA  AAG  ACC  CTT  GCA        1152
Cys  Phe  Ser  Asp  Thr  Leu  Ser  Gly  Gly  Leu  Leu  Thr  Lys  Thr  Leu  Ala
370                           375                     380

CCG  GTG  AGG  GCT  TGG  ATA  CAA  GAG  AAA  AAG  ATG  CAG  CTG  TTT  GGT  CTT        1200
Pro  Val  Arg  Ala  Trp  Ile  Gln  Glu  Lys  Lys  Met  Gln  Leu  Phe  Gly  Leu
385                      390                           395                     400

GAG  GAC  TAC  GCG  AAG  TTA  GTC  AAA  GCA  GTT  GAT  TTC  CAC  CCA  GTG  GAT        1248
Glu  Asp  Tyr  Ala  Lys  Leu  Val  Lys  Ala  Val  Asp  Phe  His  Pro  Val  Asp
                    405                           410                     415

TTT  TCT  TTT  AAA  GTT  GAA  ACT  TGG  GAC  TTC  AGA  TTC  CAC  CCC  TTG  CAA        1296
Phe  Ser  Phe  Lys  Val  Glu  Thr  Trp  Asp  Phe  Arg  Phe  His  Pro  Leu  Gln
               420                           425                     430

GCG  TGG  AAA  GCC  TTC  CGA  CCA  AGG  GAA  GTG  TCG  GAT  GTA  GAG  GAA  ATG        1344
Ala  Trp  Lys  Ala  Phe  Arg  Pro  Arg  Glu  Val  Ser  Asp  Val  Glu  Glu  Met
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 435 |     |     |     |     | 440 |     |     |     |     | 445 |     |     |      |
| GAA | AGT | TTG | TTC | TCA | GAT | GGG | GAC | CTG | CTT | GAC | TGC | TTC | ACA | AGA | ATG | 1392 |
| Glu | Ser | Leu | Phe | Ser | Asp | Gly | Asp | Leu | Leu | Asp | Cys | Phe | Thr | Arg | Met |      |
|     | 450 |     |     |     |     | 455 |     |     |     |     | 460 |     |     |     |     |      |
| CCA | GCT | TAT | GCA | GTA | AAC | GCA | GAG | GAA | GAT | TTA | GCT | ACA | ATC | AGG | AAA | 1440 |
| Pro | Ala | Tyr | Ala | Val | Asn | Ala | Glu | Glu | Asp | Leu | Ala | Thr | Ile | Arg | Lys |      |
| 465 |     |     |     |     | 470 |     |     |     |     | 475 |     |     |     |     | 480 |      |
| ACG | CCC | GAG | ATG | GAT | GTC | GGT | CAA | GAA | GCC | AAA | GAA | CCT | GCA | GGA | GAC | 1488 |
| Thr | Pro | Glu | Met | Asp | Val | Gly | Gln | Glu | Ala | Lys | Glu | Pro | Ala | Gly | Asp |      |
|     |     |     |     | 485 |     |     |     |     | 490 |     |     |     |     | 495 |     |      |
| AGA | AAT | CAA | TAC | TTA | AAC | CCT | GCA | GAA | ACT | TTC | CTC | AAC | AAG | CTC | CAC | 1536 |
| Arg | Asn | Gln | Tyr | Leu | Asn | Pro | Ala | Glu | Thr | Phe | Leu | Asn | Lys | Leu | His |      |
|     |     |     | 500 |     |     |     |     | 505 |     |     |     |     | 510 |     |     |      |
| AGG | AAA | CAC | AGT | AGG | GAG | GTG | AAA | CAT | CAG | GCC | GTA | AAG | AAA | GCT | AAA | 1584 |
| Arg | Lys | His | Ser | Arg | Glu | Val | Lys | His | Gln | Ala | Val | Lys | Lys | Ala | Lys |      |
|     |     | 515 |     |     |     |     | 520 |     |     |     |     | 525 |     |     |     |      |
| CGC | CTA | GCT | GAA | ATC | CAG | GAG | TCC | ATG | AGA | GCT | GAG | GGT | GAG | GCC | GAA | 1632 |
| Arg | Leu | Ala | Glu | Ile | Gln | Glu | Ser | Met | Arg | Ala | Glu | Gly | Glu | Ala | Glu |      |
|     | 530 |     |     |     |     | 535 |     |     |     |     | 540 |     |     |     |     |      |
| CTA | AAT | GAG | ATG | AGC | GGG | GGC | ATG | AGG | GCA | ATA | CCT | AGC | AAC | GCA | GAA | 1680 |
| Leu | Asn | Glu | Met | Ser | Gly | Gly | Met | Arg | Ala | Ile | Pro | Ser | Asn | Ala | Glu |      |
| 545 |     |     |     |     | 550 |     |     |     |     | 555 |     |     |     |     | 560 |      |
| CTT | CCC | AGC | ACG | AAC | GAT | GCT | AGA | CAA | GAA | CTC | ACA | CTC | CCA | ACC | ACT | 1728 |
| Leu | Pro | Ser | Thr | Asn | Asp | Ala | Arg | Gln | Glu | Leu | Thr | Leu | Pro | Thr | Thr |      |
|     |     |     |     | 565 |     |     |     |     | 570 |     |     |     |     | 575 |     |      |
| AAA | CCT | GTC | CCT | GCA | AGG | TGG | GAA | GAT | GCT | TCA | TTC | ACA | GAT | TCT | AGT | 1776 |
| Lys | Pro | Val | Pro | Ala | Arg | Trp | Glu | Asp | Ala | Ser | Phe | Thr | Asp | Ser | Ser |      |
|     |     |     | 580 |     |     |     |     | 585 |     |     |     |     | 590 |     |     |      |
| GTG | AAA | GAG | GAG | CAA | GTG | AAA | CTC | CCT | GGA | AAA | GAA | GCC | GTT | GAG | ACA | 1824 |
| Val | Lys | Glu | Glu | Gln | Val | Lys | Leu | Pro | Gly | Lys | Glu | Ala | Val | Glu | Thr |      |
|     |     | 595 |     |     |     |     | 600 |     |     |     |     | 605 |     |     |     |      |
| GCG | ACG | CAA | CAA | GTC | ATA | GAA | GGA | CTC | CCT | TGG | AAA | CAC | TGG | ATT | CCT | 1872 |
| Ala | Thr | Gln | Gln | Val | Ile | Glu | Gly | Leu | Pro | Trp | Lys | His | Trp | Ile | Pro |      |
|     | 610 |     |     |     |     | 615 |     |     |     |     | 620 |     |     |     |     |      |
| CAA | CTA | AAT | GCT | GTT | GGA | TTC | AAG | GCG | CTG | GAA | ATT | CAG | AGG | GAT | AGG | 1920 |
| Gln | Leu | Asn | Ala | Val | Gly | Phe | Lys | Ala | Leu | Glu | Ile | Gln | Arg | Asp | Arg |      |
| 625 |     |     |     |     | 630 |     |     |     |     | 635 |     |     |     |     | 640 |      |
| AGT | GGG | ACA | ATG | ATC | ATG | CCC | ATC | ACA | GAA | ATG | GTC | TCC | GGG | TTG | GAA | 1968 |
| Ser | Gly | Thr | Met | Ile | Met | Pro | Ile | Thr | Glu | Met | Val | Ser | Gly | Leu | Glu |      |
|     |     |     |     | 645 |     |     |     |     | 650 |     |     |     |     | 655 |     |      |
| AAA | GAG | GAC | TTC | CCG | GAA | GGA | ACT | CCA | AAA | GAG | TTG | GCA | CGA | GAA | TTG | 2016 |
| Lys | Glu | Asp | Phe | Pro | Glu | Gly | Thr | Pro | Lys | Glu | Leu | Ala | Arg | Glu | Leu |      |
|     |     |     | 660 |     |     |     |     | 665 |     |     |     |     | 670 |     |     |      |
| CTC | GCT | ATG | AAC | AGA | AGC | CCT | GCC | ACC | ATT | CCT | TTG | GAC | CTG | CTT | AGA | 2064 |
| Leu | Ala | Met | Asn | Arg | Ser | Pro | Ala | Thr | Ile | Pro | Leu | Asp | Leu | Leu | Arg |      |
|     |     | 675 |     |     |     |     | 680 |     |     |     |     | 685 |     |     |     |      |
| GCC | AGA | GAC | TAC | GGC | AGT | GAT | GTG | AAG | AAC | AAG | AGA | ATT | GGT | GCC | ATC | 2112 |
| Ala | Arg | Asp | Tyr | Gly | Ser | Asp | Val | Lys | Asn | Lys | Arg | Ile | Gly | Ala | Ile |      |
|     | 690 |     |     |     |     | 695 |     |     |     |     | 700 |     |     |     |     |      |
| ACA | AAG | ACA | CAA | GCA | ACA | AGT | TGG | GGC | GAG | TAC | CTA | ACA | GGA | AAG | ATA | 2160 |
| Thr | Lys | Thr | Gln | Ala | Thr | Ser | Trp | Gly | Glu | Tyr | Leu | Thr | Gly | Lys | Ile |      |
| 705 |     |     |     |     | 710 |     |     |     |     | 715 |     |     |     |     | 720 |      |
| GAA | AGT | CTG | ACT | GAG | AGG | AAA | GTT | GCG | ACT | TGT | GTC | ATT | CAT | GGA | GCT | 2208 |
| Glu | Ser | Leu | Thr | Glu | Arg | Lys | Val | Ala | Thr | Cys | Val | Ile | His | Gly | Ala |      |
|     |     |     |     | 725 |     |     |     |     | 730 |     |     |     |     | 735 |     |      |
| GGA | GGC | TCT | GGG | AAA | AGT | CAT | GCC | ATC | CAG | AAG | GCA | TTG | AGA | GAA | ATT | 2256 |
| Gly | Gly | Ser | Gly | Lys | Ser | His | Ala | Ile | Gln | Lys | Ala | Leu | Arg | Glu | Ile |      |
|     |     |     | 740 |     |     |     |     | 745 |     |     |     |     | 750 |     |     |      |
| GGC | AAG | GGG | TCA | GAC | ATC | ACT | GTA | GTC | CTG | CCG | ACC | AAT | GAA | CTG | CGA | 2304 |
| Gly | Lys | Gly | Ser | Asp | Ile | Thr | Val | Val | Leu | Pro | Thr | Asn | Glu | Leu | Arg |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 755 |     |     |     |     | 760 |     |     |     |     | 765 |     |     |     |      |
| CTA | GAT | TGG | AGC | AAG | AAA | GTG | CCT | AAC | ACT | GAA | CCA | TAT | ATG | TTC | AAG | 2352 |
| Leu | Asp | Trp | Ser | Lys | Lys | Val | Pro | Asn | Thr | Glu | Pro | Tyr | Met | Phe | Lys |      |
|     |     | 770 |     |     |     |     | 775 |     |     |     |     | 780 |     |     |     |      |
| ACC | TAT | GAA | AAG | GCA | TTA | ATT | GGG | GGA | ACA | GGC | AGT | ATA | GTC | ATC | TTT | 2400 |
| Thr | Tyr | Glu | Lys | Ala | Leu | Ile | Gly | Gly | Thr | Gly | Ser | Ile | Val | Ile | Phe |      |
| 785 |     |     |     |     | 790 |     |     |     |     | 795 |     |     |     |     | 800 |      |
| GAC | GAT | TAC | TCA | AAA | CTT | CCT | CCC | GGT | TAC | ATA | GAA | GCC | TTA | ATC | TGT | 2448 |
| Asp | Asp | Tyr | Ser | Lys | Leu | Pro | Pro | Gly | Tyr | Ile | Glu | Ala | Leu | Ile | Cys |      |
|     |     |     |     | 805 |     |     |     |     | 810 |     |     |     |     | 815 |     |      |
| TTC | TAC | TCT | AAA | ATC | AAG | CTA | GTC | ATT | CTA | ACA | GGA | GAT | AGC | AGA | CAG | 2496 |
| Phe | Tyr | Ser | Lys | Ile | Lys | Leu | Val | Ile | Leu | Thr | Gly | Asp | Ser | Arg | Gln |      |
|     |     |     | 820 |     |     |     |     | 825 |     |     |     |     | 830 |     |     |      |
| AGC | GTC | TAC | CAT | GAA | ACT | GCT | GAG | GAC | GCC | TCC | ATC | AGG | CAT | TTG | GGA | 2544 |
| Ser | Val | Tyr | His | Glu | Thr | Ala | Glu | Asp | Ala | Ser | Ile | Arg | His | Leu | Gly |      |
|     |     | 835 |     |     |     |     | 840 |     |     |     |     | 845 |     |     |     |      |
| CCA | GCG | ACA | GAG | TAC | TTC | TCA | AAA | TAC | TGC | CGA | TAC | TAT | CTC | AAT | GCT | 2592 |
| Pro | Ala | Thr | Glu | Tyr | Phe | Ser | Lys | Tyr | Cys | Arg | Tyr | Tyr | Leu | Asn | Ala |      |
|     | 850 |     |     |     |     | 855 |     |     |     |     | 860 |     |     |     |     |      |
| ACA | CAC | CGC | AAC | AAG | AAA | GAC | CTT | GCG | AAC | ATG | CTC | GGT | GTC | TAC | AGT | 2640 |
| Thr | His | Arg | Asn | Lys | Lys | Asp | Leu | Ala | Asn | Met | Leu | Gly | Val | Tyr | Ser |      |
| 865 |     |     |     |     | 870 |     |     |     |     | 875 |     |     |     |     | 880 |      |
| GAG | AGA | ACG | GGG | GTC | ACC | GAA | ATC | AGC | ATG | AGC | GCC | GAG | TTC | TTA | GAA | 2688 |
| Glu | Arg | Thr | Gly | Val | Thr | Glu | Ile | Ser | Met | Ser | Ala | Glu | Phe | Leu | Glu |      |
|     |     |     |     | 885 |     |     |     |     | 890 |     |     |     |     | 895 |     |      |
| GGA | ATC | CCA | ACT | TTA | GTA | CCC | TCG | GAT | GAG | AAG | AGA | AAG | CTG | TAC | ATG | 2736 |
| Gly | Ile | Pro | Thr | Leu | Val | Pro | Ser | Asp | Glu | Lys | Arg | Lys | Leu | Tyr | Met |      |
|     |     |     | 900 |     |     |     |     | 905 |     |     |     |     | 910 |     |     |      |
| GGC | ACC | GGG | AGG | AAC | GAC | ACG | TTC | ACA | TAC | GCT | GGA | TGC | CAG | GGG | CTG | 2784 |
| Gly | Thr | Gly | Arg | Asn | Asp | Thr | Phe | Thr | Tyr | Ala | Gly | Cys | Gln | Gly | Leu |      |
|     |     | 915 |     |     |     |     | 920 |     |     |     |     | 925 |     |     |     |      |
| ACC | AAG | CCG | AAA | GTA | CAA | ATA | GTG | TTG | GAC | CAC | AAC | ACC | CAA | GTG | TGT | 2832 |
| Thr | Lys | Pro | Lys | Val | Gln | Ile | Val | Leu | Asp | His | Asn | Thr | Gln | Val | Cys |      |
| 930 |     |     |     |     | 935 |     |     |     |     | 940 |     |     |     |     |     |      |
| AGC | GCG | AAT | GTG | ATG | TAC | ACG | GCA | CTT | TCT | AGA | GCC | ACC | GAC | AGG | ATT | 2880 |
| Ser | Ala | Asn | Val | Met | Tyr | Thr | Ala | Leu | Ser | Arg | Ala | Thr | Asp | Arg | Ile |      |
| 945 |     |     |     | 950 |     |     |     |     | 955 |     |     |     |     | 960 |     |      |
| CAC | TTC | GTG | AAC | ACA | AGT | GCA | AAC | TCT | TCG | GCC | TTC | TGG | GAA | AAG | TTA | 2928 |
| His | Phe | Val | Asn | Thr | Ser | Ala | Asn | Ser | Ser | Ala | Phe | Trp | Glu | Lys | Leu |      |
|     |     |     |     | 965 |     |     |     |     | 970 |     |     |     |     | 975 |     |      |
| GAC | AGC | ACC | CCT | TAT | CTC | AAG | ACT | TTC | CTA | TCA | GTG | GTG | AGA | GAA | CAA | 2976 |
| Asp | Ser | Thr | Pro | Tyr | Leu | Lys | Thr | Phe | Leu | Ser | Val | Val | Arg | Glu | Gln |      |
|     |     |     | 980 |     |     |     |     | 985 |     |     |     |     | 990 |     |     |      |
| GCA | CTC | AGG | GAG | TAC | GAG | CCG | GCA | GAG | GCA | GAG | CCA | ATT | CGA | GAG | CCT | 3024 |
| Ala | Leu | Arg | Glu | Tyr | Glu | Pro | Ala | Glu | Ala | Glu | Pro | Ile | Arg | Glu | Pro |      |
|     |     | 995 |     |     |     |     | 1000|     |     |     |     | 1005|     |     |     |      |
| GAG | CCC | CAG | ACA | CAC | ATG | TGT | GTC | GAG | AAT | GAG | GAG | TCC | GTG | CTA | GAA | 3072 |
| Glu | Pro | Gln | Thr | His | Met | Cys | Val | Glu | Asn | Glu | Glu | Ser | Val | Leu | Glu |      |
|     |     | 1010|     |     |     |     | 1015|     |     |     |     | 1020|     |     |     |      |
| GAG | TAC | AAA | GAG | GAA | CTC | TTG | GAA | AAG | TTT | GAC | AGA | GAG | ATC | CAC | TCG | 3120 |
| Glu | Tyr | Lys | Glu | Glu | Leu | Leu | Glu | Lys | Phe | Asp | Arg | Glu | Ile | His | Ser |      |
|     |     | 1025|     |     |     |     | 1030|     |     |     |     | 1035|     |     | 1040|      |
| GAA | TCC | CAT | GGT | CAT | TCA | AAC | TGT | GTC | CAA | ACA | GAA | GAC | ACA | ACC | ATT | 3168 |
| Glu | Ser | His | Gly | His | Ser | Asn | Cys | Val | Gln | Thr | Glu | Asp | Thr | Thr | Ile |      |
|     |     |     |     | 1045|     |     |     |     | 1050|     |     |     |     | 1055|     |      |
| CAG | TTG | TTT | TCG | CAT | CAA | CAA | GCA | AAA | GAT | GAG | ACC | CTC | CTC | TGG | GCG | 3216 |
| Gln | Leu | Phe | Ser | His | Gln | Gln | Ala | Lys | Asp | Glu | Thr | Leu | Leu | Trp | Ala |      |
|     |     |     |     | 1060|     |     |     |     | 1065|     |     |     |     | 1070|     |      |
| ACT | ATA | GAT | GCG | CGG | CTC | AAG | ATT | AGC | AAT | CAA | GAG | ACA | AAC | TTC | CGA | 3264 |
| Thr | Ile | Asp | Ala | Arg | Leu | Lys | Ile | Ser | Asn | Gln | Glu | Thr | Asn | Phe | Arg |      |

```
                   1 0 7 5                        1 0 8 0                        1 0 8 5
GAA  TTC  TTG  AGC  AAG  AAG  GAC  ATT  GGG  GAC  GTT  CTG  TTT  TTG  AAC  TAC        3312
Glu  Phe  Leu  Ser  Lys  Lys  Asp  Ile  Gly  Asp  Val  Leu  Phe  Leu  Asn  Tyr
          1 0 9 0                        1 0 9 5                        1 1 0 0

CAA  AAA  GCT  ATG  GGT  CTG  CCC  AAA  GAG  CGT  ATT  CCC  TTT  TCA  CAA  GAG        3360
Gln  Lys  Ala  Met  Gly  Leu  Pro  Lys  Glu  Arg  Ile  Pro  Phe  Ser  Gln  Glu
1 1 0 5                        1 1 1 0                        1 1 1 5                        1 1 2 0

GTC  TGG  GAA  GCT  TGT  GCC  CAT  GAA  GTA  CAA  AGC  AAG  TAC  CTC  AGT  AAG        3408
Val  Trp  Glu  Ala  Cys  Ala  His  Glu  Val  Gln  Ser  Lys  Tyr  Leu  Ser  Lys
                         1 1 2 5                        1 1 3 0                        1 1 3 5

TCA  AAG  TGC  AAC  TTG  ATC  AAC  GGG  ACT  GTG  AGA  CAG  AGC  CCA  GAC  TTT        3456
Ser  Lys  Cys  Asn  Leu  Ile  Asn  Gly  Thr  Val  Arg  Gln  Ser  Pro  Asp  Phe
               1 1 4 0                        1 1 4 5                        1 1 5 0

GAC  GAA  AAC  AAA  ATT  ATG  GTA  TTC  CTC  AAG  TCG  CAG  TGG  GTC  ACA  AAG        3504
Asp  Glu  Asn  Lys  Ile  Met  Val  Phe  Leu  Lys  Ser  Gln  Trp  Val  Thr  Lys
                    1 1 5 5                        1 1 6 0                        1 1 6 5

GTG  GAA  AAG  CTA  GGT  CTA  CCC  AAG  ATT  AAG  CCA  GGT  CAA  ACC  ATA  GCA        3552
Val  Glu  Lys  Leu  Gly  Leu  Pro  Lys  Ile  Lys  Pro  Gly  Gln  Thr  Ile  Ala
          1 1 7 0                        1 1 7 5                        1 1 8 0

GCT  TTT  TAT  CAG  CAG  ACT  GTG  ATG  CTT  TTT  GGA  ACT  ATG  GCT  AGG  TAC        3600
Ala  Phe  Tyr  Gln  Gln  Thr  Val  Met  Leu  Phe  Gly  Thr  Met  Ala  Arg  Tyr
1 1 8 5                        1 1 9 0                        1 1 9 5                        1 2 0 0

ATG  CGA  TGG  TTC  AGA  CAG  GCT  TTC  CAG  CCA  AAA  GAA  GTC  TTC  ATA  AAC        3648
Met  Arg  Trp  Phe  Arg  Gln  Ala  Phe  Gln  Pro  Lys  Glu  Val  Phe  Ile  Asn
                         1 2 0 5                        1 2 1 0                        1 2 1 5

TGT  GAG  ACC  ACG  CCA  GAA  GAC  ATG  TCT  GCA  TGG  GCC  TTG  AAC  AAC  TGG        3696
Cys  Glu  Thr  Thr  Pro  Glu  Asp  Met  Ser  Ala  Trp  Ala  Leu  Asn  Asn  Trp
               1 2 2 0                        1 2 2 5                        1 2 3 0

AAT  TTC  GGC  AGA  CCT  AGC  TTG  GCC  AAT  GAC  TAC  ACA  GCT  TTC  GAC  CAG        3744
Asn  Phe  Gly  Arg  Pro  Ser  Leu  Ala  Asn  Asp  Tyr  Thr  Ala  Phe  Asp  Gln
          1 2 3 5                        1 2 4 0                        1 2 4 5

TCT  CAG  GAT  GGA  GCT  ATG  CTG  CAA  TTT  GAG  GTG  CTC  AAA  GCC  AAG  CAC        3792
Ser  Gln  Asp  Gly  Ala  Met  Leu  Gln  Phe  Glu  Val  Leu  Lys  Ala  Lys  His
1 2 5 0                        1 2 5 5                        1 2 6 0

CAT  TGC  ATA  CCA  GAG  GAA  ATC  ATC  CAA  GCA  TAC  ATA  GAC  ATT  AAG  ACC        3840
His  Cys  Ile  Pro  Glu  Glu  Ile  Ile  Gln  Ala  Tyr  Ile  Asp  Ile  Lys  Thr
1 2 6 5                        1 2 7 0                        1 2 7 5                        1 2 8 0

AAT  GCA  CAG  ATT  TTC  CTA  GGC  ACA  TTG  TCA  ATC  ATG  CGC  CTG  ACT  GGT        3888
Asn  Ala  Gln  Ile  Phe  Leu  Gly  Thr  Leu  Ser  Ile  Met  Arg  Leu  Thr  Gly
                         1 2 8 5                        1 2 9 0                        1 2 9 5

GAG  GGT  CCC  ACT  TTT  GAT  GCA  AAC  ACT  GAG  TGC  AAC  ATA  GCT  TAC  ACC        3936
Glu  Gly  Pro  Thr  Phe  Asp  Ala  Asn  Thr  Glu  Cys  Asn  Ile  Ala  Tyr  Thr
               1 3 0 0                        1 3 0 5                        1 3 1 0

CAT  ACA  AAG  TTT  GAC  ATC  CCA  GCA  GGA  ACT  GCT  CAA  GTT  TAT  GCA  GGA        3984
His  Thr  Lys  Phe  Asp  Ile  Pro  Ala  Gly  Thr  Ala  Gln  Val  Tyr  Ala  Gly
          1 3 1 5                        1 3 2 0                        1 3 2 5

GAC  GAC  TCA  GCA  CTG  GAT  TGC  GTT  CCA  GAA  GTG  AAG  CAT  AGC  TTC  CAC        4032
Asp  Asp  Ser  Ala  Leu  Asp  Cys  Val  Pro  Glu  Val  Lys  His  Ser  Phe  His
1 3 3 0                        1 3 3 5                        1 3 4 0

AGG  CTT  GAA  GAC  AAA  CTA  CTC  CTT  AAG  TCA  AAG  CCC  GTA  ATC  ACG  CAG        4080
Arg  Leu  Glu  Asp  Lys  Leu  Leu  Leu  Lys  Ser  Lys  Pro  Val  Ile  Thr  Gln
1 3 4 5                        1 3 5 0                        1 3 5 5                        1 3 6 0

CAA  AAG  AAA  GGC  AGT  TGG  CCT  GAG  TTT  TGT  GGT  TGG  CTG  ATT  ACA  CCA        4128
Gln  Lys  Lys  Gly  Ser  Trp  Pro  Glu  Phe  Cys  Gly  Trp  Leu  Ile  Thr  Pro
                         1 3 6 5                        1 3 7 0                        1 3 7 5

AAA  GGG  GTA  ATG  AAA  GAC  CCA  ATT  AAG  CTC  CAT  GTT  AGC  TTA  AAA  TTG        4176
Lys  Gly  Val  Met  Lys  Asp  Pro  Ile  Lys  Leu  His  Val  Ser  Leu  Lys  Leu
               1 3 8 0                        1 3 8 5                        1 3 9 0

GCC  GAA  GCT  AAG  GGC  GAA  CTC  AAG  AAA  TGT  CAA  GAC  TCC  TAT  GAA  ATT        4224
Ala  Glu  Ala  Lys  Gly  Glu  Leu  Lys  Lys  Cys  Gln  Asp  Ser  Tyr  Glu  Ile
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 1395 |     |     |     |     | 1400 |     |     |     |     | 1405 |     |     |     |     |
| GAT | CTG | AGT | TAT | GCC | TAC | GAC | CAC | AAG | GAC | TCT | CTG | CAT | GAC | TTG | TTC | 4272 |
| Asp | Leu | Ser | Tyr | Ala | Tyr | Asp | His | Lys | Asp | Ser | Leu | His | Asp | Leu | Phe |     |
|     |     | 1410 |     |     |     |     | 1415 |     |     |     |     | 1420 |     |     |     |     |
| GAT | GAG | AAA | CAG | TGT | CAG | GCA | CAT | ACA | CTC | ACT | TGC | AGA | ACA | CTG | ATC | 4320 |
| Asp | Glu | Lys | Gln | Cys | Gln | Ala | His | Thr | Leu | Thr | Cys | Arg | Thr | Leu | Ile |     |
| 1425 |     |     |     | 1430 |     |     |     |     | 1435 |     |     |     |     |     | 1440 |     |
| AAG | TCA | GGG | AGA | GGC | ACT | GTC | TCA | CTT | CCC | CGC | CTC | AGA | AAC | TTT | CTT | 4368 |
| Lys | Ser | Gly | Arg | Gly | Thr | Val | Ser | Leu | Pro | Arg | Leu | Arg | Asn | Phe | Leu |     |
|     |     |     |     | 1445 |     |     |     |     | 1450 |     |     |     |     | 1455 |     |     |
| TAA |     |     |     |     |     |     |     |     |     |     |     |     |     |     |     | 4371 |

( 2 ) INFORMATION FOR SEQ ID NO:2:

( i ) SEQUENCE CHARACTERISTICS:
        ( A ) LENGTH: 1456 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Lys | Val | Arg | Glu | Val | Tyr | Gln | Ser | Phe | Thr | Asp | Ser | Thr | Thr |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Lys | Thr | Leu | Ile | Gln | Asp | Glu | Ala | Tyr | Arg | Asn | Ile | Arg | Pro | Ile | Met |
|     |     |     | 20  |     |     |     |     | 25  |     |     |     |     | 30  |     |     |
| Glu | Lys | His | Lys | Leu | Ala | Asn | Pro | Tyr | Ala | Gln | Thr | Val | Glu | Ala | Ala |
|     |     |     | 35  |     |     |     | 40  |     |     |     |     | 45  |     |     |     |
| Asn | Asp | Leu | Glu | Gly | Phe | Gly | Ile | Ala | Thr | Asn | Pro | Tyr | Ser | Ile | Glu |
|     | 50  |     |     |     |     | 55  |     |     |     |     | 60  |     |     |     |     |
| Leu | His | Thr | His | Ala | Ala | Ala | Lys | Thr | Ile | Glu | Asn | Lys | Leu | Leu | Glu |
| 65  |     |     |     |     | 70  |     |     |     |     | 75  |     |     |     |     | 80  |
| Val | Leu | Gly | Ser | Ile | Leu | Pro | Gln | Glu | Pro | Val | Thr | Phe | Met | Phe | Leu |
|     |     |     |     | 85  |     |     |     |     | 90  |     |     |     |     | 95  |     |
| Lys | Pro | Arg | Lys | Leu | Asn | Tyr | Met | Arg | Arg | Asn | Pro | Arg | Ile | Lys | Asp |
|     |     |     | 100 |     |     |     |     | 105 |     |     |     |     | 110 |     |     |
| Ile | Phe | His | Asn | Val | Ala | Ile | Glu | Pro | Arg | Asp | Val | Ala | Arg | Tyr | Pro |
|     |     |     | 115 |     |     |     | 120 |     |     |     |     | 125 |     |     |     |
| Lys | Glu | Thr | Ile | Ile | Asp | Lys | Leu | Thr | Glu | Ile | Thr | Thr | Asp | Thr | Ala |
|     | 130 |     |     |     |     | 135 |     |     |     |     | 140 |     |     |     |     |
| Tyr | Ile | Ser | Asp | Thr | Leu | His | Phe | Leu | Asp | Pro | Ser | Tyr | Ile | Val | Glu |
| 145 |     |     |     |     | 150 |     |     |     |     | 155 |     |     |     |     | 160 |
| Thr | Phe | Gln | Asn | Cys | Pro | Lys | Leu | Gln | Thr | Leu | Tyr | Ala | Thr | Leu | Val |
|     |     |     |     | 165 |     |     |     |     | 170 |     |     |     |     | 175 |     |
| Leu | Pro | Val | Glu | Ala | Ala | Phe | Lys | Met | Glu | Ser | Thr | His | Pro | Asn | Ile |
|     |     |     | 180 |     |     |     |     | 185 |     |     |     |     | 190 |     |     |
| Tyr | Ser | Leu | Lys | Tyr | Phe | Gly | Asp | Gly | Phe | Gln | Tyr | Ile | Pro | Gly | Asn |
|     |     |     | 195 |     |     |     | 200 |     |     |     |     | 205 |     |     |     |
| His | Gly | Gly | Gly | Ala | Tyr | His | His | Glu | Phe | Ala | His | Leu | Gln | Trp | Leu |
|     |     | 210 |     |     |     |     | 215 |     |     |     |     | 220 |     |     |     |
| Lys | Val | Gly | Lys | Ile | Lys | Trp | Arg | Asp | Pro | Lys | Asp | Ser | Phe | Leu | Gly |
| 225 |     |     |     |     | 230 |     |     |     |     | 235 |     |     |     |     | 240 |
| His | Leu | Asn | Tyr | Thr | Thr | Glu | Gln | Val | Glu | Met | His | Thr | Val | Thr | Val |
|     |     |     |     | 245 |     |     |     |     | 250 |     |     |     |     | 255 |     |
| Gln | Leu | Gln | Glu | Ser | Phe | Ala | Ala | Asn | His | Leu | Tyr | Cys | Ile | Arg | Arg |
|     |     |     | 260 |     |     |     |     | 265 |     |     |     |     | 270 |     |     |
| Gly | Asp | Leu | Leu | Thr | Pro | Glu | Val | Arg | Thr | Phe | Gly | Gln | Pro | Asp | Arg |

-continued

|     |     |     | 275 |     |     |     | 280 |     |     |     | 285 |     |     |
|---|---|---|---|---|---|---|---|---|---|---|---|---|---|

Tyr Val Ile Pro Pro Gln Ile Phe Leu Pro Lys Val His Asn Cys Lys
        290             295             300

Lys Pro Ile Leu Lys Lys Thr Met Met Gln Leu Phe Leu Tyr Val Arg
305             310             315             320

Thr Val Lys Val Ala Lys Asn Cys Asp Ile Phe Ala Lys Val Arg Gln
                325             330             335

Leu Ile Lys Ser Ser Asp Leu Asp Lys Tyr Ser Ala Val Glu Leu Val
            340             345             350

Tyr Leu Val Ser Tyr Met Glu Phe Leu Ala Asp Leu Gln Ala Thr Thr
        355             360             365

Cys Phe Ser Asp Thr Leu Ser Gly Gly Leu Leu Thr Lys Thr Leu Ala
    370             375             380

Pro Val Arg Ala Trp Ile Gln Glu Lys Lys Met Gln Leu Phe Gly Leu
385             390             395             400

Glu Asp Tyr Ala Lys Leu Val Lys Ala Val Asp Phe His Pro Val Asp
                405             410             415

Phe Ser Phe Lys Val Glu Thr Trp Asp Phe Arg Phe His Pro Leu Gln
            420             425             430

Ala Trp Lys Ala Phe Arg Pro Arg Glu Val Ser Asp Val Glu Glu Met
        435             440             445

Glu Ser Leu Phe Ser Asp Gly Asp Leu Leu Asp Cys Phe Thr Arg Met
    450             455             460

Pro Ala Tyr Ala Val Asn Ala Glu Glu Asp Leu Ala Thr Ile Arg Lys
465             470             475             480

Thr Pro Glu Met Asp Val Gly Gln Glu Ala Lys Glu Pro Ala Gly Asp
                485             490             495

Arg Asn Gln Tyr Leu Asn Pro Ala Glu Thr Phe Leu Asn Lys Leu His
            500             505             510

Arg Lys His Ser Arg Glu Val Lys His Gln Ala Val Lys Lys Ala Lys
        515             520             525

Arg Leu Ala Glu Ile Gln Glu Ser Met Arg Ala Glu Gly Glu Ala Glu
    530             535             540

Leu Asn Glu Met Ser Gly Gly Met Arg Ala Ile Pro Ser Asn Ala Glu
545             550             555             560

Leu Pro Ser Thr Asn Asp Ala Arg Gln Leu Thr Leu Pro Thr Thr
                565             570             575

Lys Pro Val Pro Ala Arg Trp Glu Asp Ala Ser Phe Thr Asp Ser Ser
                580             585             590

Val Lys Glu Glu Gln Val Lys Leu Pro Gly Lys Glu Ala Val Glu Thr
        595             600             605

Ala Thr Gln Gln Val Ile Glu Gly Leu Pro Trp Lys His Trp Ile Pro
    610             615             620

Gln Leu Asn Ala Val Gly Phe Lys Ala Leu Glu Ile Gln Arg Asp Arg
625             630             635             640

Ser Gly Thr Met Ile Met Pro Ile Thr Glu Met Val Ser Gly Leu Glu
                645             650             655

Lys Glu Asp Phe Pro Glu Gly Thr Pro Lys Glu Leu Ala Arg Glu Leu
            660             665             670

Leu Ala Met Asn Arg Ser Pro Ala Thr Ile Pro Leu Asp Leu Leu Arg
        675             680             685

Ala Arg Asp Tyr Gly Ser Asp Val Lys Asn Lys Arg Ile Gly Ala Ile
    690             695             700

```
Thr  Lys  Thr  Gln  Ala  Thr  Ser  Trp  Gly  Glu  Tyr  Leu  Thr  Gly  Lys  Ile
705                 710                 715                           720

Glu  Ser  Leu  Thr  Glu  Arg  Lys  Val  Ala  Thr  Cys  Val  Ile  His  Gly  Ala
                    725                 730                      735

Gly  Gly  Ser  Gly  Lys  Ser  His  Ala  Ile  Gln  Lys  Ala  Leu  Arg  Glu  Ile
               740                 745                      750

Gly  Lys  Gly  Ser  Asp  Ile  Thr  Val  Val  Leu  Pro  Thr  Asn  Glu  Leu  Arg
          755                 760                 765

Leu  Asp  Trp  Ser  Lys  Lys  Val  Pro  Asn  Thr  Glu  Pro  Tyr  Met  Phe  Lys
770                      775                      780

Thr  Tyr  Glu  Lys  Ala  Leu  Ile  Gly  Gly  Thr  Gly  Ser  Ile  Val  Ile  Phe
785                 790                 795                           800

Asp  Asp  Tyr  Ser  Lys  Leu  Pro  Pro  Gly  Tyr  Ile  Glu  Ala  Leu  Ile  Cys
               805                 810                           815

Phe  Tyr  Ser  Lys  Ile  Lys  Leu  Val  Ile  Leu  Thr  Gly  Asp  Ser  Arg  Gln
               820                 825                 830

Ser  Val  Tyr  His  Glu  Thr  Ala  Glu  Asp  Ala  Ser  Ile  Arg  His  Leu  Gly
          835                 840                      845

Pro  Ala  Thr  Glu  Tyr  Phe  Ser  Lys  Tyr  Cys  Arg  Tyr  Tyr  Leu  Asn  Ala
850                      855                 860

Thr  His  Arg  Asn  Lys  Lys  Asp  Leu  Ala  Asn  Met  Leu  Gly  Val  Tyr  Ser
865                 870                 875                           880

Glu  Arg  Thr  Gly  Val  Thr  Glu  Ile  Ser  Met  Ser  Ala  Glu  Phe  Leu  Glu
               885                 890                           895

Gly  Ile  Pro  Thr  Leu  Val  Pro  Ser  Asp  Glu  Lys  Arg  Lys  Leu  Tyr  Met
               900                 905                      910

Gly  Thr  Gly  Arg  Asn  Asp  Thr  Phe  Thr  Tyr  Ala  Gly  Cys  Gln  Gly  Leu
          915                 920                      925

Thr  Lys  Pro  Lys  Val  Gln  Ile  Val  Leu  Asp  His  Asn  Thr  Gln  Val  Cys
          930                 935                 940

Ser  Ala  Asn  Val  Met  Tyr  Thr  Ala  Leu  Ser  Arg  Ala  Thr  Asp  Arg  Ile
945                 950                 955                           960

His  Phe  Val  Asn  Thr  Ser  Ala  Asn  Ser  Ser  Ala  Phe  Trp  Glu  Lys  Leu
               965                 970                           975

Asp  Ser  Thr  Pro  Tyr  Leu  Lys  Thr  Phe  Leu  Ser  Val  Val  Arg  Glu  Gln
               980                 985                      990

Ala  Leu  Arg  Glu  Tyr  Glu  Pro  Ala  Glu  Ala  Glu  Pro  Ile  Arg  Glu  Pro
          995                 1000                1005

Glu  Pro  Gln  Thr  His  Met  Cys  Val  Glu  Asn  Glu  Glu  Ser  Val  Leu  Glu
     1010                1015                1020

Glu  Tyr  Lys  Glu  Glu  Leu  Leu  Glu  Lys  Phe  Asp  Arg  Glu  Ile  His  Ser
1025                1030                1035                          1040

Glu  Ser  His  Gly  His  Ser  Asn  Cys  Val  Gln  Thr  Glu  Asp  Thr  Thr  Ile
               1045                1050                     1055

Gln  Leu  Phe  Ser  His  Gln  Gln  Ala  Lys  Asp  Glu  Thr  Leu  Leu  Trp  Ala
               1060                1065                          1070

Thr  Ile  Asp  Ala  Arg  Leu  Lys  Ile  Ser  Asn  Gln  Glu  Thr  Asn  Phe  Arg
          1075                1080                     1085

Glu  Phe  Leu  Ser  Lys  Lys  Asp  Ile  Gly  Asp  Val  Leu  Phe  Leu  Asn  Tyr
     1090                1095                     1100

Gln  Lys  Ala  Met  Gly  Leu  Pro  Lys  Glu  Arg  Ile  Pro  Phe  Ser  Gln  Glu
1105                1110                1115                          1120

Val  Trp  Glu  Ala  Cys  Ala  His  Glu  Val  Gln  Ser  Lys  Tyr  Leu  Ser  Lys
               1125                1130                          1135
```

| | | | | | | | | | | | | | | |
|---|---|---|---|---|---|---|---|---|---|---|---|---|---|---|
| Ser | Lys | Cys | Asn | Leu | Ile | Asn | Gly | Thr | Val | Arg | Gln | Ser | Pro | Asp | Phe |
| | | | 1140 | | | | 1145 | | | | | 1150 | | | |
| Asp | Glu | Asn | Lys | Ile | Met | Val | Phe | Leu | Lys | Ser | Gln | Trp | Val | Thr | Lys |
| | | | 1155 | | | | 1160 | | | | | 1165 | | | |
| Val | Glu | Lys | Leu | Gly | Leu | Pro | Lys | Ile | Lys | Pro | Gly | Gln | Thr | Ile | Ala |
| | 1170 | | | | | 1175 | | | | | | 1180 | | | |
| Ala | Phe | Tyr | Gln | Gln | Thr | Val | Met | Leu | Phe | Gly | Thr | Met | Ala | Arg | Tyr |
| 1185 | | | | | 1190 | | | | | 1195 | | | | | 1200 |
| Met | Arg | Trp | Phe | Arg | Gln | Ala | Phe | Gln | Pro | Lys | Glu | Val | Phe | Ile | Asn |
| | | | | 1205 | | | | | 1210 | | | | | 1215 | |
| Cys | Glu | Thr | Thr | Pro | Glu | Asp | Met | Ser | Ala | Trp | Ala | Leu | Asn | Asn | Trp |
| | | | | 1220 | | | | | 1225 | | | | | 1230 | |
| Asn | Phe | Gly | Arg | Pro | Ser | Leu | Ala | Asn | Asp | Tyr | Thr | Ala | Phe | Asp | Gln |
| | | | | 1235 | | | | | 1240 | | | | | 1245 | |
| Ser | Gln | Asp | Gly | Ala | Met | Leu | Gln | Phe | Glu | Val | Leu | Lys | Ala | Lys | His |
| | | 1250 | | | | | 1255 | | | | | 1260 | | | |
| His | Cys | Ile | Pro | Glu | Glu | Ile | Ile | Gln | Ala | Tyr | Ile | Asp | Ile | Lys | Thr |
| 1265 | | | | | 1270 | | | | | 1275 | | | | | 1280 |
| Asn | Ala | Gln | Ile | Phe | Leu | Gly | Thr | Leu | Ser | Ile | Met | Arg | Leu | Thr | Gly |
| | | | | 1285 | | | | | 1290 | | | | | 1295 | |
| Glu | Gly | Pro | Thr | Phe | Asp | Ala | Asn | Thr | Glu | Cys | Asn | Ile | Ala | Tyr | Thr |
| | | | | 1300 | | | | | 1305 | | | | | 1310 | |
| His | Thr | Lys | Phe | Asp | Ile | Pro | Ala | Gly | Thr | Ala | Gln | Val | Tyr | Ala | Gly |
| | | | 1315 | | | | | 1320 | | | | | 1325 | | |
| Asp | Asp | Ser | Ala | Leu | Asp | Cys | Val | Pro | Glu | Val | Lys | His | Ser | Phe | His |
| | | 1330 | | | | | 1335 | | | | | 1340 | | | |
| Arg | Leu | Glu | Asp | Lys | Leu | Leu | Leu | Lys | Ser | Lys | Pro | Val | Ile | Thr | Gln |
| 1345 | | | | | 1350 | | | | | 1355 | | | | | 1360 |
| Gln | Lys | Lys | Gly | Ser | Trp | Pro | Glu | Phe | Cys | Gly | Trp | Leu | Ile | Thr | Pro |
| | | | | 1365 | | | | | 1370 | | | | | 1375 | |
| Lys | Gly | Val | Met | Lys | Asp | Pro | Ile | Lys | Leu | His | Val | Ser | Leu | Lys | Leu |
| | | | 1380 | | | | | 1385 | | | | | 1390 | | |
| Ala | Glu | Ala | Lys | Gly | Glu | Leu | Lys | Lys | Cys | Gln | Asp | Ser | Tyr | Glu | Ile |
| | | | 1395 | | | | | 1400 | | | | | 1405 | | |
| Asp | Leu | Ser | Tyr | Ala | Tyr | Asp | His | Lys | Asp | Ser | Leu | His | Asp | Leu | Phe |
| | | | 1410 | | | | | 1415 | | | | | 1420 | | |
| Asp | Glu | Lys | Gln | Cys | Gln | Ala | His | Thr | Leu | Thr | Cys | Arg | Thr | Leu | Ile |
| 1425 | | | | | 1430 | | | | | 1435 | | | | | 1440 |
| Lys | Ser | Gly | Arg | Gly | Thr | Val | Ser | Leu | Pro | Arg | Leu | Arg | Asn | Phe | Leu |
| | | | | 1445 | | | | | 1450 | | | | | 1455 | |

( 2 ) INFORMATION FOR SEQ ID NO:3:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
GAAAACTAAA CCATACACCA CCAACACAAC CAAACCCACC ACGCCCAATT GTTACACACC      60
CGCTTGAAAA AGCAAGTCTG ACAA                                            84
```

( 2 ) INFORMATION FOR SEQ ID NO:4:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:4:

```
TATGGTTTAG TTTTCGAGCT CTATAGTGAG TCGTAT                                    36
```

( 2 ) INFORMATION FOR SEQ ID NO:5:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:5:

```
GGTAACTTAA CGGGAGCTCT TAAAGAAAGT TTC                                       33
```

( 2 ) INFORMATION FOR SEQ ID NO:6:

( i ) SEQUENCE CHARACTERISTICS:
    ( A ) LENGTH: 2022 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..2022

( x i ) SEQUENCE DESCRIPTION: SEQ ID NO:6:

```
ATG  GCC  AAA  GTG  CGC  GAG  GTT  TAC  CAA  TCC  TTT  ACA  GAC  TCC  ACC  ACA     48
Met  Ala  Lys  Val  Arg  Glu  Val  Tyr  Gln  Ser  Phe  Thr  Asp  Ser  Thr  Thr
 1                  5                   10                  15

AAA  ACT  CTC  ATC  CAA  GAT  GAG  GCT  TAT  AGA  AAT  ATT  CGT  CCC  ATC  ATG     96
Lys  Thr  Leu  Ile  Gln  Asp  Glu  Ala  Tyr  Arg  Asn  Ile  Arg  Pro  Ile  Met
                 20                  25                  30

GAA  AAA  CAT  AAA  CTA  GCT  AAC  CCG  TAC  GCT  CAA  ACG  GTT  GAA  GCG  GCT    144
Glu  Lys  His  Lys  Leu  Ala  Asn  Pro  Tyr  Ala  Gln  Thr  Val  Glu  Ala  Ala
             35                  40                  45

AAT  GAT  CTA  GAG  GGG  TTC  GGC  ATA  GCC  ACC  AAT  CCC  TAT  AGC  ATT  GAG    192
Asn  Asp  Leu  Glu  Gly  Phe  Gly  Ile  Ala  Thr  Asn  Pro  Tyr  Ser  Ile  Glu
         50                  55                  60

TTG  CAT  ACA  CAT  GCA  GCT  GCT  AAG  ACC  ATA  GAG  AAT  AAA  CTT  CTA  GAG    240
Leu  His  Thr  His  Ala  Ala  Ala  Lys  Thr  Ile  Glu  Asn  Lys  Leu  Leu  Glu
 65                  70                  75                  80

GTG  CTT  GGT  TCC  ATC  CTA  CCA  CAA  GAA  CCT  GTT  ACA  TTT  ATG  TTC  CTT    288
Val  Leu  Gly  Ser  Ile  Leu  Pro  Gln  Glu  Pro  Val  Thr  Phe  Met  Phe  Leu
                 85                  90                  95

AAA  CCC  AGG  AAG  CTA  AAC  TAC  ATG  AGA  AGA  AAC  CCG  CGG  ATC  AAG  GAC    336
Lys  Pro  Arg  Lys  Leu  Asn  Tyr  Met  Arg  Arg  Asn  Pro  Arg  Ile  Lys  Asp
             100                 105                 110

ATT  TTC  CAC  AAT  GTT  GCC  ATT  GAA  CCG  AGA  GAC  GTA  GCA  AGG  TAC  CCC    384
Ile  Phe  His  Asn  Val  Ala  Ile  Glu  Pro  Arg  Asp  Val  Ala  Arg  Tyr  Pro
         115                 120                 125

AAG  GAA  ACA  ATA  ATT  GAC  AAA  CTC  ACA  GAG  ATC  ACA  ACA  GAC  ACA  GCA    432
Lys  Glu  Thr  Ile  Ile  Asp  Lys  Leu  Thr  Glu  Ile  Thr  Thr  Asp  Thr  Ala
 130                 135                 140
```

| | | | | | | | | | | | | | | | | |
|---|---|---|---|---|---|---|---|---|---|---|---|---|---|---|---|---|
| TAC | ATT | AGT | GAC | ACT | CTG | CAC | TTC | TTG | GAT | CCG | AGC | TAC | ATA | GTG | GAG | 480 |
| Tyr | Ile | Ser | Asp | Thr | Leu | His | Phe | Leu | Asp | Pro | Ser | Tyr | Ile | Val | Glu | |
| 145 | | | | 150 | | | | | 155 | | | | | | 160 | |
| ACA | TTC | CAA | AAC | TGC | CCA | AAA | CTG | CAA | ACA | TTG | TAT | GCG | ACC | TTA | GTT | 528 |
| Thr | Phe | Gln | Asn | Cys | Pro | Lys | Leu | Gln | Thr | Leu | Tyr | Ala | Thr | Leu | Val | |
| | | | | 165 | | | | | 170 | | | | | 175 | | |
| CTC | CCC | GTT | GAG | GCA | GCC | TTC | AAA | ATG | GAA | AGC | ACT | CAC | CCG | AAC | ATA | 576 |
| Leu | Pro | Val | Glu | Ala | Ala | Phe | Lys | Met | Glu | Ser | Thr | His | Pro | Asn | Ile | |
| | | | 180 | | | | | 185 | | | | | 190 | | | |
| TAC | AGC | CTC | AAA | TAC | TTC | GGA | GAT | GGT | TTC | CAG | TAT | ATA | CCA | GGC | AAC | 624 |
| Tyr | Ser | Leu | Lys | Tyr | Phe | Gly | Asp | Gly | Phe | Gln | Tyr | Ile | Pro | Gly | Asn | |
| | | 195 | | | | | 200 | | | | | 205 | | | | |
| CAT | GGT | GGT | GGA | GCG | TAC | CAT | CAT | GAA | TTT | GCT | CAT | TTA | CAA | TGG | CTC | 672 |
| His | Gly | Gly | Gly | Ala | Tyr | His | His | Glu | Phe | Ala | His | Leu | Gln | Trp | Leu | |
| | 210 | | | | | 215 | | | | | 220 | | | | | |
| AAA | GTG | GGA | AAG | ATC | AAA | TGG | AGG | GAC | CCC | AAG | GAT | AGC | TTT | CTC | GGA | 720 |
| Lys | Val | Gly | Lys | Ile | Lys | Trp | Arg | Asp | Pro | Lys | Asp | Ser | Phe | Leu | Gly | |
| 225 | | | | | 230 | | | | | 235 | | | | | 240 | |
| CAT | CTC | AAT | TAC | ACG | ACT | GAG | CAG | GTT | GAG | ATG | CAC | ACA | GTG | ACA | GTG | 768 |
| His | Leu | Asn | Tyr | Thr | Thr | Glu | Gln | Val | Glu | Met | His | Thr | Val | Thr | Val | |
| | | | | 245 | | | | | 250 | | | | | 255 | | |
| CAG | TTG | CAG | GAA | TCG | TTC | GCG | GCA | AAC | CAC | TTG | TAC | TGC | ATC | AGG | AGA | 816 |
| Gln | Leu | Gln | Glu | Ser | Phe | Ala | Ala | Asn | His | Leu | Tyr | Cys | Ile | Arg | Arg | |
| | | | 260 | | | | | 265 | | | | | 270 | | | |
| GGA | GAT | TTG | CTC | ACA | CCG | GAG | GTG | CGC | ACT | TTT | GGC | CAA | CCT | GAC | AGG | 864 |
| Gly | Asp | Leu | Leu | Thr | Pro | Glu | Val | Arg | Thr | Phe | Gly | Gln | Pro | Asp | Arg | |
| | | 275 | | | | | 280 | | | | | 285 | | | | |
| TAT | GTG | ATT | CCA | CCA | CAG | ATC | TTC | CTC | CCG | AAA | GTC | CAT | AAC | TGC | AAG | 912 |
| Tyr | Val | Ile | Pro | Pro | Gln | Ile | Phe | Leu | Pro | Lys | Val | His | Asn | Cys | Lys | |
| | 290 | | | | | 295 | | | | | 300 | | | | | |
| AAG | CCG | ATT | CTT | AAA | AAA | ACT | ATG | ATG | CAG | CTC | TTC | TTG | TAT | GTT | AGG | 960 |
| Lys | Pro | Ile | Leu | Lys | Lys | Thr | Met | Met | Gln | Leu | Phe | Leu | Tyr | Val | Arg | |
| 305 | | | | | 310 | | | | | 315 | | | | | 320 | |
| ACA | GTT | AAG | GTC | GCA | AAA | AAT | TGT | GAC | ATT | TTT | GCC | AAA | GTC | AGA | CAA | 1008 |
| Thr | Val | Lys | Val | Ala | Lys | Asn | Cys | Asp | Ile | Phe | Ala | Lys | Val | Arg | Gln | |
| | | | | 325 | | | | | 330 | | | | | 335 | | |
| TTA | ATT | AAA | TCA | TCT | GAC | CTG | GAC | AAA | TAT | TCT | GCT | GTG | GAA | CTG | GTT | 1056 |
| Leu | Ile | Lys | Ser | Ser | Asp | Leu | Asp | Lys | Tyr | Ser | Ala | Val | Glu | Leu | Val | |
| | | | | 340 | | | | | 345 | | | | | 350 | | |
| TAC | TTA | GTA | AGC | TAT | ATG | GAG | TTC | CTT | GCC | GAT | CTA | CAA | GCT | ACC | ACC | 1104 |
| Tyr | Leu | Val | Ser | Tyr | Met | Glu | Phe | Leu | Ala | Asp | Leu | Gln | Ala | Thr | Thr | |
| | | 355 | | | | | 360 | | | | | 365 | | | | |
| TGC | TTC | TCA | GAC | ACA | CTT | TCT | GGT | GGC | TTA | CTA | ACA | AAG | ACC | CTT | GCA | 1152 |
| Cys | Phe | Ser | Asp | Thr | Leu | Ser | Gly | Gly | Leu | Leu | Thr | Lys | Thr | Leu | Ala | |
| | 370 | | | | | 375 | | | | | 380 | | | | | |
| CCG | GTG | AGG | GCT | TGG | ATA | CAA | GAG | AAA | AAG | ATG | CAG | CTG | TTT | GGT | CTT | 1200 |
| Pro | Val | Arg | Ala | Trp | Ile | Gln | Glu | Lys | Lys | Met | Gln | Leu | Phe | Gly | Leu | |
| 385 | | | | | 390 | | | | | 395 | | | | | 400 | |
| GAG | GAC | TAC | GCG | AAG | TTA | GTC | AAA | GCA | GTT | GAT | TTC | CAC | CCA | GTG | GAT | 1248 |
| Glu | Asp | Tyr | Ala | Lys | Leu | Val | Lys | Ala | Val | Asp | Phe | His | Pro | Val | Asp | |
| | | | | 405 | | | | | 410 | | | | | 415 | | |
| TTT | TCT | TTT | AAA | GTT | GAA | ACT | TGG | GAC | TTC | AGA | TTC | CAC | CCC | TTG | CAA | 1296 |
| Phe | Ser | Phe | Lys | Val | Glu | Thr | Trp | Asp | Phe | Arg | Phe | His | Pro | Leu | Gln | |
| | | | 420 | | | | | 425 | | | | | 430 | | | |
| GCG | TGG | AAA | GCC | TTC | CGA | CCA | AGG | GAA | GTG | TCG | GAT | GTA | GAG | GAA | ATG | 1344 |
| Ala | Trp | Lys | Ala | Phe | Arg | Pro | Arg | Glu | Val | Ser | Asp | Val | Glu | Glu | Met | |
| | | 435 | | | | | 440 | | | | | 445 | | | | |
| GAA | AGT | TTG | TTC | TCA | GAT | GGG | GAC | CTG | CTT | GAC | TGC | TTC | ACA | AGA | ATG | 1392 |
| Glu | Ser | Leu | Phe | Ser | Asp | Gly | Asp | Leu | Leu | Asp | Cys | Phe | Thr | Arg | Met | |
| | 450 | | | | | 455 | | | | | 460 | | | | | |

| | | | | | | | | | | | | | | | | |
|---|---|---|---|---|---|---|---|---|---|---|---|---|---|---|---|---|
| CCA | GCT | TAT | GCA | GTA | AAC | GCA | GAG | GAA | GAT | TTA | GCT | ACA | ATC | AGG | AAA | 1440 |
| Pro | Ala | Tyr | Ala | Val | Asn | Ala | Glu | Glu | Asp | Leu | Ala | Thr | Ile | Arg | Lys | |
| 465 | | | | 470 | | | | | 475 | | | | | | 480 | |
| ACG | CCC | GAG | ATG | GAT | GTC | GGT | CAA | GAA | GCC | AAA | GAA | CCT | GCA | GGA | GAC | 1488 |
| Thr | Pro | Glu | Met | Asp | Val | Gly | Gln | Glu | Ala | Lys | Glu | Pro | Ala | Gly | Asp | |
| | | | | 485 | | | | | 490 | | | | | 495 | | |
| AGA | AAT | CAA | TAC | TTA | AAC | CCT | GCA | GAA | ACT | TTC | CTC | AAC | AAG | CTC | CAC | 1536 |
| Arg | Asn | Gln | Tyr | Leu | Asn | Pro | Ala | Glu | Thr | Phe | Leu | Asn | Lys | Leu | His | |
| | | | 500 | | | | | 505 | | | | | 510 | | | |
| AGG | AAA | CAC | AGT | AGG | GAG | GTG | AAA | CAT | CAG | GCC | GTA | AAG | AAA | GCT | AAA | 1584 |
| Arg | Lys | His | Ser | Arg | Glu | Val | Lys | His | Gln | Ala | Val | Lys | Lys | Ala | Lys | |
| | | 515 | | | | | 520 | | | | | 525 | | | | |
| CGC | CTA | GCT | GAA | ATC | CAG | GAG | TCC | ATG | AGA | GCT | GAG | GGT | GAG | GCC | GAA | 1632 |
| Arg | Leu | Ala | Glu | Ile | Gln | Glu | Ser | Met | Arg | Ala | Glu | Gly | Glu | Ala | Glu | |
| | 530 | | | | | 535 | | | | | 540 | | | | | |
| CTA | AAT | GAG | ATG | AGC | GGG | GGC | ATG | AGG | GCA | ATA | CCT | AGC | AAC | GCA | GAA | 1680 |
| Leu | Asn | Glu | Met | Ser | Gly | Gly | Met | Arg | Ala | Ile | Pro | Ser | Asn | Ala | Glu | |
| 545 | | | | | 550 | | | | | 555 | | | | | 560 | |
| CTT | CCC | AGC | ACG | AAC | GAT | GCT | AGA | CAA | GAA | CTC | ACA | CTC | CCA | ACC | ACT | 1728 |
| Leu | Pro | Ser | Thr | Asn | Asp | Ala | Arg | Gln | Glu | Leu | Thr | Leu | Pro | Thr | Thr | |
| | | | | 565 | | | | | 570 | | | | | 575 | | |
| AAA | CCT | GTC | CCT | GCA | AGG | TGG | GAA | GAT | GCT | TCA | TTC | ACA | GAT | TCT | AGT | 1776 |
| Lys | Pro | Val | Pro | Ala | Arg | Trp | Glu | Asp | Ala | Ser | Phe | Thr | Asp | Ser | Ser | |
| | | | 580 | | | | | 585 | | | | | 590 | | | |
| GTG | AAA | GAG | GAG | CAA | GTG | AAA | CTC | CCT | GGA | AAA | GAA | GCC | GTT | GAG | ACA | 1824 |
| Val | Lys | Glu | Glu | Gln | Val | Lys | Leu | Pro | Gly | Lys | Glu | Ala | Val | Glu | Thr | |
| | | 595 | | | | | 600 | | | | | 605 | | | | |
| GCG | ACG | CAA | CAA | GTC | ATA | GAA | GGA | CTC | CCT | TGG | AAA | CAC | TGG | ATT | CCT | 1872 |
| Ala | Thr | Gln | Gln | Val | Ile | Glu | Gly | Leu | Pro | Trp | Lys | His | Trp | Ile | Pro | |
| | 610 | | | | | 615 | | | | | 620 | | | | | |
| CAA | CTA | AAT | GCT | GTT | GGA | TTC | AAG | GCG | CTG | GAA | ATT | CAG | AGG | GAT | AGG | 1920 |
| Gln | Leu | Asn | Ala | Val | Gly | Phe | Lys | Ala | Leu | Glu | Ile | Gln | Arg | Asp | Arg | |
| 625 | | | | | 630 | | | | | 635 | | | | | 640 | |
| AGT | GGG | ACA | ATG | ATC | ATG | CCC | ATC | ACA | GAA | ATG | GTC | TCC | GGG | TTG | GAA | 1968 |
| Ser | Gly | Thr | Met | Ile | Met | Pro | Ile | Thr | Glu | Met | Val | Ser | Gly | Leu | Glu | |
| | | | | 645 | | | | | 650 | | | | | 655 | | |
| AAA | GAG | GAC | TTC | CCG | GAA | GGA | ACT | CCA | AAA | GAG | TTG | GCA | CGA | GAA | TTG | 2016 |
| Lys | Glu | Asp | Phe | Pro | Glu | Gly | Thr | Pro | Lys | Glu | Leu | Ala | Arg | Glu | Leu | |
| | | | 660 | | | | | 665 | | | | | 670 | | | |
| CTC | GCT | | | | | | | | | | | | | | | 2022 |
| Leu | Ala | | | | | | | | | | | | | | | |

( 2 ) INFORMATION FOR SEQ ID NO:7:

( i ) SEQUENCE CHARACTERISTICS:
        ( A ) LENGTH: 674 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | |
|---|---|---|---|---|---|---|---|---|---|---|---|---|---|---|
| Met | Ala | Lys | Val | Arg | Glu | Val | Tyr | Gln | Ser | Phe | Thr | Asp | Ser | Thr |
| 1 | | | | 5 | | | | | 10 | | | | | 15 |
| Lys | Thr | Leu | Ile | Gln | Asp | Glu | Ala | Tyr | Arg | Asn | Ile | Arg | Pro | Ile | Met |
| | | | 20 | | | | | 25 | | | | | 30 | | |
| Glu | Lys | His | Lys | Leu | Ala | Asn | Pro | Tyr | Ala | Gln | Thr | Val | Glu | Ala | Ala |
| | | 35 | | | | | 40 | | | | | 45 | | | |
| Asn | Asp | Leu | Glu | Gly | Phe | Gly | Ile | Ala | Thr | Asn | Pro | Tyr | Ser | Ile | Glu |
| | 50 | | | | | 55 | | | | | 60 | | | | |

```
Leu His Thr His Ala Ala Ala Lys Thr Ile Glu Asn Lys Leu Leu Glu
 65                  70                  75                  80

Val Leu Gly Ser Ile Leu Pro Gln Glu Pro Val Thr Phe Met Phe Leu
                 85                  90                  95

Lys Pro Arg Lys Leu Asn Tyr Met Arg Arg Asn Pro Arg Ile Lys Asp
            100                 105                 110

Ile Phe His Asn Val Ala Ile Glu Pro Arg Asp Val Ala Arg Tyr Pro
        115                 120                 125

Lys Glu Thr Ile Ile Asp Lys Leu Thr Glu Ile Thr Asp Thr Ala
    130                 135                 140

Tyr Ile Ser Asp Thr Leu His Phe Leu Asp Pro Ser Tyr Ile Val Glu
145                 150                 155                 160

Thr Phe Gln Asn Cys Pro Lys Leu Gln Thr Leu Tyr Ala Thr Leu Val
                165                 170                 175

Leu Pro Val Glu Ala Ala Phe Lys Met Glu Ser Thr His Pro Asn Ile
            180                 185                 190

Tyr Ser Leu Lys Tyr Phe Gly Asp Gly Phe Gln Tyr Ile Pro Gly Asn
        195                 200                 205

His Gly Gly Gly Ala Tyr His His Glu Phe Ala His Leu Gln Trp Leu
    210                 215                 220

Lys Val Gly Lys Ile Lys Trp Arg Asp Pro Lys Asp Ser Phe Leu Gly
225                 230                 235                 240

His Leu Asn Tyr Thr Thr Glu Gln Val Glu Met His Thr Val Thr Val
                245                 250                 255

Gln Leu Gln Glu Ser Phe Ala Ala Asn His Leu Tyr Cys Ile Arg Arg
            260                 265                 270

Gly Asp Leu Leu Thr Pro Glu Val Arg Thr Phe Gly Gln Pro Asp Arg
        275                 280                 285

Tyr Val Ile Pro Pro Gln Ile Phe Leu Pro Lys Val His Asn Cys Lys
290                 295                 300

Lys Pro Ile Leu Lys Lys Thr Met Met Gln Leu Phe Leu Tyr Val Arg
305                 310                 315                 320

Thr Val Lys Val Ala Lys Asn Cys Asp Ile Phe Ala Lys Val Arg Gln
                325                 330                 335

Leu Ile Lys Ser Ser Asp Leu Asp Lys Tyr Ser Ala Val Glu Leu Val
            340                 345                 350

Tyr Leu Val Ser Tyr Met Glu Phe Leu Ala Asp Leu Gln Ala Thr Thr
        355                 360                 365

Cys Phe Ser Asp Thr Leu Ser Gly Gly Leu Leu Thr Lys Thr Leu Ala
    370                 375                 380

Pro Val Arg Ala Trp Ile Gln Glu Lys Lys Met Gln Leu Phe Gly Leu
385                 390                 395                 400

Glu Asp Tyr Ala Lys Leu Val Lys Ala Val Asp Phe His Pro Val Asp
                405                 410                 415

Phe Ser Phe Lys Val Glu Thr Trp Asp Phe Arg Phe His Pro Leu Gln
            420                 425                 430

Ala Trp Lys Ala Phe Arg Pro Arg Glu Val Ser Asp Val Glu Glu Met
        435                 440                 445

Glu Ser Leu Phe Ser Asp Gly Asp Leu Leu Asp Cys Phe Thr Arg Met
    450                 455                 460

Pro Ala Tyr Ala Val Asn Ala Glu Glu Asp Leu Ala Thr Ile Arg Lys
465                 470                 475                 480

Thr Pro Glu Met Asp Val Gly Gln Glu Ala Lys Glu Pro Ala Gly Asp
                485                 490                 495
```

```
Arg  Asn  Gln  Tyr  Leu  Asn  Pro  Ala  Glu  Thr  Phe  Leu  Asn  Lys  Leu  His
               500                 505                           510

Arg  Lys  His  Ser  Arg  Glu  Val  Lys  His  Gln  Ala  Val  Lys  Lys  Ala  Lys
          515                      520                      525

Arg  Leu  Ala  Glu  Ile  Gln  Glu  Ser  Met  Arg  Ala  Glu  Gly  Glu  Ala  Glu
          530                      535                      540

Leu  Asn  Glu  Met  Ser  Gly  Gly  Met  Arg  Ala  Ile  Pro  Ser  Asn  Ala  Glu
545                      550                      555                      560

Leu  Pro  Ser  Thr  Asn  Asp  Ala  Arg  Gln  Glu  Leu  Thr  Leu  Pro  Thr  Thr
               565                      570                      575

Lys  Pro  Val  Pro  Ala  Arg  Trp  Glu  Asp  Ala  Ser  Phe  Thr  Asp  Ser  Ser
               580                      585                      590

Val  Lys  Glu  Glu  Gln  Val  Lys  Leu  Pro  Gly  Lys  Glu  Ala  Val  Glu  Thr
          595                      600                      605

Ala  Thr  Gln  Gln  Val  Ile  Glu  Gly  Leu  Pro  Trp  Lys  His  Trp  Ile  Pro
     610                      615                      620

Gln  Leu  Asn  Ala  Val  Gly  Phe  Lys  Ala  Leu  Glu  Ile  Gln  Arg  Asp  Arg
625                      630                      635                      640

Ser  Gly  Thr  Met  Ile  Met  Pro  Ile  Thr  Glu  Met  Val  Ser  Gly  Leu  Glu
               645                      650                      655

Lys  Glu  Asp  Phe  Pro  Glu  Gly  Thr  Pro  Lys  Glu  Leu  Ala  Arg  Glu  Leu
               660                      665                      670

Leu  Ala
```

(2) INFORMATION FOR SEQ ID NO:8:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:8:

GAATTGCTCG CTTAAGAGCT CATGAACAGA AGCC                                    34

(2) INFORMATION FOR SEQ ID NO:9:

(i) SEQUENCE CHARACTERISTICS:
      (A) LENGTH: 597 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:9:

TCATCAAAAT ATTTAGCAGC ATTCCAGATT GGGTTCAATC AACAAGGTAC GAGCCATATC        60
ACTTTATTCA AATTGGTATC GCCAAAACCA AGAAGGAACT CCCATCCTCA AAGGTTTGTA       120
AGGAAGAATT CTCAGTCCAA AGCCTCAACA AGGTCAGGGT ACAGAGTCTC CAAACCATTA       180
GCCAAAAGCT ACAGGAGATC AATGAAGAAT CTTCAATCAA AGTAAACTAC TGTTCCAGCA       240
CATGCATCAT GGTCAGTAAG TTTCAGAAAA AGACATCCAC CGAAGACTTA AAGTTAGTGG       300
GCATCTTTGA AAGTAATCTT GTCAACATCG AGCAGCTGGC TTGTGGGGAC AGACAAAAA       360
AGGAATGGTG CAGAATTGTT AGGCGCACCT ACCAAAGCA TCTTTGCCTT TATTGCAAAG        420
ATAAAGCAGA TTCCTCTAGT ACAAGTGGGG AACAAAATAA CGTGGAAAAG AGCTGTCCTG       480

| | | | | | | | | | | | | |
|---|---|---|---|---|---|---|---|---|---|---|---|---|
| ACAGCCCACT | CACTAATGCG | TATGACGAAC | GCAGTGACGA | CCACAAAAGA | ATTCCCTCTA | | | | | | | 540 |
| TATAAGAAGG | CATTCATTCC | CATTTGAAGG | ATCATCAGAT | ACTAACCAAT | ATTTCTC | | | | | | | 597 |

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

GAATTGCTCG CTAAGAGCTC ATGAACAGAA GCC        33

( 2 ) INFORMATION FOR SEQ ID NO:11:

( i ) SEQUENCE CHARACTERISTICS:
        ( A ) LENGTH: 2124 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..2124

( x i ) SEQUENCE DESCRIPTION: SEQ ID NO:11:

| | | | | | | | | | | | | | | | | |
|---|---|---|---|---|---|---|---|---|---|---|---|---|---|---|---|---|
| ATG | GCC | AAA | GTG | CGC | GAG | GTT | TAC | CAA | TCC | TTT | ACA | GAC | TCC | ACC | ACA | 48 |
| Met | Ala | Lys | Val | Arg | Glu | Val | Tyr | Gln | Ser | Phe | Thr | Asp | Ser | Thr | Thr | |
| 1 | | | | 5 | | | | | 10 | | | | | 15 | | |
| AAA | ACT | CTC | ATC | CAA | GAT | GAG | GCT | TAT | AGA | AAT | ATT | CGT | CCC | ATC | ATG | 96 |
| Lys | Thr | Leu | Ile | Gln | Asp | Glu | Ala | Tyr | Arg | Asn | Ile | Arg | Pro | Ile | Met | |
| | | | 20 | | | | | 25 | | | | | 30 | | | |
| GAA | AAA | CAT | AAA | CTA | GCT | AAC | CCG | TAC | GCT | CAA | ACG | GTT | GAA | GCG | GCT | 144 |
| Glu | Lys | His | Lys | Leu | Ala | Asn | Pro | Tyr | Ala | Gln | Thr | Val | Glu | Ala | Ala | |
| | | 35 | | | | | 40 | | | | | 45 | | | | |
| AAT | GAT | CTA | GAG | GGG | TTC | GGC | ATA | GCC | ACC | AAT | CCC | TAT | AGC | ATT | GAG | 192 |
| Asn | Asp | Leu | Glu | Gly | Phe | Gly | Ile | Ala | Thr | Asn | Pro | Tyr | Ser | Ile | Glu | |
| | 50 | | | | | 55 | | | | | 60 | | | | | |
| TTG | CAT | ACA | CAT | GCA | GCT | GCT | AAG | ACC | ATA | GAG | AAT | AAA | CTT | CTA | GAG | 240 |
| Leu | His | Thr | His | Ala | Ala | Ala | Lys | Thr | Ile | Glu | Asn | Lys | Leu | Leu | Glu | |
| 65 | | | | | 70 | | | | | 75 | | | | | 80 | |
| GTG | CTT | GGT | TCC | ATC | CTA | CCA | CAA | GAA | CCT | GTT | ACA | TTT | ATG | TTC | CTT | 288 |
| Val | Leu | Gly | Ser | Ile | Leu | Pro | Gln | Glu | Pro | Val | Thr | Phe | Met | Phe | Leu | |
| | | | | 85 | | | | | 90 | | | | | 95 | | |
| AAA | CCC | AGG | AAG | CTA | AAC | TAC | ATG | AGA | AGA | AAC | CCG | CGG | ATC | AAG | GAC | 336 |
| Lys | Pro | Arg | Lys | Leu | Asn | Tyr | Met | Arg | Arg | Asn | Pro | Arg | Ile | Lys | Asp | |
| | | | 100 | | | | | 105 | | | | | 110 | | | |
| ATT | TTC | CAC | AAT | GTT | GCC | ATT | GAA | CCG | AGA | GAC | GTA | GCA | AGG | TAC | CCC | 384 |
| Ile | Phe | His | Asn | Val | Ala | Ile | Glu | Pro | Arg | Asp | Val | Ala | Arg | Tyr | Pro | |
| | | 115 | | | | | 120 | | | | | 125 | | | | |
| AAG | GAA | ACA | ATA | ATT | GAC | AAA | CTC | ACA | GAG | ATC | ACA | ACA | GAC | ACA | GCA | 432 |
| Lys | Glu | Thr | Ile | Ile | Asp | Lys | Leu | Thr | Glu | Ile | Thr | Thr | Asp | Thr | Ala | |
| | | 130 | | | | | 135 | | | | | 140 | | | | |
| TAC | ATT | AGT | GAC | ACT | CTG | CAC | TTC | TTG | GAT | CCG | AGC | TAC | ATA | GTG | GAG | 480 |
| Tyr | Ile | Ser | Asp | Thr | Leu | His | Phe | Leu | Asp | Pro | Ser | Tyr | Ile | Val | Glu | |
| 145 | | | | | 150 | | | | | 155 | | | | | 160 | |
| ACA | TTC | CAA | AAC | TGC | CCA | AAA | CTG | CAA | ACA | TTG | TAT | GCG | ACC | TTA | GTT | 528 |
| Thr | Phe | Gln | Asn | Cys | Pro | Lys | Leu | Gln | Thr | Leu | Tyr | Ala | Thr | Leu | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| CTC | CCC | GTT | GAG | GCA | GCC | TTC | AAA | ATG | GAA | AGC | ACT | CAC | CCG | AAC | ATA | 576 |
| Leu | Pro | Val | Glu | Ala | Ala | Phe | Lys | Met | Glu | Ser | Thr | His | Pro | Asn | Ile | |
| | | | 180 | | | | 185 | | | | | | 190 | | | |
| TAC | AGC | CTC | AAA | TAC | TTC | GGA | GAT | GGT | TTC | CAG | TAT | ATA | CCA | GGC | AAC | 624 |
| Tyr | Ser | Leu | Lys | Tyr | Phe | Gly | Asp | Gly | Phe | Gln | Tyr | Ile | Pro | Gly | Asn | |
| | | 195 | | | | | 200 | | | | | 205 | | | | |
| CAT | GGT | GGT | GGA | GCG | TAC | CAT | CAT | GAA | TTT | GCT | CAT | TTA | CAA | TGG | CTC | 672 |
| His | Gly | Gly | Gly | Ala | Tyr | His | His | Glu | Phe | Ala | His | Leu | Gln | Trp | Leu | |
| | | 210 | | | | | 215 | | | | 220 | | | | | |
| AAA | GTG | GGA | AAG | ATC | AAA | TGG | AGG | GAC | CCC | AAG | GAT | AGC | TTT | CTC | GGA | 720 |
| Lys | Val | Gly | Lys | Ile | Lys | Trp | Arg | Asp | Pro | Lys | Asp | Ser | Phe | Leu | Gly | |
| 225 | | | | | 230 | | | | | 235 | | | | | 240 | |
| CAT | CTC | AAT | TAC | ACG | ACT | GAG | CAG | GTT | GAG | ATG | CAC | ACA | GTG | ACA | GTG | 768 |
| His | Leu | Asn | Tyr | Thr | Thr | Glu | Gln | Val | Glu | Met | His | Thr | Val | Thr | Val | |
| | | | | 245 | | | | | 250 | | | | | 255 | | |
| CAG | TTG | CAG | GAA | TCG | TTC | GCG | GCA | AAC | CAC | TTG | TAC | TGC | ATC | AGG | AGA | 816 |
| Gln | Leu | Gln | Glu | Ser | Phe | Ala | Ala | Asn | His | Leu | Tyr | Cys | Ile | Arg | Arg | |
| | | | 260 | | | | | 265 | | | | | 270 | | | |
| GGA | GAT | TTG | CTC | ACA | CCG | GAG | GTG | CGC | ACT | TTT | GGC | AAC | CCT | GAC | AGG | 864 |
| Gly | Asp | Leu | Leu | Thr | Pro | Glu | Val | Arg | Thr | Phe | Gly | Gln | Pro | Asp | Arg | |
| | | | 275 | | | | 280 | | | | | 285 | | | | |
| TAT | GTG | ATT | CCA | CCA | CAG | ATC | TTC | CTC | CCG | AAA | GTC | CAT | AAC | TGC | AAG | 912 |
| Tyr | Val | Ile | Pro | Pro | Gln | Ile | Phe | Leu | Pro | Lys | Val | His | Asn | Cys | Lys | |
| | 290 | | | | | 295 | | | | | 300 | | | | | |
| AAG | CCG | ATT | CTT | AAA | AAA | ACT | ATG | ATG | CAG | CTC | TTC | TTG | TAT | GTT | AGG | 960 |
| Lys | Pro | Ile | Leu | Lys | Lys | Thr | Met | Met | Gln | Leu | Phe | Leu | Tyr | Val | Arg | |
| 305 | | | | | 310 | | | | | 315 | | | | | 320 | |
| ACA | GTT | AAG | GTC | GCA | AAA | AAT | TGT | GAC | ATT | TTT | GCC | AAA | GTC | AGA | CAA | 1008 |
| Thr | Val | Lys | Val | Ala | Lys | Asn | Cys | Asp | Ile | Phe | Ala | Lys | Val | Arg | Gln | |
| | | | | 325 | | | | | 330 | | | | | 335 | | |
| TTA | ATT | AAA | TCA | TCT | GAC | CTG | GAC | AAA | TAT | TCT | GCT | GTG | GAA | CTG | GTT | 1056 |
| Leu | Ile | Lys | Ser | Ser | Asp | Leu | Asp | Lys | Tyr | Ser | Ala | Val | Glu | Leu | Val | |
| | | | 340 | | | | | 345 | | | | | 350 | | | |
| TAC | TTA | GTA | AGC | TAT | ATG | GAG | TTC | CTT | GCC | GAT | CTA | CAA | GCT | ACC | ACC | 1104 |
| Tyr | Leu | Val | Ser | Tyr | Met | Glu | Phe | Leu | Ala | Asp | Leu | Gln | Ala | Thr | Thr | |
| | | 355 | | | | | 360 | | | | | 365 | | | | |
| TGC | TTC | TCA | GAC | ACA | CTT | TCT | GGT | GGC | TTA | CTA | ACA | AAG | ACC | TTG | GCA | 1152 |
| Cys | Phe | Ser | Asp | Thr | Leu | Ser | Gly | Gly | Leu | Leu | Thr | Lys | Thr | Leu | Ala | |
| | 370 | | | | | 375 | | | | | 380 | | | | | |
| CCG | GTG | AGG | GCT | TGG | ATA | CAA | GAG | AAA | AAG | ATG | CAG | CTG | TTT | GGT | CTT | 1200 |
| Pro | Val | Arg | Ala | Trp | Ile | Gln | Glu | Lys | Lys | Met | Gln | Leu | Phe | Gly | Leu | |
| 385 | | | | | 390 | | | | | 395 | | | | | 400 | |
| GAG | GAC | TAC | GCG | AAG | TTA | GTC | AAA | GCA | GTT | GAT | TTC | CAC | CCA | GTG | GAT | 1248 |
| Glu | Asp | Tyr | Ala | Lys | Leu | Val | Lys | Ala | Val | Asp | Phe | His | Pro | Val | Asp | |
| | | | | 405 | | | | | 410 | | | | | 415 | | |
| TTT | TCT | TTT | AAA | GTT | GAA | ACT | TGG | GAC | TTC | AGA | TTC | CAC | CCC | TTG | CAA | 1296 |
| Phe | Ser | Phe | Lys | Val | Glu | Thr | Trp | Asp | Phe | Arg | Phe | His | Pro | Leu | Gln | |
| | | | 420 | | | | | 425 | | | | | 430 | | | |
| GCG | TGG | AAA | GCC | TTC | CGA | CCA | AGG | GAA | GTG | TCG | GAT | GTA | GAG | GAA | ATG | 1344 |
| Ala | Trp | Lys | Ala | Phe | Arg | Pro | Arg | Glu | Val | Ser | Asp | Val | Glu | Glu | Met | |
| | | 435 | | | | | 440 | | | | | 445 | | | | |
| GAA | AGT | TTG | TTC | TCA | GAT | GGG | GAC | CTG | CTT | GAC | TGC | TTC | ACA | AGA | ATG | 1392 |
| Glu | Ser | Leu | Phe | Ser | Asp | Gly | Asp | Leu | Leu | Asp | Cys | Phe | Thr | Arg | Met | |
| | 450 | | | | | 455 | | | | | 460 | | | | | |
| CCA | GCT | TAT | GCA | GTA | AAC | GCA | GAG | GAA | GAT | TTA | GCT | ACA | ATC | AGG | AAA | 1440 |
| Pro | Ala | Tyr | Ala | Val | Asn | Ala | Glu | Glu | Asp | Leu | Ala | Thr | Ile | Arg | Lys | |
| 465 | | | | | 470 | | | | | 475 | | | | | 480 | |
| ACG | CCC | GAG | ATG | GAT | GTC | GGT | CAA | GAA | GCC | AAA | GAA | CCT | GCA | GGA | GAC | 1488 |
| Thr | Pro | Glu | Met | Asp | Val | Gly | Gln | Glu | Ala | Lys | Glu | Pro | Ala | Gly | Asp | |
| | | | | 485 | | | | | 490 | | | | | 495 | | |

| | | | | | | | | | | | | | | | | |
|---|---|---|---|---|---|---|---|---|---|---|---|---|---|---|---|---|
| AGA | AAT | CAA | TAC | TTA | AAC | CCT | GCA | GAA | ACT | TTC | CTC | AAC | AAG | CTC | CAC | 1536 |
| Arg | Asn | Gln | Tyr | Leu | Asn | Pro | Ala | Glu | Thr | Phe | Leu | Asn | Lys | Leu | His | |
| | | | 500 | | | | 505 | | | | | 510 | | | | |
| AGG | AAA | CAC | AGT | AGG | GAG | GTG | AAA | CAT | CAG | GCC | GTA | AAG | AAA | GCT | AAA | 1584 |
| Arg | Lys | His | Ser | Arg | Glu | Val | Lys | His | Gln | Ala | Val | Lys | Lys | Ala | Lys | |
| | | 515 | | | | | 520 | | | | | 525 | | | | |
| CGC | CTA | GCT | GAA | ATC | CAG | GAG | TCC | ATG | AGA | GCT | GAG | GGT | GAG | GCC | GAA | 1632 |
| Arg | Leu | Ala | Glu | Ile | Gln | Glu | Ser | Met | Arg | Ala | Glu | Gly | Glu | Ala | Glu | |
| | 530 | | | | | 535 | | | | | 540 | | | | | |
| CTA | AAT | GAG | ATG | AGC | GGG | GGC | ATG | AGG | GCA | ATA | CCT | AGC | AAC | GCA | GAA | 1680 |
| Leu | Asn | Glu | Met | Ser | Gly | Gly | Met | Arg | Ala | Ile | Pro | Ser | Asn | Ala | Glu | |
| 545 | | | | | 550 | | | | | 555 | | | | | 560 | |
| CTT | CCC | AGC | ACG | AAC | GAT | GCT | AGA | CAA | GAA | CTC | ACA | CTC | CCA | ACC | ACT | 1728 |
| Leu | Pro | Ser | Thr | Asn | Asp | Ala | Arg | Gln | Glu | Leu | Thr | Leu | Pro | Thr | Thr | |
| | | | | 565 | | | | | 570 | | | | | 575 | | |
| AAA | CCT | GTC | CCT | GCA | AGG | TGG | GAA | GAT | GCT | TCA | TTC | ACA | GAT | TCT | AGT | 1776 |
| Lys | Pro | Val | Pro | Ala | Arg | Trp | Glu | Asp | Ala | Ser | Phe | Thr | Asp | Ser | Ser | |
| | | | 580 | | | | | 585 | | | | | 590 | | | |
| GTG | AAA | GAG | GAG | CAA | GTG | AAA | CTC | CCT | GGA | AAA | GAA | GCC | GTT | GAG | ACA | 1824 |
| Val | Lys | Glu | Glu | Gln | Val | Lys | Leu | Pro | Gly | Lys | Glu | Ala | Val | Glu | Thr | |
| | | | 595 | | | | | 600 | | | | | 605 | | | |
| GCG | ACG | CAA | CAA | GTC | ATA | GAA | GGA | CTC | CCT | TGG | AAA | CAC | TGG | ATT | CCT | 1872 |
| Ala | Thr | Gln | Gln | Val | Ile | Glu | Gly | Leu | Pro | Trp | Lys | His | Trp | Ile | Pro | |
| 610 | | | | | 615 | | | | | 620 | | | | | | |
| CAA | CTA | AAT | GCT | GTT | GGA | TTC | AAG | GCG | CTG | GAA | ATT | CAG | AGG | GAT | AGG | 1920 |
| Gln | Leu | Asn | Ala | Val | Gly | Phe | Lys | Ala | Leu | Glu | Ile | Gln | Arg | Asp | Arg | |
| 625 | | | | | 630 | | | | | 635 | | | | | 640 | |
| AGT | GGG | ACA | ATG | ATC | ATG | CCC | ATC | ACA | GAA | ATG | GTC | TCC | GGG | TTG | GAA | 1968 |
| Ser | Gly | Thr | Met | Ile | Met | Pro | Ile | Thr | Glu | Met | Val | Ser | Gly | Leu | Glu | |
| | | | | 645 | | | | | 650 | | | | | 655 | | |
| AAA | GAG | GAC | TTC | CCG | GAA | GGA | ACT | CCA | AAA | GAG | TTG | GCA | CGA | GAA | TTG | 2016 |
| Lys | Glu | Asp | Phe | Pro | Glu | Gly | Thr | Pro | Lys | Glu | Leu | Ala | Arg | Glu | Leu | |
| | | | 660 | | | | | 665 | | | | | 670 | | | |
| CTC | GCT | AAG | AGC | TCG | CCC | GGG | GAT | CCA | GCT | TTC | GTT | CGT | ATC | GGT | TTC | 2064 |
| Leu | Ala | Lys | Ser | Ser | Pro | Gly | Asp | Pro | Ala | Phe | Val | Arg | Ile | Gly | Phe | |
| | | 675 | | | | | 680 | | | | | 685 | | | | |
| GAC | AAC | GTT | CGT | CAA | GTT | CAA | TGC | ATC | AGT | TTC | ATT | GCG | CAC | ACA | CCA | 2112 |
| Asp | Asn | Val | Arg | Gln | Val | Gln | Cys | Ile | Ser | Phe | Ile | Ala | His | Thr | Pro | |
| | 690 | | | | | 695 | | | | | 700 | | | | | |
| GAA | TCC | TAC | TGA | | | | | | | | | | | | | 2124 |
| Glu | Ser | Tyr | | | | | | | | | | | | | | |
| 705 | | | | | | | | | | | | | | | | |

( 2 ) INFORMATION FOR SEQ ID NO:12:

( i ) SEQUENCE CHARACTERISTICS:
        ( A ) LENGTH: 707 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Met | Ala | Lys | Val | Arg | Glu | Val | Tyr | Gln | Ser | Phe | Thr | Asp | Ser | Thr | Thr |
| 1 | | | | 5 | | | | | 10 | | | | | 15 | |
| Lys | Thr | Leu | Ile | Gln | Asp | Glu | Ala | Tyr | Arg | Asn | Ile | Arg | Pro | Ile | Met |
| | | | 20 | | | | | 25 | | | | | 30 | | |
| Glu | Lys | His | Lys | Leu | Ala | Asn | Pro | Tyr | Ala | Gln | Thr | Val | Glu | Ala | Ala |
| | | 35 | | | | | 40 | | | | | 45 | | | |
| Asn | Asp | Leu | Glu | Gly | Phe | Gly | Ile | Ala | Thr | Asn | Pro | Tyr | Ser | Ile | Glu |
| | 50 | | | | | 55 | | | | | 60 | | | | |

| | | | | | | | | | | | | | | |
|---|---|---|---|---|---|---|---|---|---|---|---|---|---|---|
| Leu | His | Thr | His | Ala | Ala | Ala | Lys | Thr | Ile | Glu | Asn | Lys | Leu | Leu | Glu |
| 65 | | | | | 70 | | | | 75 | | | | | | 80 |
| Val | Leu | Gly | Ser | Ile | Leu | Pro | Gln | Glu | Pro | Val | Thr | Phe | Met | Phe | Leu |
| | | | | 85 | | | | | 90 | | | | | 95 | |
| Lys | Pro | Arg | Lys | Leu | Asn | Tyr | Met | Arg | Arg | Asn | Pro | Arg | Ile | Lys | Asp |
| | | | 100 | | | | | 105 | | | | | 110 | | |
| Ile | Phe | His | Asn | Val | Ala | Ile | Glu | Pro | Arg | Asp | Val | Ala | Arg | Tyr | Pro |
| | | | 115 | | | | 120 | | | | | 125 | | | |
| Lys | Glu | Thr | Ile | Ile | Asp | Lys | Leu | Thr | Glu | Ile | Thr | Thr | Asp | Thr | Ala |
| | | | 130 | | | | 135 | | | | | 140 | | | |
| Tyr | Ile | Ser | Asp | Thr | Leu | His | Phe | Leu | Asp | Pro | Ser | Tyr | Ile | Val | Glu |
| 145 | | | | | 150 | | | | | 155 | | | | | 160 |
| Thr | Phe | Gln | Asn | Cys | Pro | Lys | Leu | Gln | Thr | Leu | Tyr | Ala | Thr | Leu | Val |
| | | | | 165 | | | | | 170 | | | | | 175 | |
| Leu | Pro | Val | Glu | Ala | Ala | Phe | Lys | Met | Glu | Ser | Thr | His | Pro | Asn | Ile |
| | | | | 180 | | | | | 185 | | | | | 190 | |
| Tyr | Ser | Leu | Lys | Tyr | Phe | Gly | Asp | Gly | Phe | Gln | Tyr | Ile | Pro | Gly | Asn |
| | | | 195 | | | | 200 | | | | | 205 | | | |
| His | Gly | Gly | Gly | Ala | Tyr | His | His | Glu | Phe | Ala | His | Leu | Gln | Trp | Leu |
| | 210 | | | | | 215 | | | | | 220 | | | | |
| Lys | Val | Gly | Lys | Ile | Lys | Trp | Arg | Asp | Pro | Lys | Asp | Ser | Phe | Leu | Gly |
| 225 | | | | | 230 | | | | | 235 | | | | | 240 |
| His | Leu | Asn | Tyr | Thr | Thr | Glu | Gln | Val | Glu | Met | His | Thr | Val | Thr | Val |
| | | | | 245 | | | | | 250 | | | | | 255 | |
| Gln | Leu | Gln | Glu | Ser | Phe | Ala | Ala | Asn | His | Leu | Tyr | Cys | Ile | Arg | Arg |
| | | | 260 | | | | | 265 | | | | | 270 | | |
| Gly | Asp | Leu | Leu | Thr | Pro | Glu | Val | Arg | Thr | Phe | Gly | Gln | Pro | Asp | Arg |
| | | | 275 | | | | | 280 | | | | | 285 | | |
| Tyr | Val | Ile | Pro | Pro | Gln | Ile | Phe | Leu | Pro | Lys | Val | His | Asn | Cys | Lys |
| | | 290 | | | | | 295 | | | | | 300 | | | |
| Lys | Pro | Ile | Leu | Lys | Lys | Thr | Met | Met | Gln | Leu | Phe | Leu | Tyr | Val | Arg |
| 305 | | | | | 310 | | | | | 315 | | | | | 320 |
| Thr | Val | Lys | Val | Ala | Lys | Asn | Cys | Asp | Ile | Phe | Ala | Lys | Val | Arg | Gln |
| | | | | 325 | | | | | 330 | | | | | 335 | |
| Leu | Ile | Lys | Ser | Ser | Asp | Leu | Asp | Lys | Tyr | Ser | Ala | Val | Glu | Leu | Val |
| | | | | 340 | | | | | 345 | | | | | 350 | |
| Tyr | Leu | Val | Ser | Tyr | Met | Glu | Phe | Leu | Ala | Asp | Leu | Gln | Ala | Thr | Thr |
| | | | 355 | | | | | 360 | | | | | 365 | | |
| Cys | Phe | Ser | Asp | Thr | Leu | Ser | Gly | Gly | Leu | Leu | Thr | Lys | Thr | Leu | Ala |
| | | | 370 | | | | | 375 | | | | | 380 | | |
| Pro | Val | Arg | Ala | Trp | Ile | Gln | Glu | Lys | Lys | Met | Gln | Leu | Phe | Gly | Leu |
| 385 | | | | | 390 | | | | | 395 | | | | | 400 |
| Glu | Asp | Tyr | Ala | Lys | Leu | Val | Lys | Ala | Val | Asp | Phe | His | Pro | Val | Asp |
| | | | | 405 | | | | | 410 | | | | | 415 | |
| Phe | Ser | Phe | Lys | Val | Glu | Thr | Trp | Asp | Phe | Arg | Phe | His | Pro | Leu | Gln |
| | | | 420 | | | | | 425 | | | | | 430 | | |
| Ala | Trp | Lys | Ala | Phe | Arg | Pro | Arg | Glu | Val | Ser | Asp | Val | Glu | Glu | Met |
| | | 435 | | | | | 440 | | | | | 445 | | | |
| Glu | Ser | Leu | Phe | Ser | Asp | Gly | Asp | Leu | Leu | Asp | Cys | Phe | Thr | Arg | Met |
| | | 450 | | | | | 455 | | | | | 460 | | | |
| Pro | Ala | Tyr | Ala | Val | Asn | Ala | Glu | Glu | Asp | Leu | Ala | Thr | Ile | Arg | Lys |
| 465 | | | | | 470 | | | | | 475 | | | | | 480 |
| Thr | Pro | Glu | Met | Asp | Val | Gly | Gln | Glu | Ala | Lys | Glu | Pro | Ala | Gly | Asp |
| | | | | 485 | | | | | 490 | | | | | 495 | |

| | | | | | | | | | | | | | | |
|---|---|---|---|---|---|---|---|---|---|---|---|---|---|---|
| Arg | Asn | Gln | Tyr<br>500 | Leu | Asn | Pro | Ala | Glu<br>505 | Thr | Phe | Leu | Asn | Lys<br>510 | Leu | His |
| Arg | Lys | His<br>515 | Ser | Arg | Glu | Val | Lys<br>520 | His | Gln | Ala | Val | Lys<br>525 | Lys | Ala | Lys |
| Arg | Leu<br>530 | Ala | Glu | Ile | Gln | Glu<br>535 | Ser | Met | Arg | Ala | Glu<br>540 | Gly | Glu | Ala | Glu |
| Leu<br>545 | Asn | Glu | Met | Ser | Gly<br>550 | Gly | Met | Arg | Ala | Ile<br>555 | Pro | Ser | Asn | Ala | Glu<br>560 |
| Leu | Pro | Ser | Thr | Asn<br>565 | Asp | Ala | Arg | Gln | Glu<br>570 | Leu | Thr | Leu | Pro | Thr<br>575 | Thr |
| Lys | Pro | Val | Pro<br>580 | Ala | Arg | Trp | Glu | Asp<br>585 | Ala | Ser | Phe | Thr | Asp<br>590 | Ser | Ser |
| Val | Lys | Glu<br>595 | Glu | Gln | Val | Lys | Leu<br>600 | Pro | Gly | Lys | Glu | Ala<br>605 | Val | Glu | Thr |
| Ala | Thr<br>610 | Gln | Gln | Val | Ile | Glu<br>615 | Gly | Leu | Pro | Trp | Lys<br>620 | His | Trp | Ile | Pro |
| Gln<br>625 | Leu | Asn | Ala | Val | Gly<br>630 | Phe | Lys | Ala | Leu | Glu<br>635 | Ile | Gln | Arg | Asp | Arg<br>640 |
| Ser | Gly | Thr | Met | Ile<br>645 | Met | Pro | Ile | Thr | Glu<br>650 | Met | Val | Ser | Gly | Leu<br>655 | Glu |
| Lys | Glu | Asp | Phe<br>660 | Pro | Glu | Gly | Thr | Pro<br>665 | Lys | Glu | Leu | Ala | Arg<br>670 | Glu | Leu |
| Leu | Ala | Lys<br>675 | Ser | Ser | Pro | Gly | Asp<br>680 | Pro | Ala | Phe | Val | Arg<br>685 | Ile | Gly | Phe |
| Asp | Asn<br>690 | Val | Arg | Gln | Val | Gln<br>695 | Cys | Ile | Ser | Phe | Ile<br>700 | Ala | His | Thr | Pro |
| Glu<br>705 | Ser | Tyr | | | | | | | | | | | | | |

What is claimed is:

1. A double stranded DNA molecule comprising:
   a promoter that functions in plant cells to cause the production of an RNA sequence; which is operably linked to a DNA sequence encoding shown as SEQ ID NO: 1 a full length PVX replicase protein; which is operably linked to a 3' non-translated DNA sequence that functions in plants to cause the addition of polyadenylated ribonucleotides to the 3' end of the transcribed mRNA sequence.

2. The double stranded DNA molecule of claim 1 wherein the promoter comprises a native PVX 5' non-translated leader sequence.

3. The double stranded DNA molecule of claim 1 wherein said promoter is selected from the group consisting of the FMV35S promoter, the CaMV35S promoter and the enhanced CaMV35S promoter.

4. A method for providing resistance in Solanaceae plants to infection by PVX comprising the steps of:
   stably transforming cells of a Solanaceae plant with a DNA sequence encoding shown as SEQ ID NO: 1 a full length PVX replicase protein; and
   selecting transformed plants which express said DNA sequence at a level sufficient to render the plants resistant to infection by PVX.

5. A method of claim 4 wherein said Solanaceae plant is selected from the group consisting of potato and tomato.

6. A method of claim 5 wherein said plant is potato.

7. A transgenic potato plant cell which contains in its genome the double stranded DNA molecule of claim 1.

8. A potato plant comprising cells of claim 7.

9. A transgenic potato tuber comprising cells of claim 7.

10. A double stranded DNA molecule comprising:
    a promoter which functions in plant cells to cause the production of an RNA sequence;
    which is operably linked to a DNA sequence encoding a truncated PVX replicase protein comprising at least the first 45% of a PVX replicase protein; which is operably linked to a 3' non-translated DNA sequence that functions in plants to cause the polyadenylation of the 3' end of the transcribed mRNA sequence.

* * * * *

UNITED STATES PATENT AND TRADEMARK OFFICE
CERTIFICATE OF CORRECTION

PATENT NO.    : 5,773,701
DATED         : JUNE 30, 1998
INVENTOR(S)   : Carl Joseph Braun, III/Cynthia Lou Hemenway/Nilgun Ereken Tumer It is certified that error appears in the above-identified patent and that said Letters Patent is hereby corrected as shown below:

In claim 1, line 43, after "sequence", delete --encoding--.

In claim 1, line 44, after "NO: 1", insert --encoding--.

In claim 4, line 59, after "sequence", delete --encoding-- and after "NO: 1", insert --encoding--.

Signed and Sealed this

Third Day of November, 1998

Attest:

BRUCE LEHMAN

Attesting Officer

Commissioner of Patents and Trademarks